(12) United States Patent
Kim et al.

(10) Patent No.: US 11,905,536 B2
(45) Date of Patent: Feb. 20, 2024

(54) ANTI-INFLAMMATORY PEPTIDES AND COMPOSITION COMPRISING THE SAME

(71) Applicants: GemVax & KAEL Co., Ltd., Daejeon (KR); Sang Jae Kim, Seoul (KR)

(72) Inventors: Sang Jae Kim, Seoul (KR); Kyung Hee Kim, Seongnam-si (KR); Kyu-Yong Lee, Seongnam-si (KR); Seong-Ho Koh, Seongnam-si (KR); Bum Joon Kim, Seongnam-si (KR); Hyun-Hee Park, Seongnam-si (KR); Sung Jin Huh, Seongnam-si (KR); Woo Jin Lee, Seongnam-si (KR); Hwain Jang, Seongnam-si (KR); Jung Soon Ha, Seongnam-si (KR)

(73) Assignees: GemVax & KAEL Co., Ltd., Daejeon (KR); Sang Jae Kim, Seoul (KR)

(*) Notice: Subject to any disclaimer, the term of this patent is extended or adjusted under 35 U.S.C. 154(b) by 3 days.

(21) Appl. No.: 17/389,671

(22) Filed: Jul. 30, 2021

(65) Prior Publication Data
US 2021/0388328 A1 Dec. 16, 2021

Related U.S. Application Data

(62) Division of application No. 16/818,001, filed on Mar. 13, 2020, now Pat. No. 11,098,294, which is a division of application No. 14/400,322, filed as application No. PCT/EP2013/055326 on Mar. 15, 2013, now abandoned.

(30) Foreign Application Priority Data

| Jul. 20, 2012 | (KR) | 10-2012-0079096 |
| Aug. 14, 2012 | (KR) | 10-2012-0089161 |
| Aug. 14, 2012 | (KR) | 10-2012-0089162 |
| Aug. 14, 2012 | (KR) | 10-2012-0089167 |
| Sep. 19, 2012 | (KR) | 10-2012-0104144 |
| Sep. 19, 2012 | (KR) | 10-2012-0104207 |

(51) Int. Cl.
*A61K 38/45* (2006.01)
*C12N 9/12* (2006.01)
*A23L 33/18* (2016.01)

(52) U.S. Cl.
CPC ............ *C12N 9/1276* (2013.01); *A23L 33/18* (2016.08); *A61K 38/45* (2013.01); *A23V 2002/00* (2013.01); *C12Y 207/07049* (2013.01); *Y02A 50/30* (2018.01)

(58) Field of Classification Search
None
See application file for complete search history.

(56) References Cited

U.S. PATENT DOCUMENTS

| 4,427,649 A | 1/1984 | Dingle et al. |
| 7,030,211 B1 | 4/2006 | Gaudernack et al. |
| 8,252,282 B2 | 8/2012 | Santos |
| 8,362,209 B2 | 1/2013 | Santos |
| 9,527,888 B2 | 12/2016 | Kim et al. |
| 9,572,900 B2 | 2/2017 | Kim |
| 9,631,184 B2 | 4/2017 | Kim |
| 9,757,473 B2 | 9/2017 | Kim |
| 9,902,945 B2 | 2/2018 | Kim |
| 10,383,926 B2 | 8/2019 | Kim |
| 11,098,294 B2 | 8/2021 | Kim et al. |
| 2007/0190561 A1 | 8/2007 | Morin et al. |
| 2010/0311741 A1 | 12/2010 | Jirgensons et al. |
| 2011/0150873 A1 | 6/2011 | Grainger |
| 2011/0183925 A1 | 7/2011 | Sato et al. |
| 2011/0318380 A1 | 12/2011 | Brix et al. |
| 2015/0099692 A1 | 4/2015 | Kim et al. |
| 2015/0099693 A1 | 4/2015 | Kim et al. |
| 2015/0125438 A1 | 5/2015 | Kim et al. |
| 2016/0120966 A1 | 5/2016 | Kim |
| 2017/0081376 A1 | 3/2017 | Kim et al. |

(Continued)

FOREIGN PATENT DOCUMENTS

| JP | 2002-520293 A | 7/2002 |
| KR | 20110060940 A | 6/2011 |

(Continued)

OTHER PUBLICATIONS

Bradley, "TNF-mediated inflammatory disease," J. Pathol. 214(2):149-160 (2008).
"Corticosteroids Systemic (Oral and Injectable)," MedicineNet, Ogbru, <https://www.medicinenet.com/corticosteroids-oral/article.htm>, retrieved on Mar. 14, 2018 (13 pages).
"Medulla," Google Search, <https://www.google.com/?gws_rd=ssl#q=medulla>, retrieved on Apr. 8, 2016 (2 pages).
Advisory Action for U.S. Appl. No. 14/429,637, (filed Mar. 19, 2015), dated Jul. 5, 2017 (3 pages).

(Continued)

*Primary Examiner* — Ronald T Niebauer
(74) *Attorney, Agent, or Firm* — Clark & Elbing LLP; Susan M. Michaud

(57) ABSTRACT

The present invention relates to a peptide with anti-inflammatory activity, wherein the peptide comprises any one amino acid sequence of SEQ ID NO: 1 to SEQ ID NO: 161, the peptide has above 80% homology of amino acid sequence with above-mentioned sequences, or the peptide is the fragment of the above-mentioned peptides. The present invention also relates to an inflammatory composition comprising the above mentioned peptides. According to the present invention, a peptide that has at least one amino acid sequence of SEQ ID NO: 1 to SEQ ID NO: 161 has outstanding efficacy in both suppressing inflammation and in prophylactic means. Therefore, the composition comprising the peptides of this invention can be used as anti-inflammatory pharmaceutical compositions or as cosmetic compositions, in turn, treating and preventing a variety of different types of inflammatory diseases.

6 Claims, 54 Drawing Sheets

Specification includes a Sequence Listing.

(56) References Cited

U.S. PATENT DOCUMENTS

| | | | |
|---|---|---|---|
| 2017/0112941 | A1 | 4/2017 | Panitch et al. |
| 2017/0112942 | A1 | 4/2017 | Kim |
| 2017/0275603 | A1 | 9/2017 | Kim et al. |
| 2018/0134749 | A1 | 5/2018 | Kim |
| 2020/0208127 | A1 | 7/2020 | Kim et al. |

FOREIGN PATENT DOCUMENTS

| | | |
|---|---|---|
| KR | 20120130996 A | 12/2012 |
| KR | 20120133661 A | 12/2012 |
| WO | WO-00/02581 A1 | 1/2000 |
| WO | WO-2009/025871 A1 | 2/2009 |
| WO | WO-2010/003520 A2 | 1/2010 |
| WO | WO-2011/101173 A1 | 8/2011 |

OTHER PUBLICATIONS

Altschul et al., "Basic local alignment search tool," J. Mol. Biol. 215: 403-410 (1990).
Armstrong et al., "Mitochondrial medicine: pharmacological targeting of mitochondria in disease," Br. J. Pharmacol. 151(8):1154-1165 (2007).
Bonaldi et al., "Monocytic cells hyperacetylate chromatin protein HMGB1 to redirect it towards secretion," EMBO J. 22(20):5551-5560 (2003).
Cho, "A godsend about to arrive," GemVax, Hana Daetoo Securities Co., Ltd., Company Report (2012) (9 pages).
Dahlgren et al., "Oligomeric and fibrillar species of amyloid-beta peptides differentially affect neuronal viability," J. Biol. Chem. 277(35):32046-32053 (2002).
Du et al., "Conformational and topological requirements of cell-permeable peptide function," J. Pept. Res. 51(3):235-243 (1998).
Final Office Action for U.S. Appl. No. 14/429,637, (filed Mar. 19, 2015), dated Mar. 29, 2017 (13 pages).
Fonseca et al., "Recent advances in the use of cell-penetrating peptides for medical and biological applications," Adv. Drug Deliv. Rev. 61(11):953-964 (2009).
Ge et al., "A comparison of five bioconjugatable ferrocenes for labeling of biomolecules," Chem. Commun. (Camb). 46(38):7190-7192 (2010).
Godet et al., "Analysis of spontaneous tumor-specific CD4 T-cell immunity in lung cancer using promiscuous HLA-DR telomerase-derived epitopes: potential synergistic effect with chemotherapy response," Clin. Cancer Res. 18(10):2943-2953 (2012).
Heitz et al., "Twenty years of cell-penetrating peptides: from molecular mechanisms to therapeutics," Br. J. Pharmacol. 157(2):195-206 (2009).
Horwich et al., "A leader peptide is sufficient to direct mitochondrial import of a chimeric protein," EMBO J. 4(5):1129-1135 (1985).
International Preliminary Report on Patentability for International Application No. PCT/EP2013/055327, dated Nov. 11, 2014 (7 pages).
International Preliminary Report on Patentability for International Application No. PCT/EP2013/059460, dated Nov. 11, 2014 (5 pages).
International Preliminary Report on Patentability for International Application No. PCT/KR2013/008438, dated Mar. 24, 2015 (10 pages).
International Search Report for International Application No. PCT/EP2013/055326, dated Jul. 19, 2013 (7 pages).
International Search Report for International Application No. PCT/EP2013/059460, dated Jul. 3, 2013 (5 pages).
International Search Report for International Patent Application No. PCT/EP2013/055327, dated Oct. 9, 2013 (8 pages).
International Search Report for International Patent Application No. PCT/EP2013/059460, dated Jul. 3, 2013 (5 pages).
International Search Report for International Patent Application No. PCT/KR2013/008438, dated Dec. 23, 2013 (8 pages).
Kalafatovic et al., "Cell-penetrating peptides: design strategies beyond primary structure and amphipathicity," Molecules 22(11):1929 (2017) (38 pages).
Kalnins et al., "Sequence of the lacZ gene of *Escherichia coli*," EMBO J. 2(4):593-597 (1983).
Ko et al., "The anti-inflammatory effect of human telomerase-derived peptide on P. gingivalis lipopolysaccharide-induced inflammatory cytokine production and its mechanism in human dental pulp cells," Mediators Inflamm. 2015:385127 (2015) (8 pages).
Lee et al., "Heat shock protein-mediated cell penetration and cytosolic delivery of macromolecules by a telomerase-derived peptide vaccine," Biomaterials 34(30):7495-7505 (2013).
Lopez et al., "Mitochondria-targeted nitroxides as MRI contrast agents and chemotherapeutics," Free Radical Biology & Medicine 45(Suppl. 1):S55 (2008) (1 page).
Luft et al., "A case of severe hypermetabolism of nonthyroid origin with a defect in the maintenance of mitochondrial respiratory control: a correlated clinical, biochemical, and morphological study," J. Clin. Invest. 41(9):1776-1804 (1962).
Martinez et al., "Telomeric and extra-telomeric roles for telomerase and the telomere-binding proteins," Nat. Rev. Cancer 11(3):161-176 (2011).
NCBI GenBank Accession No. AAC51672.1, "Telomerase reverse transcriptase [*Homo sapiens*]," <http://www.ncbi.nlm.nih.gov/protein/2330017, published 1997, accessed Oct. 22, 2015 (3 pages).
Non-Final Office Action for U.S. Appl. No. 14/903,827, (filed Jan. 8, 2016), dated Dec. 22, 2016 (12 pages).
Non-Final Office Action for U.S. Appl. No. 14/400,321, (filed Nov. 10, 2014), dated Apr. 25, 2016 (20 pages).
Non-Final Office Action for U.S. Appl. No. 14/400,322, (filed Nov. 10, 2014), dated Apr. 12, 2016 (17 pages).
Non-Final Office Action for U.S. Appl. No. 14/400,322, (filed Nov. 10, 2014), dated Mar. 26, 2018 (21 pages).
Non-Final Office Action for U.S. Appl. No. 14/429,637, (filed Mar. 19, 2015), dated Nov. 2, 2016 (11 pages).
Non-Final Office Action for U.S. Appl. No. 14/429,644, (filed Mar. 19, 2015), dated Apr. 22, 2016 (42 pages).
Pearson et al., "Improved tools for biological sequence comparison," Proc. Natl. Acad. Sci. U.S.A. 85:2444-2448 (1988).
Salaklang et al., "Superparamagnetic nanoparticles as a powerful systems biology characterization tool in the physiological context," Angew Chem. Int. Ed. Engl. 47(41):7857-7860 (2008).
Santos et al., "Mitochondrial hTERT exacerbates free-radical-mediated mtDNA damage," Aging Cell 3(6):399-411 (2004).
Schwarze et al., "In vivo protein transduction: delivery of a biologically active protein into the mouse," Science 285(5433):1569-1572 (1999).
Smith et al., "Comparison of biosequences," Advances in Applied Mathematics 2:482-489 (1981).
Smith et al., "Single-step purification of polypeptides expressed in *Escherichia coli* as fusions with glutathione S-transferase," Gene 67(1):31-40 (1988).
Thompson et al., "CLUSTAL W: improving the sensitivity of progressive multiple sequence alignment through sequence weighting position-specific gap penalties and weight matrix choice," Nucleic Acid Res. 22:4673-4680 (1994).
Tracey et al., "From mouse to man: or what have we learned about cytokine-based anti-inflammatory therapies?" Shock 11(3):224-225 (1999).
Written Opinion for International Application No. PCT/EP2013/055326, dated Jul. 19, 2013 (6 pages).
Written Opinion for International Application No. PCT/EP2013/055327, dated Oct. 9, 2013 (6 pages).
Written Opinion for International Application No. PCT/KR2013/008438, dated Dec. 23, 2013 (9 pages).
Yankner et al., "Neurotrophic and neurotoxic effects of amyloid beta protein: reversal by tachykinin neuropeptides," Science 250(4978):279-282 (1990).

HMGB1

Pep 36(μM)    0    0    1    10    50
20μM β-Amyloid    0    +    +    +    +

HMGB1

Pep 37(μM)    0    0    1    10    50
20μM β-Amyloid    0    +    +    +    +

HMGB1

Pep 70(μM)   0   0   1   10   50
20μM β-Amyloid   0   +   +   +   +

HMGB1

Pep 71(μM)   0   0   1   10   50
20μM β-Amyloid   0   +   +   +   +

FIG.87
HMGB1
Pep 110 (μM)    0    0    1    10    50
20μM β-Amyloid  0    +    +    +    +
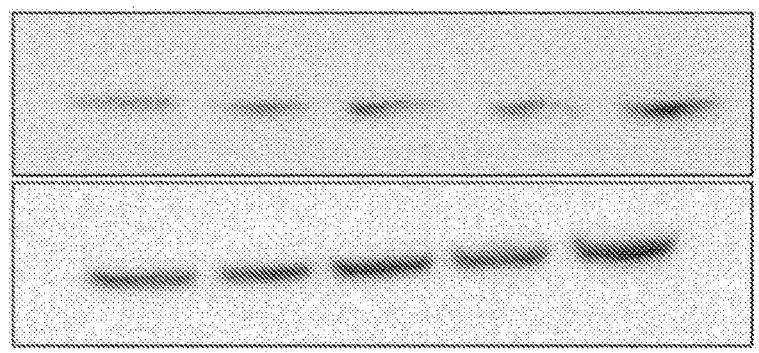
HMGB1
Pep 111 (μM)    0    0    1    10    50
20μM β-Amyloid  0    +    +    +    +
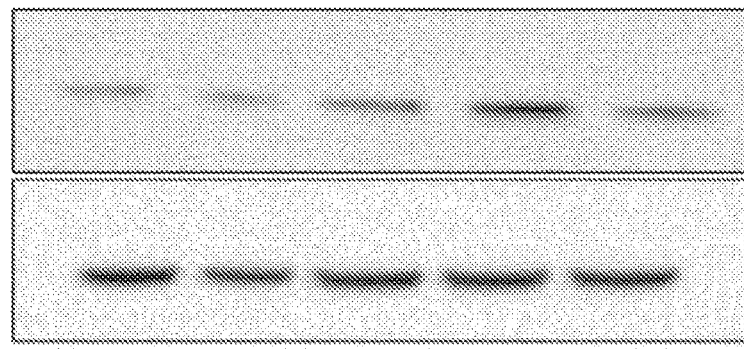
FIG.88

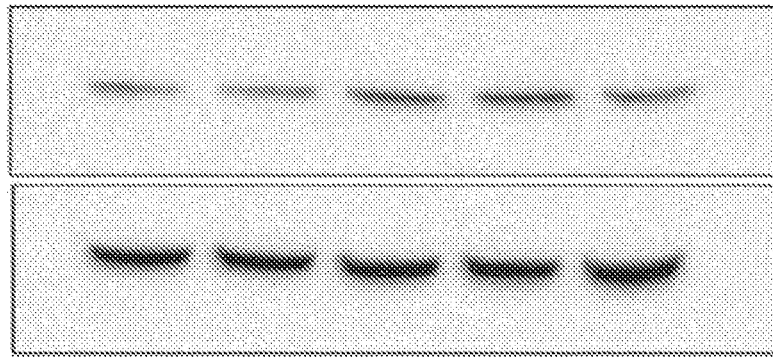
FIG.89
FIG.90

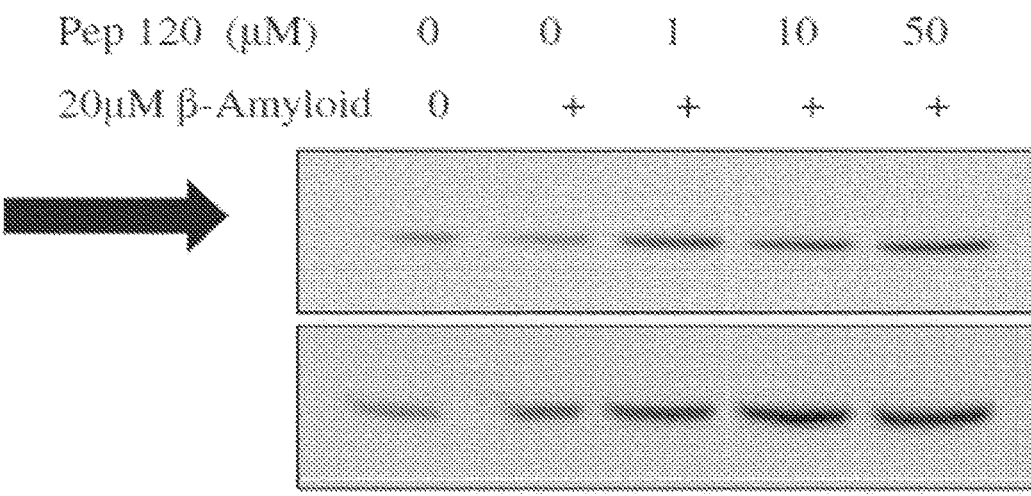
FIG.93
FIG.94
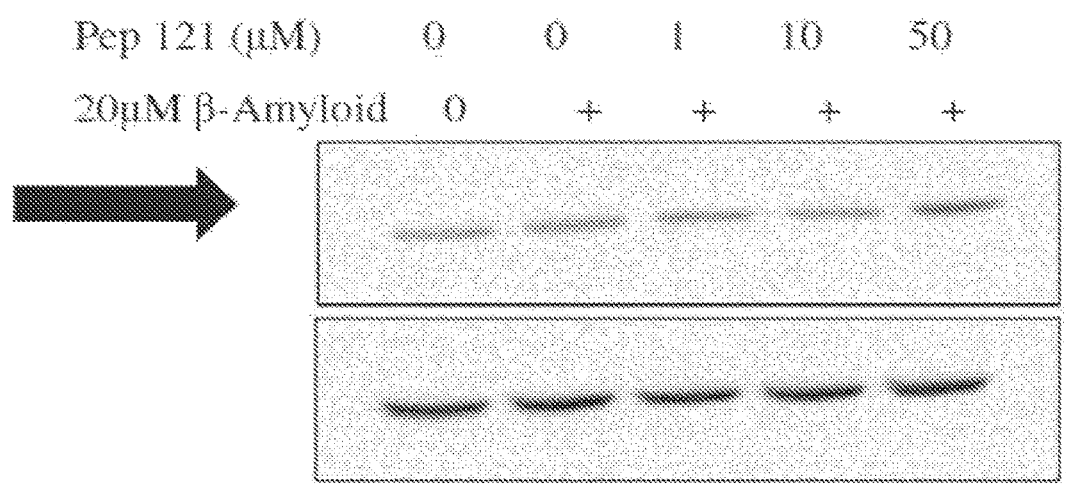

SEQUENCE LISTING

<160> NUMBER OF SEQ ID NOS: 163

<210> SEQ ID NO 1
<211> LENGTH: 30
<212> TYPE: PRT
<213> ORGANISM: Homo sapiens

<400> SEQUENCE: 1

Ala Leu Phe Ser Val Leu Asn Tyr Glu Arg Ala Arg Arg Pro Gly Leu
1               5                   10                  15

Leu Gly Ala Ser Val Leu Gly Leu Asp Asp Ile His Arg Ala
            20                  25                  30

<210> SEQ ID NO 2
<211> LENGTH: 15
<212> TYPE: PRT
<213> ORGANISM: Homo sapiens

<400> SEQUENCE: 2

Ser Val Leu Asn Tyr Glu Arg Ala Arg Arg Pro Gly Leu Leu Gly
1               5                   10                  15

<210> SEQ ID NO 3
<211> LENGTH: 10
<212> TYPE: PRT
<213> ORGANISM: Homo sapiens

<400> SEQUENCE: 3

Gly Leu Leu Gly Ala Ser Val Leu Gly Leu
1               5                   10

<210> SEQ ID NO 4
<211> LENGTH: 10
<212> TYPE: PRT
<213> ORGANISM: Homo sapiens

<400> SEQUENCE: 4

Ala Leu Leu Thr Ser Arg Leu Arg Phe Ile
1               5                   10

<210> SEQ ID NO 5
<211> LENGTH: 9
<212> TYPE: PRT
<213> ORGANISM: Homo sapiens

<400> SEQUENCE: 5

Arg Pro Ala Leu Leu Thr Ser Arg Leu
1               5

<210> SEQ ID NO 6
<211> LENGTH: 9
<212> TYPE: PRT
<213> ORGANISM: Homo sapiens

<400> SEQUENCE: 6

Arg Leu Thr Ser Arg Val Lys Ala Leu
1               5

<210> SEQ ID NO 7
<211> LENGTH: 15
<212> TYPE: PRT
<213> ORGANISM: Homo sapiens

<400> SEQUENCE: 7

```
Arg Thr Phe Val Leu Arg Val Arg Ala Gln Asp Pro Pro Glu
1               5                  10                  15
```

<210> SEQ ID NO 8
<211> LENGTH: 15
<212> TYPE: PRT
<213> ORGANISM: Homo sapiens

<400> SEQUENCE: 8

```
Arg Leu Thr Ser Arg Val Lys Ala Leu Phe Ser Val Leu Asn Tyr
1               5                  10                  15
```

<210> SEQ ID NO 9
<211> LENGTH: 15
<212> TYPE: PRT
<213> ORGANISM: Homo sapiens

<400> SEQUENCE: 9

```
Ala Glu Arg Leu Thr Ser Arg Val Lys Ala Leu Phe Ser Val Leu
1               5                  10                  15
```

<210> SEQ ID NO 10
<211> LENGTH: 9
<212> TYPE: PRT
<213> ORGANISM: Homo sapiens

<400> SEQUENCE: 10

```
Tyr Glu Arg Ala Arg Arg Pro Gly Leu
1               5
```

<210> SEQ ID NO 11
<211> LENGTH: 9
<212> TYPE: PRT
<213> ORGANISM: Homo sapiens

<400> SEQUENCE: 11

```
Leu Leu Gly Ala Ser Val Leu Gly Leu
1               5
```

<210> SEQ ID NO 12
<211> LENGTH: 10
<212> TYPE: PRT
<213> ORGANISM: Homo sapiens

<400> SEQUENCE: 12

```
Val Leu Gly Leu Asp Asp Ile His Arg Ala
1               5                  10
```

<210> SEQ ID NO 13
<211> LENGTH: 10
<212> TYPE: PRT
<213> ORGANISM: Homo sapiens

<400> SEQUENCE: 13

```
Gly Ala Ser Val Leu Gly Leu Asp Asp Ile
1               5                  10
```

<210> SEQ ID NO 14
<211> LENGTH: 10
<212> TYPE: PRT
<213> ORGANISM: Homo sapiens

<400> SEQUENCE: 14

```
Ala Leu Phe Ser Val Leu Asn Tyr Glu Arg
1               5                  10
```

<210> SEQ ID NO 15
<211> LENGTH: 10
<212> TYPE: PRT
<213> ORGANISM: Homo sapiens

<400> SEQUENCE: 15

Ser Val Leu Asn Tyr Glu Arg Ala Arg Arg
1               5                   10

<210> SEQ ID NO 16
<211> LENGTH: 10
<212> TYPE: PRT
<213> ORGANISM: Homo sapiens

<400> SEQUENCE: 16

Ser Val Leu Gly Leu Asp Asp Ile His Arg
1               5                   10

<210> SEQ ID NO 17
<211> LENGTH: 10
<212> TYPE: PRT
<213> ORGANISM: Homo sapiens

<400> SEQUENCE: 17

Phe Ser Val Leu Asn Tyr Glu Arg Ala Arg
1               5                   10

<210> SEQ ID NO 18
<211> LENGTH: 10
<212> TYPE: PRT
<213> ORGANISM: Homo sapiens

<400> SEQUENCE: 18

Asn Tyr Glu Arg Ala Arg Arg Pro Gly Leu
1               5                   10

<210> SEQ ID NO 19
<211> LENGTH: 10
<212> TYPE: PRT
<213> ORGANISM: Homo sapiens

<400> SEQUENCE: 19

Tyr Glu Arg Ala Arg Arg Pro Gly Leu Leu
1               5                   10

<210> SEQ ID NO 20
<211> LENGTH: 10
<212> TYPE: PRT
<213> ORGANISM: Homo sapiens

<400> SEQUENCE: 20

Arg Pro Gly Leu Leu Gly Ala Ser Val Leu
1               5                   10

<210> SEQ ID NO 21
<211> LENGTH: 9
<212> TYPE: PRT
<213> ORGANISM: Homo sapiens

<400> SEQUENCE: 21

Glu Arg Ala Arg Arg Pro Gly Leu Leu
1               5

```
<210> SEQ ID NO 22
<211> LENGTH: 9
<212> TYPE: PRT
<213> ORGANISM: Homo sapiens

<400> SEQUENCE: 22

Val Leu Gly Leu Asp Asp Ile His Arg
1               5

<210> SEQ ID NO 23
<211> LENGTH: 9
<212> TYPE: PRT
<213> ORGANISM: Homo sapiens

<400> SEQUENCE: 23

Ser Val Leu Asn Tyr Glu Arg Ala Arg
1               5

<210> SEQ ID NO 24
<211> LENGTH: 9
<212> TYPE: PRT
<213> ORGANISM: Homo sapiens

<400> SEQUENCE: 24

Val Leu Asn Tyr Glu Arg Ala Arg Arg
1               5

<210> SEQ ID NO 25
<211> LENGTH: 9
<212> TYPE: PRT
<213> ORGANISM: Homo sapiens

<400> SEQUENCE: 25

Ala Arg Arg Pro Gly Leu Leu Gly Ala
1               5

<210> SEQ ID NO 26
<211> LENGTH: 9
<212> TYPE: PRT
<213> ORGANISM: Homo sapiens

<400> SEQUENCE: 26

Pro Gly Leu Leu Gly Ala Ser Val Leu
1               5

<210> SEQ ID NO 27
<211> LENGTH: 9
<212> TYPE: PRT
<213> ORGANISM: Homo sapiens

<400> SEQUENCE: 27

Arg Arg Pro Gly Leu Leu Gly Ala Ser
1               5

<210> SEQ ID NO 28
<211> LENGTH: 9
<212> TYPE: PRT
<213> ORGANISM: Homo sapiens

<400> SEQUENCE: 28

Ala Leu Phe Ser Val Leu Asn Tyr Glu
1               5

<210> SEQ ID NO 29
<211> LENGTH: 9
```

```
<212> TYPE: PRT
<213> ORGANISM: Homo sapiens

<400> SEQUENCE: 29

Gly Leu Leu Gly Ala Ser Val Leu Gly
1               5

<210> SEQ ID NO 30
<211> LENGTH: 9
<212> TYPE: PRT
<213> ORGANISM: Homo sapiens

<400> SEQUENCE: 30

Ser Val Leu Gly Leu Asp Asp Ile His
1               5

<210> SEQ ID NO 31
<211> LENGTH: 8
<212> TYPE: PRT
<213> ORGANISM: Homo sapiens

<400> SEQUENCE: 31

Glu Arg Ala Arg Arg Pro Gly Leu
1               5

<210> SEQ ID NO 32
<211> LENGTH: 8
<212> TYPE: PRT
<213> ORGANISM: Homo sapiens

<400> SEQUENCE: 32

Ala Arg Arg Pro Gly Leu Leu Gly
1               5

<210> SEQ ID NO 33
<211> LENGTH: 8
<212> TYPE: PRT
<213> ORGANISM: Homo sapiens

<400> SEQUENCE: 33

Gly Leu Leu Gly Ala Ser Val Leu
1               5

<210> SEQ ID NO 34
<211> LENGTH: 8
<212> TYPE: PRT
<213> ORGANISM: Homo sapiens

<400> SEQUENCE: 34

Arg Ala Arg Arg Pro Gly Leu Leu
1               5

<210> SEQ ID NO 35
<211> LENGTH: 8
<212> TYPE: PRT
<213> ORGANISM: Homo sapiens

<400> SEQUENCE: 35

Leu Gly Ala Ser Val Leu Gly Leu
1               5

<210> SEQ ID NO 36
<211> LENGTH: 15
<212> TYPE: PRT
<213> ORGANISM: Homo sapiens
```

<400> SEQUENCE: 36

Val Thr Glu Thr Thr Phe Gln Lys Asn Arg Leu Phe Phe Tyr Arg
1               5                   10                  15

<210> SEQ ID NO 37
<211> LENGTH: 15
<212> TYPE: PRT
<213> ORGANISM: Homo sapiens

<400> SEQUENCE: 37

Leu Phe Phe Tyr Arg Lys Ser Val Trp Ser Lys Leu Gln Ser Ile
1               5                   10                  15

<210> SEQ ID NO 38
<211> LENGTH: 15
<212> TYPE: PRT
<213> ORGANISM: Homo sapiens

<400> SEQUENCE: 38

Lys Leu Gln Ser Ile Gly Ile Arg Gln His Leu Lys Arg Val Gln
1               5                   10                  15

<210> SEQ ID NO 39
<211> LENGTH: 15
<212> TYPE: PRT
<213> ORGANISM: Homo sapiens

<400> SEQUENCE: 39

Glu Ala Glu Val Arg Gln His Arg Glu Ala Arg Pro Ala Leu Leu
1               5                   10                  15

<210> SEQ ID NO 40
<211> LENGTH: 15
<212> TYPE: PRT
<213> ORGANISM: Homo sapiens

<400> SEQUENCE: 40

Arg Pro Ala Leu Leu Thr Ser Arg Leu Arg Phe Ile Pro Lys Pro
1               5                   10                  15

<210> SEQ ID NO 41
<211> LENGTH: 15
<212> TYPE: PRT
<213> ORGANISM: Homo sapiens

<400> SEQUENCE: 41

Phe Ile Pro Lys Pro Asp Gly Leu Arg Pro Ile Val Asn Met Asp
1               5                   10                  15

<210> SEQ ID NO 42
<211> LENGTH: 15
<212> TYPE: PRT
<213> ORGANISM: Homo sapiens

<400> SEQUENCE: 42

Arg Thr Phe Arg Arg Glu Lys Arg Ala Glu Arg Leu Thr Ser Arg
1               5                   10                  15

<210> SEQ ID NO 43
<211> LENGTH: 15
<212> TYPE: PRT
<213> ORGANISM: Homo sapiens

<400> SEQUENCE: 43

```
Leu Asp Asp Ile His Arg Ala Trp Arg Thr Phe Val Leu Arg Val
1               5                   10                  15

<210> SEQ ID NO 44
<211> LENGTH: 15
<212> TYPE: PRT
<213> ORGANISM: Homo sapiens

<400> SEQUENCE: 44

Phe Val Leu Arg Val Arg Ala Gln Asp Pro Pro Pro Glu Leu Tyr
1               5                   10                  15

<210> SEQ ID NO 45
<211> LENGTH: 15
<212> TYPE: PRT
<213> ORGANISM: Homo sapiens

<400> SEQUENCE: 45

Pro Gln Asp Arg Leu Thr Glu Val Ile Ala Ser Ile Ile Lys Pro
1               5                   10                  15

<210> SEQ ID NO 46
<211> LENGTH: 15
<212> TYPE: PRT
<213> ORGANISM: Homo sapiens

<400> SEQUENCE: 46

Lys Ser Val Trp Ser Lys Leu Gln Ser Ile Gly Ile Arg Gln His
1               5                   10                  15

<210> SEQ ID NO 47
<211> LENGTH: 16
<212> TYPE: PRT
<213> ORGANISM: Homo sapiens

<400> SEQUENCE: 47

Leu Lys Arg Val Gln Leu Arg Glu Leu Ser Glu Ala Glu Val Arg Gln
1               5                   10                  15

<210> SEQ ID NO 48
<211> LENGTH: 20
<212> TYPE: PRT
<213> ORGANISM: Homo sapiens

<400> SEQUENCE: 48

Met Pro Arg Ala Pro Arg Cys Arg Ala Val Arg Ser Leu Leu Arg Ser
1               5                   10                  15

His Tyr Arg Glu
            20

<210> SEQ ID NO 49
<211> LENGTH: 20
<212> TYPE: PRT
<213> ORGANISM: Homo sapiens

<400> SEQUENCE: 49

Val Leu Pro Leu Ala Thr Phe Val Arg Arg Leu Gly Pro Gln Gly Trp
1               5                   10                  15

Arg Leu Val Gln
            20

<210> SEQ ID NO 50
<211> LENGTH: 20
```

-continued

```
<212> TYPE: PRT
<213> ORGANISM: Homo sapiens

<400> SEQUENCE: 50

Arg Gly Asp Pro Ala Ala Phe Arg Ala Leu Val Ala Gln Cys Leu Val
1               5                   10                  15

Cys Val Pro Trp
            20

<210> SEQ ID NO 51
<211> LENGTH: 20
<212> TYPE: PRT
<213> ORGANISM: Homo sapiens

<400> SEQUENCE: 51

Asp Ala Arg Pro Pro Ala Ala Pro Ser Phe Arg Gln Val Ser Cys
1               5                   10                  15

Leu Lys Glu Leu
            20

<210> SEQ ID NO 52
<211> LENGTH: 20
<212> TYPE: PRT
<213> ORGANISM: Homo sapiens

<400> SEQUENCE: 52

Val Ala Arg Val Leu Gln Arg Leu Cys Glu Arg Gly Ala Lys Asn Val
1               5                   10                  15

Leu Ala Phe Gly
            20

<210> SEQ ID NO 53
<211> LENGTH: 20
<212> TYPE: PRT
<213> ORGANISM: Homo sapiens

<400> SEQUENCE: 53

Phe Ala Leu Leu Asp Gly Ala Arg Gly Gly Pro Pro Glu Ala Phe Thr
1               5                   10                  15

Thr Ser Val Arg
            20

<210> SEQ ID NO 54
<211> LENGTH: 20
<212> TYPE: PRT
<213> ORGANISM: Homo sapiens

<400> SEQUENCE: 54

Ser Tyr Leu Pro Asn Thr Val Thr Asp Ala Leu Arg Gly Ser Gly Ala
1               5                   10                  15

Trp Gly Leu Leu
            20

<210> SEQ ID NO 55
<211> LENGTH: 20
<212> TYPE: PRT
<213> ORGANISM: Homo sapiens

<400> SEQUENCE: 55

Leu Arg Arg Val Gly Asp Asp Val Leu Val His Leu Leu Ala Arg Cys
1               5                   10                  15

Ala Leu Phe Val
```

20

<210> SEQ ID NO 56
<211> LENGTH: 20
<212> TYPE: PRT
<213> ORGANISM: Homo sapiens

<400> SEQUENCE: 56

Leu Val Ala Pro Ser Cys Ala Tyr Gln Val Cys Gly Pro Pro Leu Tyr
1               5                   10                  15

Gln Leu Gly Ala
            20

<210> SEQ ID NO 57
<211> LENGTH: 20
<212> TYPE: PRT
<213> ORGANISM: Homo sapiens

<400> SEQUENCE: 57

Ala Thr Gln Ala Arg Pro Pro His Ala Ser Gly Pro Arg Arg Arg
1               5                   10                  15

Leu Gly Cys Glu
            20

<210> SEQ ID NO 58
<211> LENGTH: 20
<212> TYPE: PRT
<213> ORGANISM: Homo sapiens

<400> SEQUENCE: 58

Arg Ala Trp Asn His Ser Val Arg Glu Ala Gly Val Pro Leu Gly Leu
1               5                   10                  15

Pro Ala Pro Gly
            20

<210> SEQ ID NO 59
<211> LENGTH: 20
<212> TYPE: PRT
<213> ORGANISM: Homo sapiens

<400> SEQUENCE: 59

Ala Arg Arg Arg Gly Gly Ser Ala Ser Arg Ser Leu Pro Leu Pro Lys
1               5                   10                  15

Arg Pro Arg Arg
            20

<210> SEQ ID NO 60
<211> LENGTH: 20
<212> TYPE: PRT
<213> ORGANISM: Homo sapiens

<400> SEQUENCE: 60

Gly Ala Ala Pro Glu Pro Glu Arg Thr Pro Val Gly Gln Gly Ser Trp
1               5                   10                  15

Ala His Pro Gly
            20

<210> SEQ ID NO 61
<211> LENGTH: 20
<212> TYPE: PRT
<213> ORGANISM: Homo sapiens

<400> SEQUENCE: 61

-continued

Arg Thr Arg Gly Pro Ser Asp Arg Gly Phe Cys Val Val Ser Pro Ala
1               5                   10                  15

Arg Pro Ala Glu
            20

<210> SEQ ID NO 62
<211> LENGTH: 20
<212> TYPE: PRT
<213> ORGANISM: Homo sapiens

<400> SEQUENCE: 62

Glu Ala Thr Ser Leu Glu Gly Ala Leu Ser Gly Thr Arg His Ser His
1               5                   10                  15

Pro Ser Val Gly
            20

<210> SEQ ID NO 63
<211> LENGTH: 20
<212> TYPE: PRT
<213> ORGANISM: Homo sapiens

<400> SEQUENCE: 63

Arg Gln His His Ala Gly Pro Pro Ser Thr Ser Arg Pro Pro Arg Pro
1               5                   10                  15

Trp Asp Thr Pro
            20

<210> SEQ ID NO 64
<211> LENGTH: 20
<212> TYPE: PRT
<213> ORGANISM: Homo sapiens

<400> SEQUENCE: 64

Cys Pro Pro Val Tyr Ala Glu Thr Lys His Phe Leu Tyr Ser Ser Gly
1               5                   10                  15

Asp Lys Glu Gln
            20

<210> SEQ ID NO 65
<211> LENGTH: 20
<212> TYPE: PRT
<213> ORGANISM: Homo sapiens

<400> SEQUENCE: 65

Leu Arg Pro Ser Phe Leu Leu Ser Ser Leu Arg Pro Ser Leu Thr Gly
1               5                   10                  15

Ala Arg Arg Leu
            20

<210> SEQ ID NO 66
<211> LENGTH: 20
<212> TYPE: PRT
<213> ORGANISM: Homo sapiens

<400> SEQUENCE: 66

Val Glu Thr Ile Phe Leu Gly Ser Arg Pro Trp Met Pro Gly Thr Pro
1               5                   10                  15

Arg Arg Leu Pro
            20

<210> SEQ ID NO 67

```
<211> LENGTH: 20
<212> TYPE: PRT
<213> ORGANISM: Homo sapiens

<400> SEQUENCE: 67

Arg Leu Pro Gln Arg Tyr Trp Gln Met Arg Pro Leu Phe Leu Glu Leu
1               5                   10                  15

Leu Gly Asn His
            20

<210> SEQ ID NO 68
<211> LENGTH: 20
<212> TYPE: PRT
<213> ORGANISM: Homo sapiens

<400> SEQUENCE: 68

Ala Gln Cys Pro Tyr Gly Val Leu Leu Lys Thr His Cys Pro Leu Arg
1               5                   10                  15

Ala Ala Val Thr
            20

<210> SEQ ID NO 69
<211> LENGTH: 20
<212> TYPE: PRT
<213> ORGANISM: Homo sapiens

<400> SEQUENCE: 69

Pro Ala Ala Gly Val Cys Ala Arg Glu Lys Pro Gln Gly Ser Val Ala
1               5                   10                  15

Ala Pro Glu Glu
            20

<210> SEQ ID NO 70
<211> LENGTH: 20
<212> TYPE: PRT
<213> ORGANISM: Homo sapiens

<400> SEQUENCE: 70

Glu Asp Thr Asp Pro Arg Arg Leu Val Gln Leu Leu Arg Gln His Ser
1               5                   10                  15

Ser Pro Trp Gln
            20

<210> SEQ ID NO 71
<211> LENGTH: 20
<212> TYPE: PRT
<213> ORGANISM: Homo sapiens

<400> SEQUENCE: 71

Val Tyr Gly Phe Val Arg Ala Cys Leu Arg Arg Leu Val Pro Pro Gly
1               5                   10                  15

Leu Trp Gly Ser
            20

<210> SEQ ID NO 72
<211> LENGTH: 20
<212> TYPE: PRT
<213> ORGANISM: Homo sapiens

<400> SEQUENCE: 72

Arg His Asn Glu Arg Arg Phe Leu Arg Asn Thr Lys Lys Phe Ile Ser
1               5                   10                  15
```

Leu Gly Lys His
        20

<210> SEQ ID NO 73
<211> LENGTH: 20
<212> TYPE: PRT
<213> ORGANISM: Homo sapiens

<400> SEQUENCE: 73

Ala Lys Leu Ser Leu Gln Glu Leu Thr Trp Lys Met Ser Val Arg Asp
1               5                   10                  15

Cys Ala Trp Leu
        20

<210> SEQ ID NO 74
<211> LENGTH: 20
<212> TYPE: PRT
<213> ORGANISM: Homo sapiens

<400> SEQUENCE: 74

Arg Arg Ser Pro Gly Val Gly Cys Val Pro Ala Ala Glu His Arg Leu
1               5                   10                  15

Arg Glu Glu Ile
        20

<210> SEQ ID NO 75
<211> LENGTH: 20
<212> TYPE: PRT
<213> ORGANISM: Homo sapiens

<400> SEQUENCE: 75

Leu Ala Lys Phe Leu His Trp Leu Met Ser Val Tyr Val Val Glu Leu
1               5                   10                  15

Leu Arg Ser Phe
        20

<210> SEQ ID NO 76
<211> LENGTH: 20
<212> TYPE: PRT
<213> ORGANISM: Homo sapiens

<400> SEQUENCE: 76

Phe Tyr Val Thr Glu Thr Thr Phe Gln Lys Asn Arg Leu Phe Phe Tyr
1               5                   10                  15

Arg Lys Ser Val
        20

<210> SEQ ID NO 77
<211> LENGTH: 20
<212> TYPE: PRT
<213> ORGANISM: Homo sapiens

<400> SEQUENCE: 77

Trp Ser Lys Leu Gln Ser Ile Gly Ile Arg Gln His Leu Lys Arg Val
1               5                   10                  15

Gln Leu Arg Glu
        20

<210> SEQ ID NO 78
<211> LENGTH: 20
<212> TYPE: PRT
<213> ORGANISM: Homo sapiens

```
<400> SEQUENCE: 78

Leu Ser Glu Ala Glu Val Arg Gln His Arg Glu Ala Arg Pro Ala Leu
1               5                   10                  15

Leu Thr Ser Arg
            20

<210> SEQ ID NO 79
<211> LENGTH: 20
<212> TYPE: PRT
<213> ORGANISM: Homo sapiens

<400> SEQUENCE: 79

Leu Arg Phe Ile Pro Lys Pro Asp Gly Leu Arg Pro Ile Val Asn Met
1               5                   10                  15

Asp Tyr Val Val
            20

<210> SEQ ID NO 80
<211> LENGTH: 20
<212> TYPE: PRT
<213> ORGANISM: Homo sapiens

<400> SEQUENCE: 80

Gly Ala Arg Thr Phe Arg Arg Glu Lys Arg Ala Glu Arg Leu Thr Ser
1               5                   10                  15

Arg Val Lys Ala
            20

<210> SEQ ID NO 81
<211> LENGTH: 20
<212> TYPE: PRT
<213> ORGANISM: Homo sapiens

<400> SEQUENCE: 81

Leu Phe Ser Val Leu Asn Tyr Glu Arg Ala Arg Arg Pro Gly Leu Leu
1               5                   10                  15

Gly Ala Ser Val
            20

<210> SEQ ID NO 82
<211> LENGTH: 20
<212> TYPE: PRT
<213> ORGANISM: Homo sapiens

<400> SEQUENCE: 82

Leu Gly Leu Asp Asp Ile His Arg Ala Trp Arg Thr Phe Val Leu Arg
1               5                   10                  15

Val Arg Ala Gln
            20

<210> SEQ ID NO 83
<211> LENGTH: 20
<212> TYPE: PRT
<213> ORGANISM: Homo sapiens

<400> SEQUENCE: 83

Asp Pro Pro Pro Glu Leu Tyr Phe Val Lys Val Asp Thr Gly Ala
1               5                   10                  15

Tyr Asp Thr Ile
            20
```

```
<210> SEQ ID NO 84
<211> LENGTH: 20
<212> TYPE: PRT
<213> ORGANISM: Homo sapiens

<400> SEQUENCE: 84

Pro Gln Asp Arg Leu Thr Glu Val Ile Ala Ser Ile Ile Lys Pro Gln
1               5                   10                  15

Asn Thr Tyr Cys
            20

<210> SEQ ID NO 85
<211> LENGTH: 20
<212> TYPE: PRT
<213> ORGANISM: Homo sapiens

<400> SEQUENCE: 85

Val Arg Arg Tyr Ala Val Val Gln Lys Ala Ala His Gly His Val Arg
1               5                   10                  15

Lys Ala Phe Lys
            20

<210> SEQ ID NO 86
<211> LENGTH: 20
<212> TYPE: PRT
<213> ORGANISM: Homo sapiens

<400> SEQUENCE: 86

Ser His Val Ser Thr Leu Thr Asp Leu Gln Pro Tyr Met Arg Gln Phe
1               5                   10                  15

Val Ala His Leu
            20

<210> SEQ ID NO 87
<211> LENGTH: 20
<212> TYPE: PRT
<213> ORGANISM: Homo sapiens

<400> SEQUENCE: 87

Gln Glu Thr Ser Pro Leu Arg Asp Ala Val Val Ile Glu Gln Ser Ser
1               5                   10                  15

Ser Leu Asn Glu
            20

<210> SEQ ID NO 88
<211> LENGTH: 20
<212> TYPE: PRT
<213> ORGANISM: Homo sapiens

<400> SEQUENCE: 88

Ala Ser Ser Gly Leu Phe Asp Val Phe Leu Arg Phe Met Cys His His
1               5                   10                  15

Ala Val Arg Ile
            20

<210> SEQ ID NO 89
<211> LENGTH: 20
<212> TYPE: PRT
<213> ORGANISM: Homo sapiens

<400> SEQUENCE: 89

Arg Gly Lys Ser Tyr Val Gln Cys Gln Gly Ile Pro Gln Gly Ser Ile
1               5                   10                  15
```

Leu Ser Thr Leu
        20

<210> SEQ ID NO 90
<211> LENGTH: 20
<212> TYPE: PRT
<213> ORGANISM: Homo sapiens

<400> SEQUENCE: 90

Leu Cys Ser Leu Cys Tyr Gly Asp Met Glu Asn Lys Leu Phe Ala Gly
1               5                   10                  15

Ile Arg Arg Asp
        20

<210> SEQ ID NO 91
<211> LENGTH: 20
<212> TYPE: PRT
<213> ORGANISM: Homo sapiens

<400> SEQUENCE: 91

Gly Leu Leu Leu Arg Leu Val Asp Asp Phe Leu Leu Val Thr Pro His
1               5                   10                  15

Leu Thr His Ala
        20

<210> SEQ ID NO 92
<211> LENGTH: 20
<212> TYPE: PRT
<213> ORGANISM: Homo sapiens

<400> SEQUENCE: 92

Lys Thr Phe Leu Arg Thr Leu Val Arg Gly Val Pro Glu Tyr Gly Cys
1               5                   10                  15

Val Val Asn Leu
        20

<210> SEQ ID NO 93
<211> LENGTH: 20
<212> TYPE: PRT
<213> ORGANISM: Homo sapiens

<400> SEQUENCE: 93

Arg Lys Thr Val Val Asn Phe Pro Val Glu Asp Glu Ala Leu Gly Gly
1               5                   10                  15

Thr Ala Phe Val
        20

<210> SEQ ID NO 94
<211> LENGTH: 20
<212> TYPE: PRT
<213> ORGANISM: Homo sapiens

<400> SEQUENCE: 94

Gln Met Pro Ala His Gly Leu Phe Pro Trp Cys Gly Leu Leu Leu Asp
1               5                   10                  15

Thr Arg Thr Leu
        20

<210> SEQ ID NO 95
<211> LENGTH: 20
<212> TYPE: PRT
<213> ORGANISM: Homo sapiens

```
<400> SEQUENCE: 95

Glu Val Gln Ser Asp Tyr Ser Ser Tyr Ala Arg Thr Ser Ile Arg Ala
1               5                   10                  15

Ser Leu Thr Phe
            20

<210> SEQ ID NO 96
<211> LENGTH: 20
<212> TYPE: PRT
<213> ORGANISM: Homo sapiens

<400> SEQUENCE: 96

Asn Arg Gly Phe Lys Ala Gly Arg Asn Met Arg Arg Lys Leu Phe Gly
1               5                   10                  15

Val Leu Arg Leu
            20

<210> SEQ ID NO 97
<211> LENGTH: 20
<212> TYPE: PRT
<213> ORGANISM: Homo sapiens

<400> SEQUENCE: 97

Lys Cys His Ser Leu Phe Leu Asp Leu Gln Val Asn Ser Leu Gln Thr
1               5                   10                  15

Val Cys Thr Asn
            20

<210> SEQ ID NO 98
<211> LENGTH: 20
<212> TYPE: PRT
<213> ORGANISM: Homo sapiens

<400> SEQUENCE: 98

Ile Tyr Lys Ile Leu Leu Leu Gln Ala Tyr Arg Phe His Ala Cys Val
1               5                   10                  15

Leu Gln Leu Pro
            20

<210> SEQ ID NO 99
<211> LENGTH: 20
<212> TYPE: PRT
<213> ORGANISM: Homo sapiens

<400> SEQUENCE: 99

Phe His Gln Gln Val Trp Lys Asn Pro Thr Phe Phe Leu Arg Val Ile
1               5                   10                  15

Ser Asp Thr Ala
            20

<210> SEQ ID NO 100
<211> LENGTH: 20
<212> TYPE: PRT
<213> ORGANISM: Homo sapiens

<400> SEQUENCE: 100

Ser Leu Cys Tyr Ser Ile Leu Lys Ala Lys Asn Ala Gly Met Ser Leu
1               5                   10                  15

Gly Ala Lys Gly
            20
```

```
<210> SEQ ID NO 101
<211> LENGTH: 20
<212> TYPE: PRT
<213> ORGANISM: Homo sapiens

<400> SEQUENCE: 101

Ala Ala Gly Pro Leu Pro Ser Glu Ala Val Gln Trp Leu Cys His Gln
1               5                   10                  15

Ala Phe Leu Leu
            20

<210> SEQ ID NO 102
<211> LENGTH: 20
<212> TYPE: PRT
<213> ORGANISM: Homo sapiens

<400> SEQUENCE: 102

Lys Leu Thr Arg His Arg Val Thr Tyr Val Pro Leu Leu Gly Ser Leu
1               5                   10                  15

Arg Thr Ala Gln
            20

<210> SEQ ID NO 103
<211> LENGTH: 20
<212> TYPE: PRT
<213> ORGANISM: Homo sapiens

<400> SEQUENCE: 103

Thr Gln Leu Ser Arg Lys Leu Pro Gly Thr Thr Leu Thr Ala Leu Glu
1               5                   10                  15

Ala Ala Ala Asn
            20

<210> SEQ ID NO 104
<211> LENGTH: 12
<212> TYPE: PRT
<213> ORGANISM: Homo sapiens

<400> SEQUENCE: 104

Pro Ala Leu Pro Ser Asp Phe Lys Thr Ile Leu Asp
1               5                   10

<210> SEQ ID NO 105
<211> LENGTH: 10
<212> TYPE: PRT
<213> ORGANISM: Homo sapiens

<400> SEQUENCE: 105

Met Pro Arg Ala Pro Arg Cys Arg Ala Val
1               5                   10

<210> SEQ ID NO 106
<211> LENGTH: 20
<212> TYPE: PRT
<213> ORGANISM: Homo sapiens

<400> SEQUENCE: 106

Arg Ser Leu Leu Arg Ser His Tyr Arg Glu Val Leu Pro Leu Ala Thr
1               5                   10                  15

Phe Val Arg Arg
            20
```

```
<210> SEQ ID NO 107
<211> LENGTH: 20
<212> TYPE: PRT
<213> ORGANISM: Homo sapiens

<400> SEQUENCE: 107

Leu Gly Pro Gln Gly Trp Arg Leu Val Gln Arg Gly Asp Pro Ala Ala
1               5                   10                  15

Phe Arg Ala Leu
            20

<210> SEQ ID NO 108
<211> LENGTH: 20
<212> TYPE: PRT
<213> ORGANISM: Homo sapiens

<400> SEQUENCE: 108

Val Ala Gln Cys Leu Val Cys Val Pro Trp Asp Ala Arg Pro Pro Pro
1               5                   10                  15

Ala Ala Pro Ser
            20

<210> SEQ ID NO 109
<211> LENGTH: 20
<212> TYPE: PRT
<213> ORGANISM: Homo sapiens

<400> SEQUENCE: 109

Phe Arg Gln Val Ser Cys Leu Lys Glu Leu Val Ala Arg Val Leu Gln
1               5                   10                  15

Arg Leu Cys Glu
            20

<210> SEQ ID NO 110
<211> LENGTH: 20
<212> TYPE: PRT
<213> ORGANISM: Homo sapiens

<400> SEQUENCE: 110

Arg Gly Ala Lys Asn Val Leu Ala Phe Gly Phe Ala Leu Leu Asp Gly
1               5                   10                  15

Ala Arg Gly Gly
            20

<210> SEQ ID NO 111
<211> LENGTH: 20
<212> TYPE: PRT
<213> ORGANISM: Homo sapiens

<400> SEQUENCE: 111

Pro Pro Glu Ala Phe Thr Thr Ser Val Arg Ser Tyr Leu Pro Asn Thr
1               5                   10                  15

Val Thr Asp Ala
            20

<210> SEQ ID NO 112
<211> LENGTH: 20
<212> TYPE: PRT
<213> ORGANISM: Homo sapiens

<400> SEQUENCE: 112

Leu Arg Gly Ser Gly Ala Trp Gly Leu Leu Leu Arg Arg Val Gly Asp
1               5                   10                  15
```

```
Asp Val Leu Val
        20

<210> SEQ ID NO 113
<211> LENGTH: 20
<212> TYPE: PRT
<213> ORGANISM: Homo sapiens

<400> SEQUENCE: 113

His Leu Leu Ala Arg Cys Ala Leu Phe Val Leu Val Ala Pro Ser Cys
1               5                   10                  15

Ala Tyr Gln Val
        20

<210> SEQ ID NO 114
<211> LENGTH: 20
<212> TYPE: PRT
<213> ORGANISM: Homo sapiens

<400> SEQUENCE: 114

Cys Gly Pro Pro Leu Tyr Gln Leu Gly Ala Ala Thr Gln Ala Arg Pro
1               5                   10                  15

Pro Pro His Ala
        20

<210> SEQ ID NO 115
<211> LENGTH: 20
<212> TYPE: PRT
<213> ORGANISM: Homo sapiens

<400> SEQUENCE: 115

Ser Gly Pro Arg Arg Arg Leu Gly Cys Glu Arg Ala Trp Asn His Ser
1               5                   10                  15

Val Arg Glu Ala
        20

<210> SEQ ID NO 116
<211> LENGTH: 20
<212> TYPE: PRT
<213> ORGANISM: Homo sapiens

<400> SEQUENCE: 116

Gly Val Pro Leu Gly Leu Pro Ala Pro Gly Ala Arg Arg Arg Gly Gly
1               5                   10                  15

Ser Ala Ser Arg
        20

<210> SEQ ID NO 117
<211> LENGTH: 20
<212> TYPE: PRT
<213> ORGANISM: Homo sapiens

<400> SEQUENCE: 117

Ser Leu Pro Leu Pro Lys Arg Pro Arg Arg Gly Ala Ala Pro Glu Pro
1               5                   10                  15

Glu Arg Thr Pro
        20

<210> SEQ ID NO 118
<211> LENGTH: 20
<212> TYPE: PRT
<213> ORGANISM: Homo sapiens
```

```
<400> SEQUENCE: 118

Val Gly Gln Gly Ser Trp Ala His Pro Gly Arg Thr Arg Gly Pro Ser
1               5                   10                  15

Asp Arg Gly Phe
            20

<210> SEQ ID NO 119
<211> LENGTH: 20
<212> TYPE: PRT
<213> ORGANISM: Homo sapiens

<400> SEQUENCE: 119

Cys Val Val Ser Pro Ala Arg Pro Ala Glu Glu Ala Thr Ser Leu Glu
1               5                   10                  15

Gly Ala Leu Ser
            20

<210> SEQ ID NO 120
<211> LENGTH: 20
<212> TYPE: PRT
<213> ORGANISM: Homo sapiens

<400> SEQUENCE: 120

Gly Thr Arg His Ser His Pro Ser Val Gly Arg Gln His His Ala Gly
1               5                   10                  15

Pro Pro Ser Thr
            20

<210> SEQ ID NO 121
<211> LENGTH: 20
<212> TYPE: PRT
<213> ORGANISM: Homo sapiens

<400> SEQUENCE: 121

Ser Arg Pro Pro Arg Pro Trp Asp Thr Pro Cys Pro Pro Val Tyr Ala
1               5                   10                  15

Glu Thr Lys His
            20

<210> SEQ ID NO 122
<211> LENGTH: 20
<212> TYPE: PRT
<213> ORGANISM: Homo sapiens

<400> SEQUENCE: 122

Phe Leu Tyr Ser Ser Gly Asp Lys Glu Gln Leu Arg Pro Ser Phe Leu
1               5                   10                  15

Leu Ser Ser Leu
            20

<210> SEQ ID NO 123
<211> LENGTH: 20
<212> TYPE: PRT
<213> ORGANISM: Homo sapiens

<400> SEQUENCE: 123

Arg Pro Ser Leu Thr Gly Ala Arg Arg Leu Val Glu Thr Ile Phe Leu
1               5                   10                  15

Gly Ser Arg Pro
            20
```

```
<210> SEQ ID NO 124
<211> LENGTH: 20
<212> TYPE: PRT
<213> ORGANISM: Homo sapiens

<400> SEQUENCE: 124

Trp Met Pro Gly Thr Pro Arg Arg Leu Pro Arg Leu Pro Gln Arg Tyr
1               5                   10                  15

Trp Gln Met Arg
            20

<210> SEQ ID NO 125
<211> LENGTH: 20
<212> TYPE: PRT
<213> ORGANISM: Homo sapiens

<400> SEQUENCE: 125

Pro Leu Phe Leu Glu Leu Leu Gly Asn His Ala Gln Cys Pro Tyr Gly
1               5                   10                  15

Val Leu Leu Lys
            20

<210> SEQ ID NO 126
<211> LENGTH: 20
<212> TYPE: PRT
<213> ORGANISM: Homo sapiens

<400> SEQUENCE: 126

Thr His Cys Pro Leu Arg Ala Ala Val Thr Pro Ala Ala Gly Val Cys
1               5                   10                  15

Ala Arg Glu Lys
            20

<210> SEQ ID NO 127
<211> LENGTH: 20
<212> TYPE: PRT
<213> ORGANISM: Homo sapiens

<400> SEQUENCE: 127

Pro Gln Gly Ser Val Ala Ala Pro Glu Glu Glu Asp Thr Asp Pro Arg
1               5                   10                  15

Arg Leu Val Gln
            20

<210> SEQ ID NO 128
<211> LENGTH: 20
<212> TYPE: PRT
<213> ORGANISM: Homo sapiens

<400> SEQUENCE: 128

Leu Leu Arg Gln His Ser Ser Pro Trp Gln Val Tyr Gly Phe Val Arg
1               5                   10                  15

Ala Cys Leu Arg
            20

<210> SEQ ID NO 129
<211> LENGTH: 20
<212> TYPE: PRT
<213> ORGANISM: Homo sapiens

<400> SEQUENCE: 129

Arg Leu Val Pro Pro Gly Leu Trp Gly Ser Arg His Asn Glu Arg Arg
```

```
1               5                   10                  15

Phe Leu Arg Asn
            20

<210> SEQ ID NO 130
<211> LENGTH: 20
<212> TYPE: PRT
<213> ORGANISM: Homo sapiens

<400> SEQUENCE: 130

Thr Lys Lys Phe Ile Ser Leu Gly Lys His Ala Lys Leu Ser Leu Gln
1               5                   10                  15

Glu Leu Thr Trp
            20

<210> SEQ ID NO 131
<211> LENGTH: 20
<212> TYPE: PRT
<213> ORGANISM: Homo sapiens

<400> SEQUENCE: 131

Lys Met Ser Val Arg Asp Cys Ala Trp Leu Arg Arg Ser Pro Gly Val
1               5                   10                  15

Gly Cys Val Pro
            20

<210> SEQ ID NO 132
<211> LENGTH: 20
<212> TYPE: PRT
<213> ORGANISM: Homo sapiens

<400> SEQUENCE: 132

Ala Ala Glu His Arg Leu Arg Glu Glu Ile Leu Ala Lys Phe Leu His
1               5                   10                  15

Trp Leu Met Ser
            20

<210> SEQ ID NO 133
<211> LENGTH: 20
<212> TYPE: PRT
<213> ORGANISM: Homo sapiens

<400> SEQUENCE: 133

Val Tyr Val Val Glu Leu Leu Arg Ser Phe Phe Tyr Val Thr Glu Thr
1               5                   10                  15

Thr Phe Gln Lys
            20

<210> SEQ ID NO 134
<211> LENGTH: 20
<212> TYPE: PRT
<213> ORGANISM: Homo sapiens

<400> SEQUENCE: 134

Asn Arg Leu Phe Phe Tyr Arg Lys Ser Val Trp Ser Lys Leu Gln Ser
1               5                   10                  15

Ile Gly Ile Arg
            20

<210> SEQ ID NO 135
<211> LENGTH: 20
<212> TYPE: PRT
```

```
<213> ORGANISM: Homo sapiens

<400> SEQUENCE: 135

Gln His Leu Lys Arg Val Gln Leu Arg Glu Leu Ser Glu Ala Glu Val
1               5                   10                  15

Arg Gln His Arg
            20

<210> SEQ ID NO 136
<211> LENGTH: 20
<212> TYPE: PRT
<213> ORGANISM: Homo sapiens

<400> SEQUENCE: 136

Glu Ala Arg Pro Ala Leu Leu Thr Ser Arg Leu Arg Phe Ile Pro Lys
1               5                   10                  15

Pro Asp Gly Leu
            20

<210> SEQ ID NO 137
<211> LENGTH: 20
<212> TYPE: PRT
<213> ORGANISM: Homo sapiens

<400> SEQUENCE: 137

Arg Pro Ile Val Asn Met Asp Tyr Val Val Gly Ala Arg Thr Phe Arg
1               5                   10                  15

Arg Glu Lys Arg
            20

<210> SEQ ID NO 138
<211> LENGTH: 20
<212> TYPE: PRT
<213> ORGANISM: Homo sapiens

<400> SEQUENCE: 138

Ala Glu Arg Leu Thr Ser Arg Val Lys Ala Leu Phe Ser Val Leu Asn
1               5                   10                  15

Tyr Glu Arg Ala
            20

<210> SEQ ID NO 139
<211> LENGTH: 20
<212> TYPE: PRT
<213> ORGANISM: Homo sapiens

<400> SEQUENCE: 139

Arg Arg Pro Gly Leu Leu Gly Ala Ser Val Leu Gly Leu Asp Asp Ile
1               5                   10                  15

His Arg Ala Trp
            20

<210> SEQ ID NO 140
<211> LENGTH: 20
<212> TYPE: PRT
<213> ORGANISM: Homo sapiens

<400> SEQUENCE: 140

Arg Thr Phe Val Leu Arg Val Arg Ala Gln Asp Pro Pro Glu Leu
1               5                   10                  15

Tyr Phe Val Lys
            20
```

<210> SEQ ID NO 141
<211> LENGTH: 20
<212> TYPE: PRT
<213> ORGANISM: Homo sapiens

<400> SEQUENCE: 141

Val Asp Val Thr Gly Ala Tyr Asp Thr Ile Pro Gln Asp Arg Leu Thr
1               5                   10                  15

Glu Val Ile Ala
            20

<210> SEQ ID NO 142
<211> LENGTH: 20
<212> TYPE: PRT
<213> ORGANISM: Homo sapiens

<400> SEQUENCE: 142

Ser Ile Ile Lys Pro Gln Asn Thr Tyr Cys Val Arg Arg Tyr Ala Val
1               5                   10                  15

Val Gln Lys Ala
            20

<210> SEQ ID NO 143
<211> LENGTH: 20
<212> TYPE: PRT
<213> ORGANISM: Homo sapiens

<400> SEQUENCE: 143

Ala His Gly His Val Arg Lys Ala Phe Lys Ser His Val Ser Thr Leu
1               5                   10                  15

Thr Asp Leu Gln
            20

<210> SEQ ID NO 144
<211> LENGTH: 20
<212> TYPE: PRT
<213> ORGANISM: Homo sapiens

<400> SEQUENCE: 144

Pro Tyr Met Arg Gln Phe Val Ala His Leu Gln Glu Thr Ser Pro Leu
1               5                   10                  15

Arg Asp Ala Val
            20

<210> SEQ ID NO 145
<211> LENGTH: 20
<212> TYPE: PRT
<213> ORGANISM: Homo sapiens

<400> SEQUENCE: 145

Val Ile Glu Gln Ser Ser Ser Leu Asn Glu Ala Ser Ser Gly Leu Phe
1               5                   10                  15

Asp Val Phe Leu
            20

<210> SEQ ID NO 146
<211> LENGTH: 20
<212> TYPE: PRT
<213> ORGANISM: Homo sapiens

<400> SEQUENCE: 146

```
Arg Phe Met Cys His His Ala Val Arg Ile Arg Gly Lys Ser Tyr Val
1               5                   10                  15

Gln Cys Gln Gly
            20

<210> SEQ ID NO 147
<211> LENGTH: 20
<212> TYPE: PRT
<213> ORGANISM: Homo sapiens

<400> SEQUENCE: 147

Ile Pro Gln Gly Ser Ile Leu Ser Thr Leu Leu Cys Ser Leu Cys Tyr
1               5                   10                  15

Gly Asp Met Glu
            20

<210> SEQ ID NO 148
<211> LENGTH: 20
<212> TYPE: PRT
<213> ORGANISM: Homo sapiens

<400> SEQUENCE: 148

Asn Lys Leu Phe Ala Gly Ile Arg Arg Asp Gly Leu Leu Leu Arg Leu
1               5                   10                  15

Val Asp Asp Phe
            20

<210> SEQ ID NO 149
<211> LENGTH: 20
<212> TYPE: PRT
<213> ORGANISM: Homo sapiens

<400> SEQUENCE: 149

Leu Leu Val Thr Pro His Leu Thr His Ala Lys Thr Phe Leu Arg Thr
1               5                   10                  15

Leu Val Arg Gly
            20

<210> SEQ ID NO 150
<211> LENGTH: 20
<212> TYPE: PRT
<213> ORGANISM: Homo sapiens

<400> SEQUENCE: 150

Val Pro Glu Tyr Gly Cys Val Val Asn Leu Arg Lys Thr Val Val Asn
1               5                   10                  15

Phe Pro Val Glu
            20

<210> SEQ ID NO 151
<211> LENGTH: 20
<212> TYPE: PRT
<213> ORGANISM: Homo sapiens

<400> SEQUENCE: 151

Asp Glu Ala Leu Gly Gly Thr Ala Phe Val Gln Met Pro Ala His Gly
1               5                   10                  15

Leu Phe Pro Trp
            20

<210> SEQ ID NO 152
<211> LENGTH: 20
```

<212> TYPE: PRT
<213> ORGANISM: Homo sapiens

<400> SEQUENCE: 152

Cys Gly Leu Leu Leu Asp Thr Arg Thr Leu Glu Val Gln Ser Asp Tyr
1               5                   10                  15

Ser Ser Tyr Ala
            20

<210> SEQ ID NO 153
<211> LENGTH: 20
<212> TYPE: PRT
<213> ORGANISM: Homo sapiens

<400> SEQUENCE: 153

Arg Thr Ser Ile Arg Ala Ser Leu Thr Phe Asn Arg Gly Phe Lys Ala
1               5                   10                  15

Gly Arg Asn Met
            20

<210> SEQ ID NO 154
<211> LENGTH: 20
<212> TYPE: PRT
<213> ORGANISM: Homo sapiens

<400> SEQUENCE: 154

Arg Arg Lys Leu Phe Gly Val Leu Arg Leu Lys Cys His Ser Leu Phe
1               5                   10                  15

Leu Asp Leu Gln
            20

<210> SEQ ID NO 155
<211> LENGTH: 20
<212> TYPE: PRT
<213> ORGANISM: Homo sapiens

<400> SEQUENCE: 155

Val Asn Ser Leu Gln Thr Val Cys Thr Asn Ile Tyr Lys Ile Leu Leu
1               5                   10                  15

Leu Gln Ala Tyr
            20

<210> SEQ ID NO 156
<211> LENGTH: 20
<212> TYPE: PRT
<213> ORGANISM: Homo sapiens

<400> SEQUENCE: 156

Arg Phe His Ala Cys Val Leu Gln Leu Pro Phe His Gln Gln Val Trp
1               5                   10                  15

Lys Asn Pro Thr
            20

<210> SEQ ID NO 157
<211> LENGTH: 20
<212> TYPE: PRT
<213> ORGANISM: Homo sapiens

<400> SEQUENCE: 157

Phe Phe Leu Arg Val Ile Ser Asp Thr Ala Ser Leu Cys Tyr Ser Ile
1               5                   10                  15

Leu Lys Ala Lys

20

<210> SEQ ID NO 158
<211> LENGTH: 20
<212> TYPE: PRT
<213> ORGANISM: Homo sapiens

<400> SEQUENCE: 158

Asn Ala Gly Met Ser Leu Gly Ala Lys Gly Ala Ala Gly Pro Leu Pro
1               5                   10                  15

Ser Glu Ala Val
        20

<210> SEQ ID NO 159
<211> LENGTH: 20
<212> TYPE: PRT
<213> ORGANISM: Homo sapiens

<400> SEQUENCE: 159

Gln Trp Leu Cys His Gln Ala Phe Leu Leu Lys Leu Thr Arg His Arg
1               5                   10                  15

Val Thr Tyr Val
        20

<210> SEQ ID NO 160
<211> LENGTH: 20
<212> TYPE: PRT
<213> ORGANISM: Homo sapiens

<400> SEQUENCE: 160

Pro Leu Leu Gly Ser Leu Arg Thr Ala Gln Thr Gln Leu Ser Arg Lys
1               5                   10                  15

Leu Pro Gly Thr
        20

<210> SEQ ID NO 161
<211> LENGTH: 22
<212> TYPE: PRT
<213> ORGANISM: Homo sapiens

<400> SEQUENCE: 161

Thr Leu Thr Ala Leu Glu Ala Ala Ala Asn Pro Ala Leu Pro Ser Asp
1               5                   10                  15

Phe Lys Thr Ile Leu Asp
        20

<210> SEQ ID NO 162
<211> LENGTH: 1132
<212> TYPE: PRT
<213> ORGANISM: Homo sapiens

<400> SEQUENCE: 162

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu

-continued

```
         65                  70                  75                  80
Val Ala Arg Val Leu Gln Arg Leu Cys Glu Arg Gly Ala Lys Asn Val
                    85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
                115                 120                 125

Asp Ala Leu Arg Gly Ser Gly Ala Trp Gly Leu Leu Leu Arg Arg Val
            130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
                180                 185                 190

Pro Arg Arg Arg Leu Gly Cys Glu Arg Ala Trp Asn His Ser Val Arg
                195                 200                 205

Glu Ala Gly Val Pro Leu Gly Leu Pro Ala Pro Gly Ala Arg Arg Arg
            210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Glu Ala Thr Ser Leu Glu Gly Ala
                275                 280                 285

Leu Ser Gly Thr Arg His Ser His Pro Ser Val Gly Arg Gln His His
            290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
            370                 375                 380

Arg Tyr Trp Gln Met Arg Pro Leu Phe Leu Glu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Glu Asp Thr Asp Pro Arg Arg Leu
            435                 440                 445

Val Gln Leu Leu Arg Gln His Ser Ser Pro Trp Gln Val Tyr Gly Phe
            450                 455                 460

Val Arg Ala Cys Leu Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495
```

-continued

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
        580                 585                 590

Leu Lys Arg Val Gln Leu Arg Glu Leu Ser Glu Ala Glu Val Arg Gln
    595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
        660                 665                 670

Pro Gly Leu Leu Gly Ala Ser Val Leu Gly Leu Asp Asp Ile His Arg
    675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
        820                 825                 830

Gln Gly Ser Ile Leu Ser Thr Leu Leu Cys Ser Leu Cys Tyr Gly Asp
    835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

```
Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
        930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 163
<211> LENGTH: 16
<212> TYPE: PRT
<213> ORGANISM: Homo sapiens

<400> SEQUENCE: 163

Glu Ala Arg Pro Ala Leu Leu Thr Ser Arg Leu Arg Phe Ile Pro Lys
1               5                   10                  15
```

ANTI-INFLAMMATORY PEPTIDES AND COMPOSITION COMPRISING THE SAME

SEQUENCE LISTING

The instant application contains a Sequence Listing which has been submitted electronically in ASCII format and is hereby incorporated by reference in its entirety. Said ASCII copy, created on Jul. 20, 2021, is named 51553-002005_Sequence_Listing_7_14_21_ST25, and is 46,672 bytes in size.

FIELD OF THE INVENTION

The present invention relates to anti-inflammatory peptides and compositions comprising the same.

BACKGROUND OF THE INVENTION

Inflammation is a type of biological defense as a means of protecting the body from damage of biological tissues that could be caused by external physical stimuli, chemical stimuli such as exposure to various allergens, or invasion of microorganisms including bacteria, fungi and viruses.

The Cyclooxygenase (COX) pathway or Lipoxygenase (LOX) Pathway can used for signaling inflammation, which produce prostaglandin, thromboxane, etc. Once the inflammatory signal is delivered, one of many changes that happen in the body is the expansion of the blood vessel for increased blood supply around the inflammation to concentrate blood cells such as neutrophils required for the inflammatory response. However, inflammatory diseases can result if an abnormal biological defense response occurs excessively. To prevent this, drugs that suppress excessive inflammatory responses by repressing enzymes used in inflammatory signaling pathways (for example COX-1, COX-2, 5-LOX, 12-LOX etc.) are under development.

According to response time, inflammation is categorized as acute inflammation (immediate response, non-specific response, several days to several weeks), chronic inflammation (delayed response, specific response, several weeks or more), subacute inflammation (a middle stage in between acute inflammation and chronic inflammation, characteristics of mixed product of mononuclear and polymorphounuclear).

Also, aside from peptide factors, factors such as prostaglandin, leukotriene, lipid factors including platelet activating factor (PAF), synthetic enzyme of inflammation factor, free radical such as NO (nitric oxide), many kinds of cell adhesion molecules, the immune system, and coagulation factors can cause inflammation.

Once a cell is damaged due to the known causative agents of inflammation such as external biological factors (microbes, viruses, parasites), physical factors (mechanical stimuli, heat, radiation, electricity), and chemical factors, histamine and kinin are released. The released histamine and kinin will result in angiectasis, increased capillary permeability and concentration of macrophages at the inflammation site, and it causes increased blood flow rate, edema, immunocyte and antibody migration, pain and heat generation.

Currently used treatments for inflammation are synthetic drugs such as ibuprofen, antihistamines, steroids, cortisone, immunosuppressive agents, and immune agonist; those which only temporarily alleviate inflammation. These drugs do not fundamentally cure inflammation, and they have side effects such as hypersensitivity reaction, and deterioration of immune system, Therefore, for effective alleviation of inflammation, research is being done to develop a substance that inhibits expression of the above mentioned inflammatory proteins. However, problems have arisen in anti-inflammation substances that had been developed previously. Diverse categories of anti-inflammatory drugs including Non-steroidal Anti-inflammatory Drugs (NSAIDs) and Steroidal Anti-inflammatory Drugs (SAIDs) have been developed; but not only do these drugs often bear side effects upon use, they also do not fundamentally cure the inflammation. Thus, there is a current need for anti-inflammatory drugs that are both physically and economically feasible. As one example, in acute or chronic inflammations such as chronic rheumatoid arthritis, not only do non-steroidal anti-inflammatory drugs suppress COX-2 enzyme activity, they are also known to suppress COX-1 activity, causing side effects such as gastrointestinal disorders.

The present invention was completed as the present inventors have found that peptides derived from telomerase can have anti-inflammatory properties.

Therefore the objective of this invention is to provide a novel peptide.

Another objective of present invention is to provide the polynucleotide that codes the novel peptide.

Another objective of present invention is to provide a peptide that has anti-inflammatory activity.

Another objective of present invention is to provide an anti-inflammatory composition that uses this peptide as an active ingredient.

Another objective of present invention is to provide a cosmetic composition that uses this peptide as an active ingredient.

Another objective of present invention is to provide a pharmaceutical composition that uses this peptide as an active ingredient.

SUMMARY OF THE INVENTION

In one embodiment the present invention relates to a peptide with anti-Inflammatory activity, wherein the peptide comprises at least one amino acid sequence of SEQ ID NO: 1 to SEQ ID NO: 161, or where the peptide has at least 80% sequence identity with the above-mentioned sequences, or the peptide is a fragment of the above-mentioned peptides.

In another embodiment, the above-mentioned fragment consists of 3 or more amino acids. For instance, the fragment may consist of 4, 5, 6, 7, 8, 9, 10, 11, 12, 13, 14, 15, 16, 17, 18, 19, 20, 21, 22, 23, 24, 25, or 26 amino acid residues.

In another embodiment, the above-mentioned peptide consists of 30 or less amino acids. For instance, the peptide may consist of 29, 28, 27, 26, 25, 24, 23, 22, 21, 20, 19, 18, 17, 16, 15, 14, 13, 12, 11, 10, 9, or 8 amino acid residues.

In another embodiment, the above-mentioned peptide consists of any one amino acid sequence of SEQ ID NO: 1 to SEQ ID NO: 161.

In another embodiment, the above-mentioned peptide comprises any one amino acid sequence selected from the group consisting of: SEQ ID NO: 1 to SEQ ID NO: 6, SEQ ID NO: 9, SEQ ID NO: 11, SEQ ID NO: 14 to 21, SEQ ID NO: 23 to SEQ ID NO: 37, SEQ ID NO: 39 to SEQ ID NO: 44, SEQ ID NO: 47 to SEQ ID NO: 53, SEQ ID NO: 55 to SEQ ID NO: 61, SEQ ID NO: 63 to SEQ ID NO: 82, SEQ ID NO: 84 to SEQ ID NO: 94, SEQ ID NO: 96, SEQ ID NO: 99 to SEQ ID NO: 104, SEQ ID NO: 107 to SEQ ID NO:

109, SEQ ID NO: 115, SEQ ID NO: 116, SEQ ID NO: 120 to SEQ ID NO: 122, SEQ ID NO: 124, SEQ ID NO: 129 to SEQ ID NO: 133, SEQ ID NO: 142 to SEQ ID NO: 144, SEQ ID NO: 146, SEQ ID NO: 148, SEQ ID NO: 149, and SEQ ID NO: 155 to SEQ ID NO: 159.

In another embodiment, the above-mentioned peptide comprises any one amino acid sequence selected from the group consisting of: SEQ ID NO: 15 to SEQ ID NO: 18, SEQ ID NO: 23 to SEQ ID NO: 27, SEQ ID NO: 29, SEQ ID NO: 31 to SEQ ID NO: 34, SEQ ID NO: 39 to SEQ ID NO: 41, SEQ ID NO: 47, SEQ ID NO:48, SEQ ID NO: 51 to SEQ ID NO: 53, SEQ ID NO: 55 to SEQ ID NO: 58, SEQ ID NO: 61, SEQ ID NO: 65 to SEQ ID NO: 68, SEQ ID NO: 70, SEQ ID NO: 73 to SEQ ID NO: 79, SEQ ID NO: 81, SEQ ID NO: 82, SEQ ID NO: 84 to SEQ ID NO: 87, SEQ ID NO: 90 to SEQ ID NO: 94, SEQ ID NO: 96, SEQ ID NO: 99, SEQ ID NO: 101 to SEQ ID NO: 104, SEQ ID NO: 107 to SEQ ID NO: 109, SEQ ID NO: 120, SEQ ID NO: 121, SEQ ID NO: 129 to SEQ ID NO: 132, SEQ ID NO: 142 to SEQ ID NO: 144, SEQ ID NO: 146, SEQ ID NO: 148, SEQ ID NO: 149, and SEQ ID NO: 157 to SEQ ID NO: 159.

In another embodiment, the above-mentioned peptide comprises any one amino acid sequence selected from the group consisting of: SEQ ID NO: 1 to SEQ ID NO: 5, SEQ ID NO: 7, SEQ ID NO: 9, SEQ ID NO: 10, SEQ ID NO: 12, SEQ ID NO: 13, SEQ ID NO: 15, SEQ ID NO: 17 to SEQ ID NO: 27, SEQ ID NO: 29, SEQ ID NO: 30, SEQ ID NO: 32 to SEQ ID NO: 53, SEQ ID NO: 55 to SEQ ID NO: 60, SEQ ID NO: 67, SEQ ID NO: 68, SEQ ID NO: 70, SEQ ID NO: 72 to SEQ ID NO: 82, SEQ ID NO: 84 to SEQ ID NO: 92, SEQ ID NO: 94, SEQ ID NO: 99 to SEQ ID NO: 112, SEQ ID NO: 114, SEQ ID NO: 127 to SEQ ID NO: 144, SEQ ID NO: 146, SEQ ID NO: 148, SEQ ID NO: 149, SEQ ID NO: 151 and SEQ ID NO: 153 to SEQ ID NO: 161.

In another embodiment, the above-mentioned peptide comprises any one amino acid sequence selected from the group consisting of: SEQ ID NO: 1 to SEQ ID NO: 5, SEQ ID NO: 7, SEQ ID NO: 9, SEQ ID NO: 10, SEQ ID NO: 12, SEQ ID NO: 13, SEQ ID NO: 15, SEQ ID NO: 17 to SEQ ID NO: 23, SEQ ID NO: 25 to SEQ ID NO: 27, SEQ ID NO: 29, SEQ ID NO: 30, SEQ ID NO: 33 to SEQ ID NO: 43, SEQ ID NO: 156, SEQ ID NO: 157 and SEQ ID NO: 159.

In another embodiment, the above-mentioned peptide comprises any one amino acid sequence selected from the group consisting of: SEQ ID NO: 1, SEQ ID NO: 2, SEQ ID NO: 4, SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 15, SEQ ID NO: 17, SEQ ID NO: 18, SEQ ID NO: 20, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 44, SEQ ID NO: 45, SEQ ID NO: 52, SEQ ID NO: 57, SEQ ID NO: 60, SEQ ID NO: 61, SEQ ID NO: 62, SEQ ID NO: 64, SEQ ID NO: 65, SEQ ID NO: 67, SEQ ID NO: 68, SEQ ID NO: 69, SEQ ID NO: 91, SEQ ID NO: 99, SEQ ID NO: 100, SEQ ID NO: 104, SEQ ID NO: 106, SEQ ID NO: 107, SEQ ID NO: 108, SEQ ID NO: 109, SEQ ID NO: 111, SEQ ID NO: 112, SEQ ID NO: 115, SEQ ID NO: 117, SEQ ID NO: 118, SEQ ID NO: 119, SEQ ID NO: 120, SEQ ID NO: 122, SEQ ID NO: 124, SEQ ID NO: 125, SEQ ID NO: 126, SEQ ID NO: 129, SEQ ID NO: 130, SEQ ID NO: 131, SEQ ID NO: 132, SEQ ID NO: 135, SEQ ID NO: 146, SEQ ID NO: 151, SEQ ID NO: 154, and SEQ ID NO: 156.

In another embodiment, the above-mentioned peptide originates from human telomerase.

In one embodiment of the present invention, a polynucleotide encoding a peptide with anti-inflammatory activity, wherein the peptide comprises at least one amino acid sequence of SEQ ID NO: 1 to SEQ ID NO: 161, or the peptide has at least 80% sequence identity with the above-mentioned sequences, or the peptide is a fragment of the above-mentioned peptides, is provided.

In another embodiment of the polynucleotide, the above-mentioned peptide consists of 30 or less amino acids. For instance, the peptide may consist of 29, 28, 27, 26, 25, 24, 23, 22, 21, 20, 19, 18, 17, 16, 15, 14, 13, 12, 11, 10, 9, or 8 amino acid residues.

In another embodiment of the polynucleotide, the above-mentioned peptide consists of any one amino acid sequence of SEQ ID NO: 1 to SEQ ID NO: 161.

In another embodiment of the polynucleotide, the above-mentioned peptide originates from human telomerase.

In one embodiment of the present invention, anti-inflammatory composition comprising a peptide as active ingredient, wherein the peptide comprises at least one amino acid sequence of SEQ ID NO: 1 to SEQ ID NO: 161, the peptide has above 80% homology of amino acid sequence with above-mentioned sequences, or the peptide is a fragment of the above-mentioned peptides, is provided.

In another embodiment of the composition, the above-mentioned peptide consists of 30 or less amino acids, cf. above.

In another embodiment of the composition, the above-mentioned peptide consists of any one amino acid sequence of SEQ ID NO: 1 to SEQ ID NO: 161.

In another embodiment of the composition, the above-mentioned peptide originates from human telomerase.

In another embodiment of the composition, the above-mentioned composition is for treatment or prophylaxis of inflammatory disease.

In another embodiment of the composition, the above-mentioned composition is a cosmetic composition for improving or preventing skin inflammation.

In another embodiment of the composition, the above-mentioned composition is a pharmaceutical composition for treatment or prophylaxis of Inflammatory diseases.

In another embodiment of the composition, the above-mentioned composition is a food composition for treatment or prophylaxis of inflammation.

In another embodiment of the composition, the above-mentioned inflammatory disease is characterized by selecting from the group consisting of (1) general or localized inflammatory disease (for example, allergies; immune-complex disease; hayfever; hypersensitive shock; endotoxin shock; cachexia, hyperthermia; granulomatosis; or sarcoidosis); (2) gastro-intestinal related diseases (for example, appendicitis; gastric ulcer; duodenal ulcer; peritonitis; pancreatitis; ulcerative, acute, or ischemic colitis; cholangitis; cholecystitis, steatorrhea, hepatitis, Crone's disease; or Whipple's Disease); (3) dermal related diseases (for example, psoriasis; burns; sunburns; dermatitis; Urticarial warts or wheal); (4) vascular related diseases (for example, angiitis; vasculitis; endocarditis; arteritis; atherosclerosis; thrombophlebitis; pericarditis; congestive heart failure; myocarditis; myocardial ischemia; periarteritis nodosa; recurrent stenosis; Buerger's disease; or rheumatic fever); (5) respiratory diseases (for example, asthma; epiglottitis; bronchitis; emphysema; rhinitis; cystic fibrosis; interstitial pneumonitis; COPD (chronic obstructive pulmonary disease); adult respiratory distress syndrome; coniosis; alveolitis; bronchiolitis; pharyngitis; pleurisy; or sinusitis); (6) bone, joint, muscle and connective tissue related diseases (for example, eosinophilic granuloma; arthritis; arthralgia; osteomyelitis; dermatomyositis; fasciitis; Paget's disease; gout; periodontal disease; rheumatoid arthritis; myasthenia gravis; ankylosing spondylitis; or synovitis); (7) urogenital disorders (for example, epididymitis; vaginitis; prostatitis; or urethritis); (8) central or peripheral nervous system related diseases (for example, Alzheimer's disease; meningitis; encephalitis; multiple sclerosis; cerebral infarction; cerebral embolism; Guillain-Barre syndrome; neuritis; neuralgia; spinal cord injury; paralysis; or uveitis); (9) virus (for example, influenza; respiratory syncytial virus; HIV; hepatitis B; hepatitis C; or herpes virus), infectious disease (for example, Dengue fever; or septicemia), fungal infection (for example, candidiasis); or bacterial, parasitic, and similar microbial infection (for example, disseminated bacteremia; malaria; onchocerciasis; or amebiasis); (10) autoimmune disease (for example, thyroiditis; lupus; Goodpasture's syndrome; allograft rejection; graft versus host disease; or diabetes); and (11) cancer or tumor disease (for example, Hodgkin's disease).

In one embodiment of the present invention, a method for treating or preventing inflammatory diseases by administering the anti-inflammatory composition is provided.

In one embodiment of the present invention, a kit for prophylaxis or treatment of inflammatory diseases comprising: a peptide with anti-inflammatory activity or a composition comprising of the peptide, wherein the peptide comprises at least one amino acid sequence of SEQ ID NO: 1 to SEQ ID NO: 161, the peptide has above 80% homology with above-mentioned sequences, or the peptide is a fragment of the above-mentioned peptides; and instructions including at least one of administration dose, administration route, administration frequency, and indication of the peptide or composition, is provided.

INDUSTRIAL APPLICABILITY

According to the present invention, a peptide that has a sequence of SEQ ID NO: 1 to SEQ ID NO: 161 has outstanding efficacy in both suppressing inflammation and in prophylactic means. Therefore, the composition comprising the peptides of this invention can be used as anti-inflammatory pharmaceutical composition or as cosmetic composition, in turn, treating and preventing a variety of different types of inflammatory diseases.

REFERENCES

KR2012-0130996A
KR2012-0133661A
KR2011-0060940A
US2011-0150873A1
Bonaldi T et al., EMBO J, (22)5551-60, 2003
Yankner B A et al, Science (New York, N.Y.) [1990, 250 (4978):279-282]
Dahlgren K N et al, J. Biol. Chem. 277:32046-32053, 2002.

DETAILED DESCRIPTION OF THE INVENTION

Figure 1:
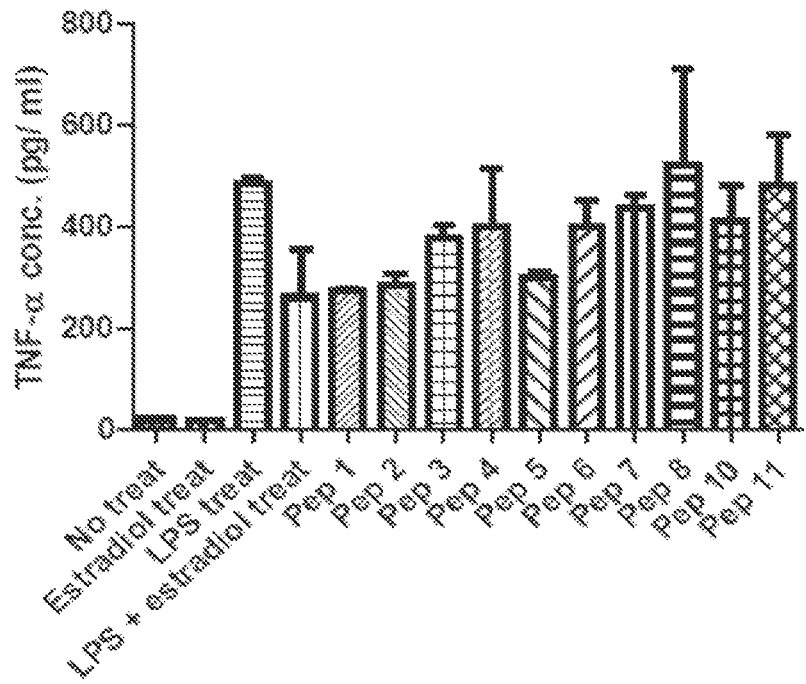
FIG. 1 to FIG. 16 are results from screening TNF-α inhibition effects on monocytes.
Figure 2:
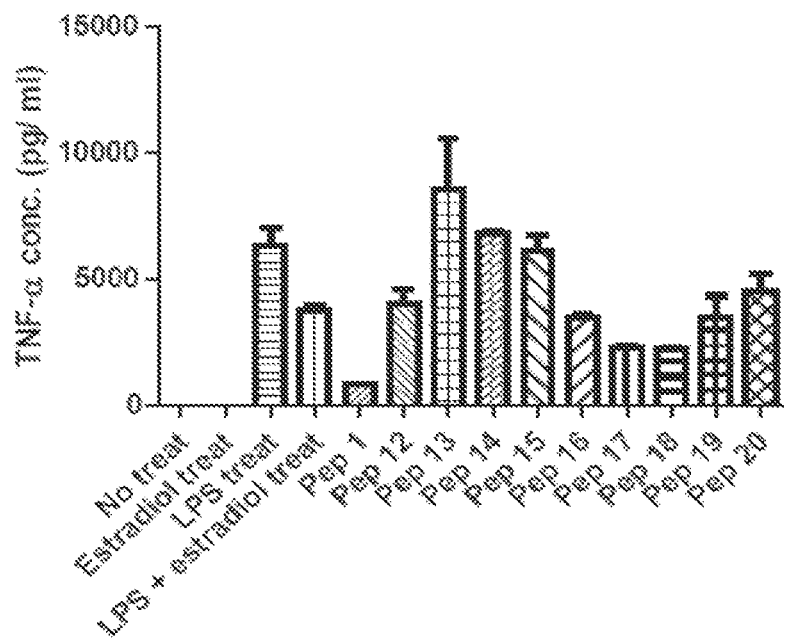
Figure 3:
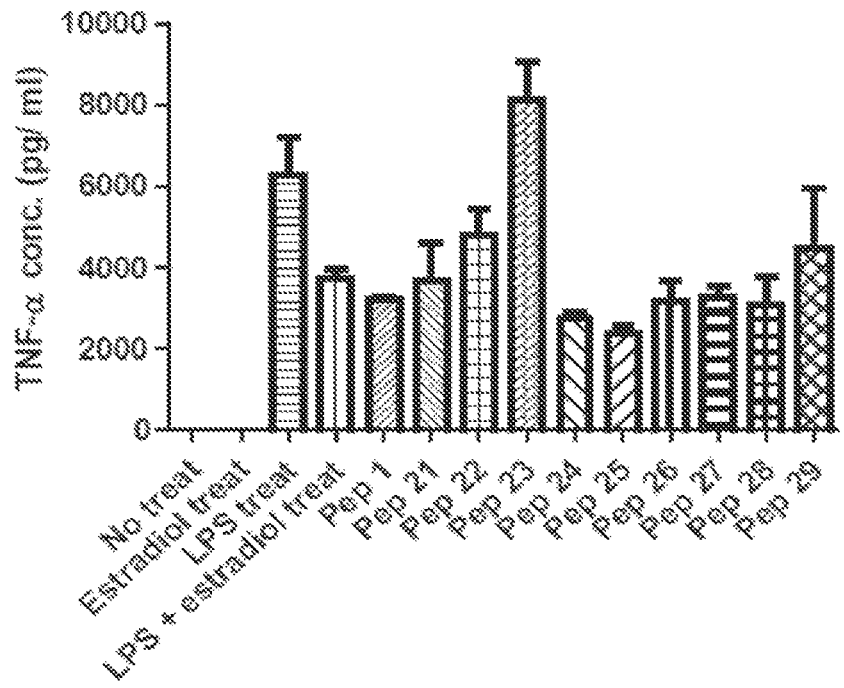
Figure 4:
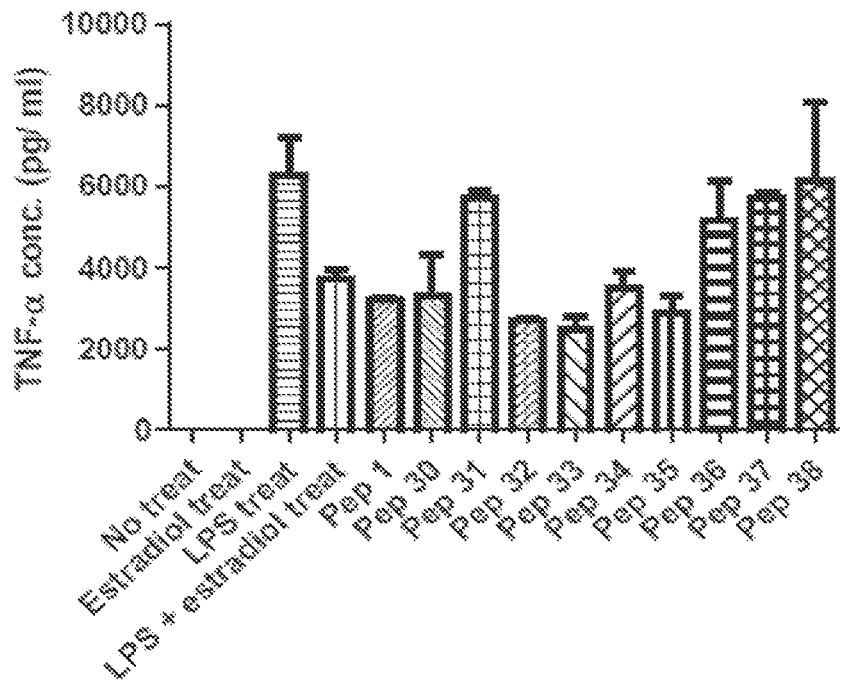
Figure 5:
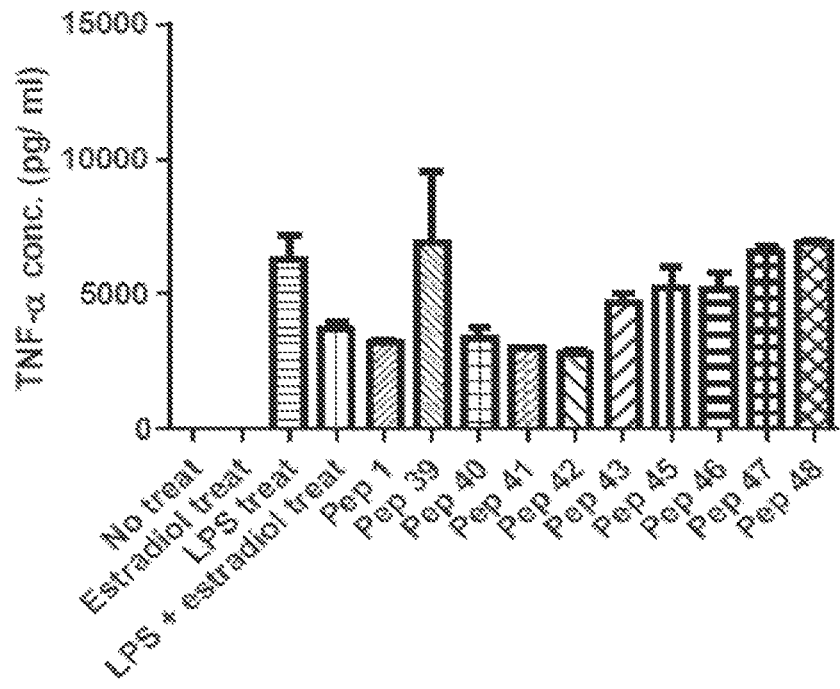
Figure 6:
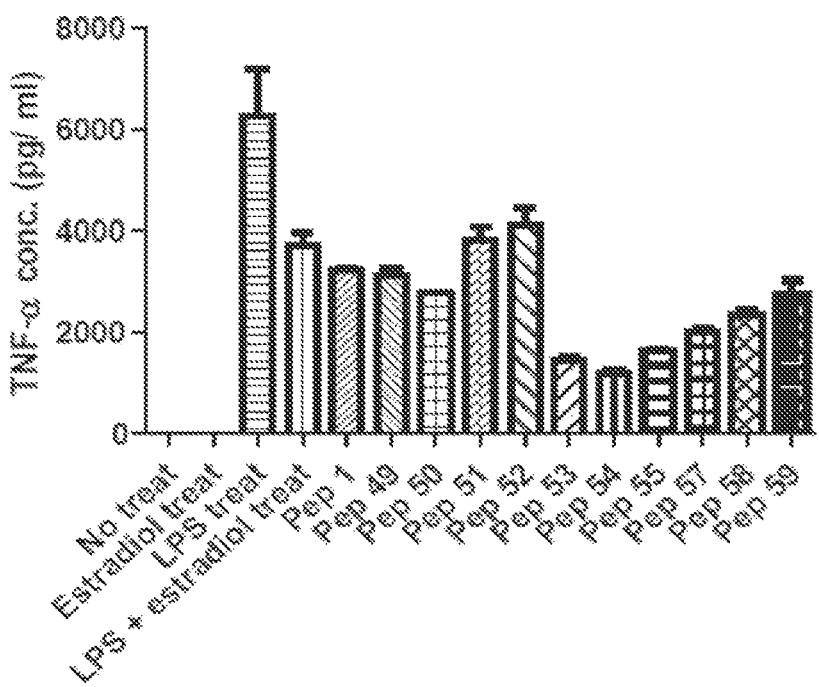
Figure 7:
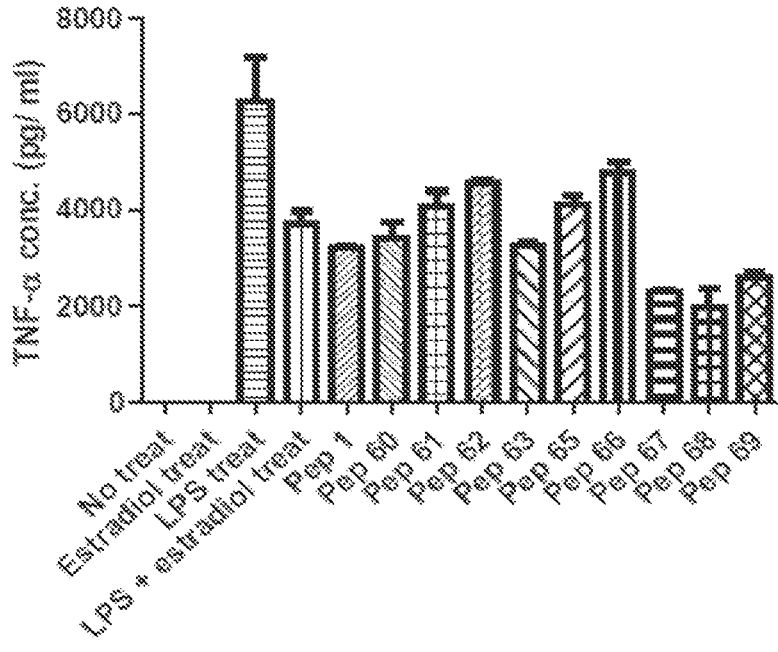
Figure 8:
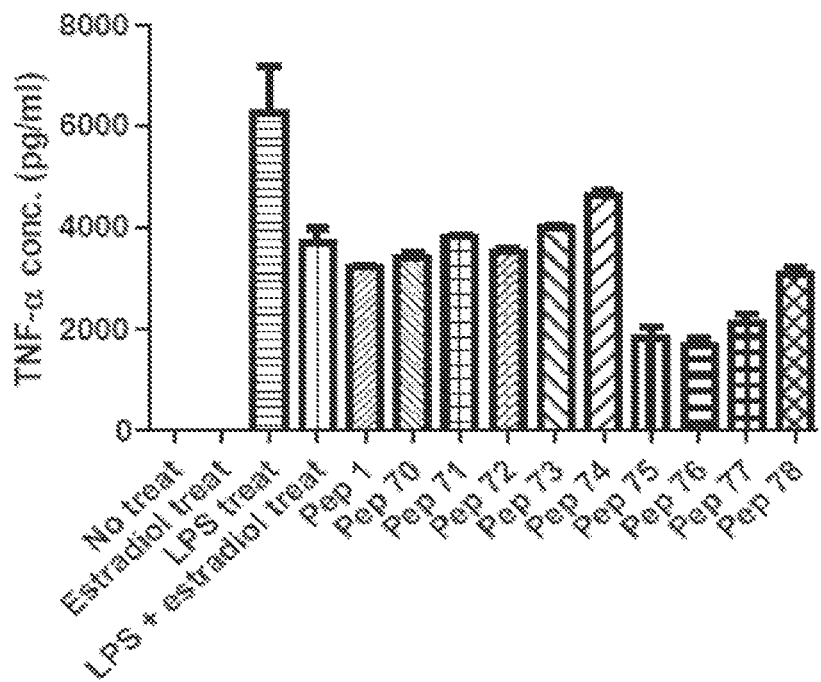
Figure 9:
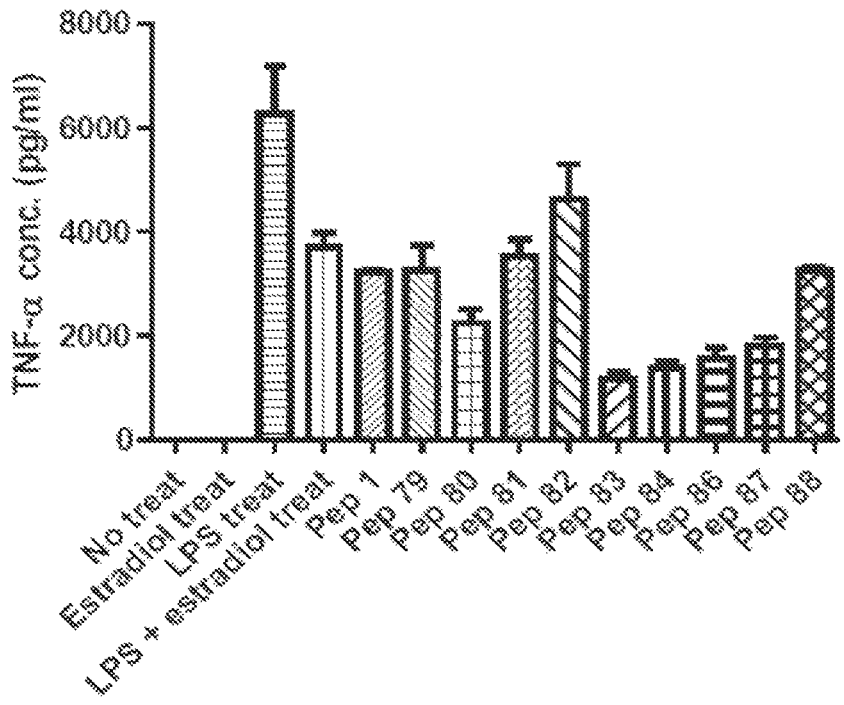
Figure 10:
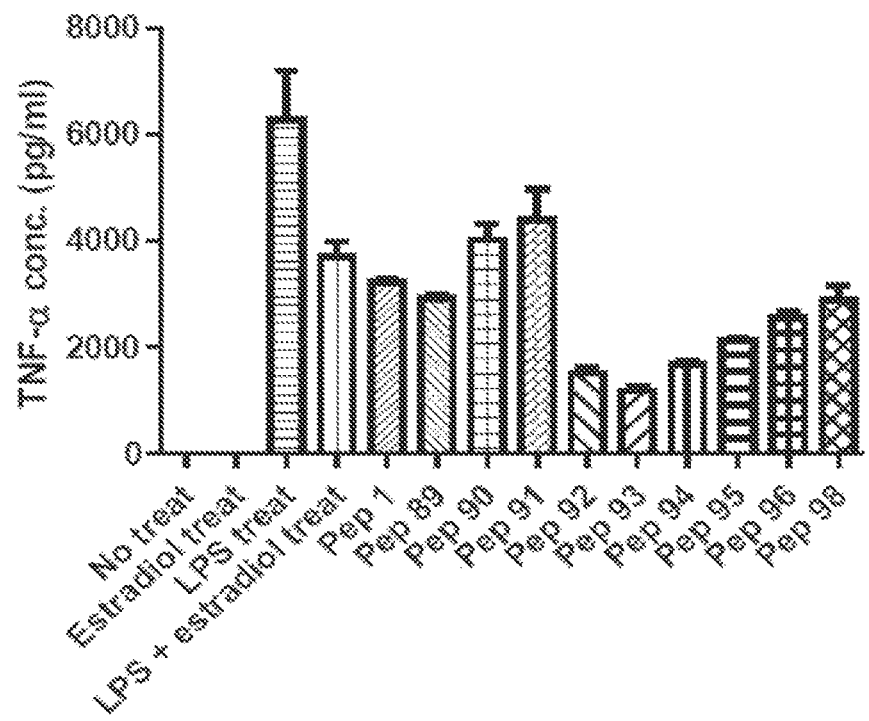
Figure 11:
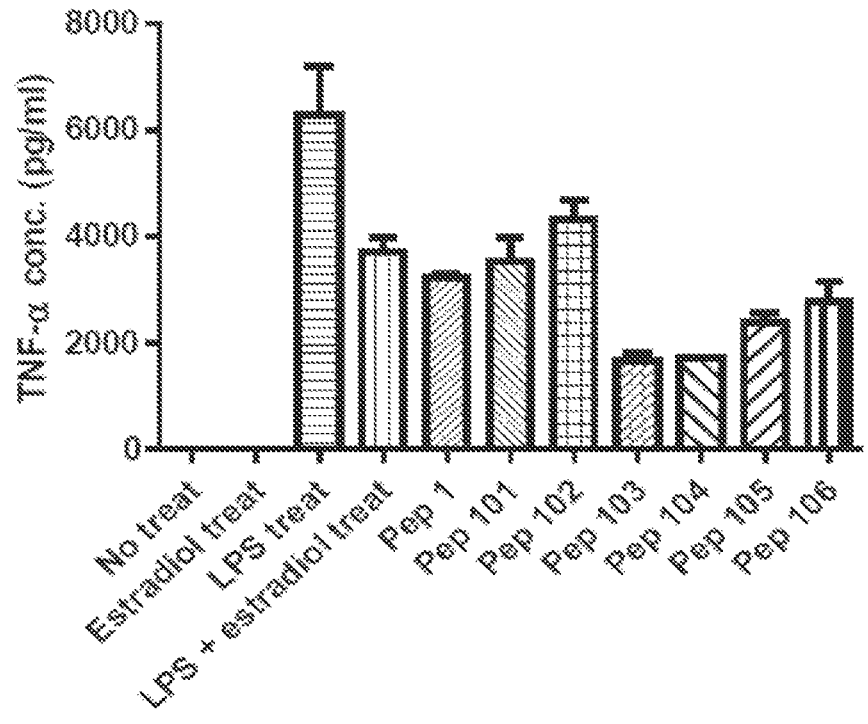
Figure 12:
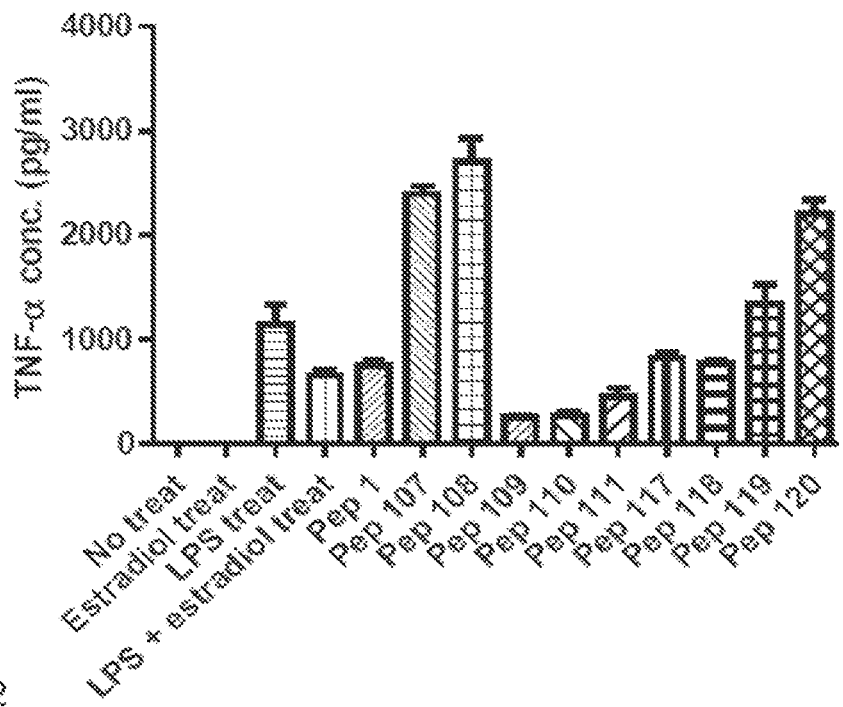
Figure 13:
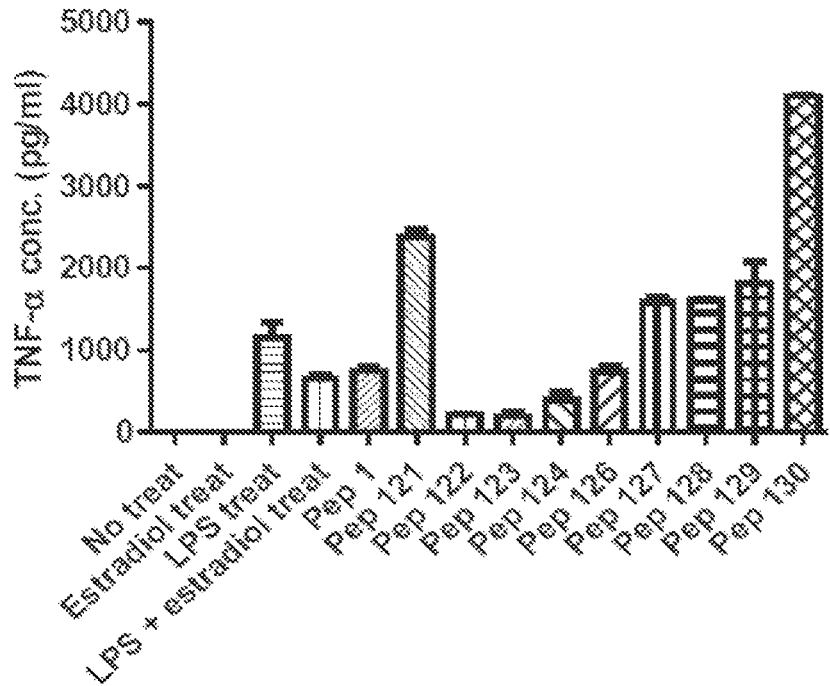
Figure 14:
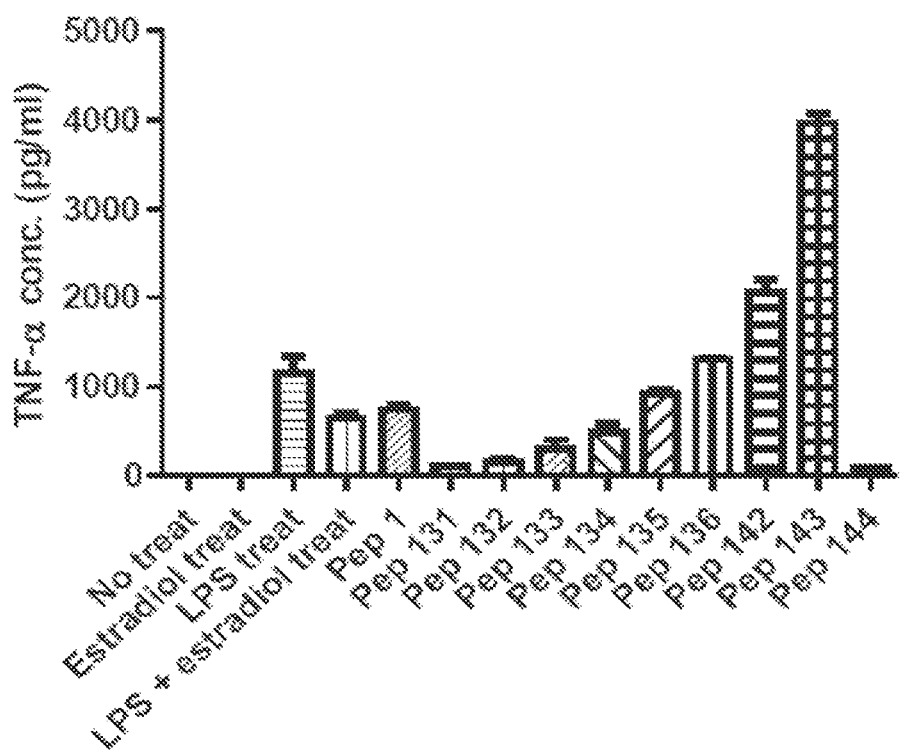
Figure 15:
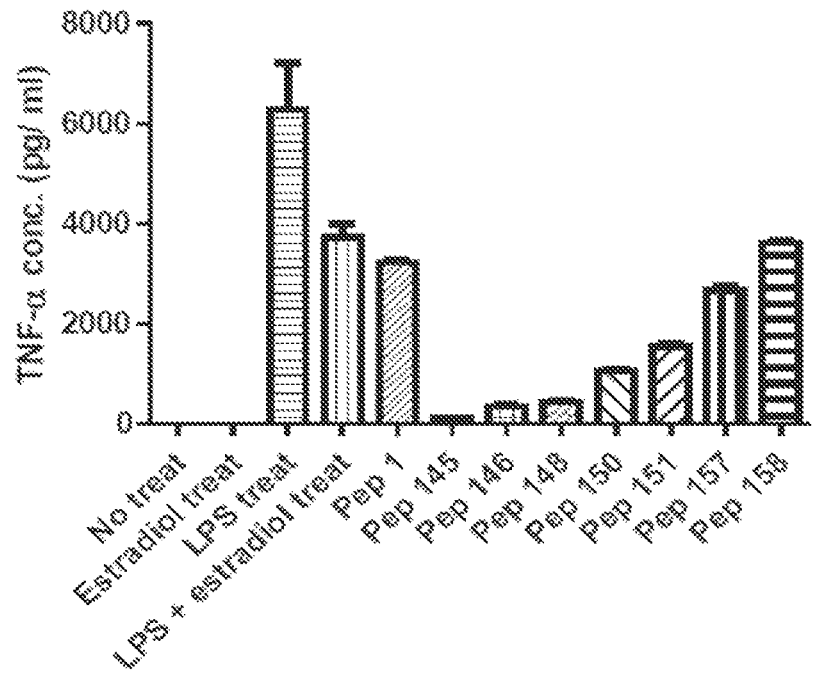
Figure 16:
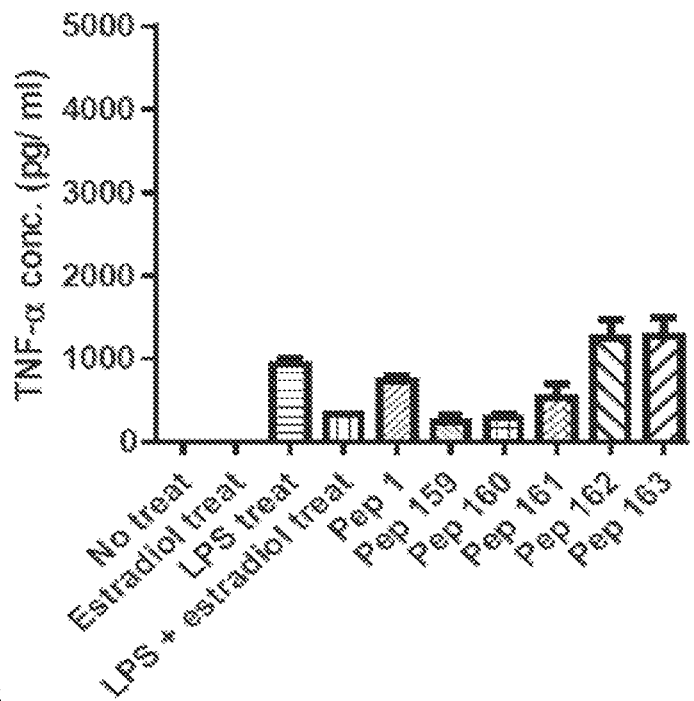
Figure 17:
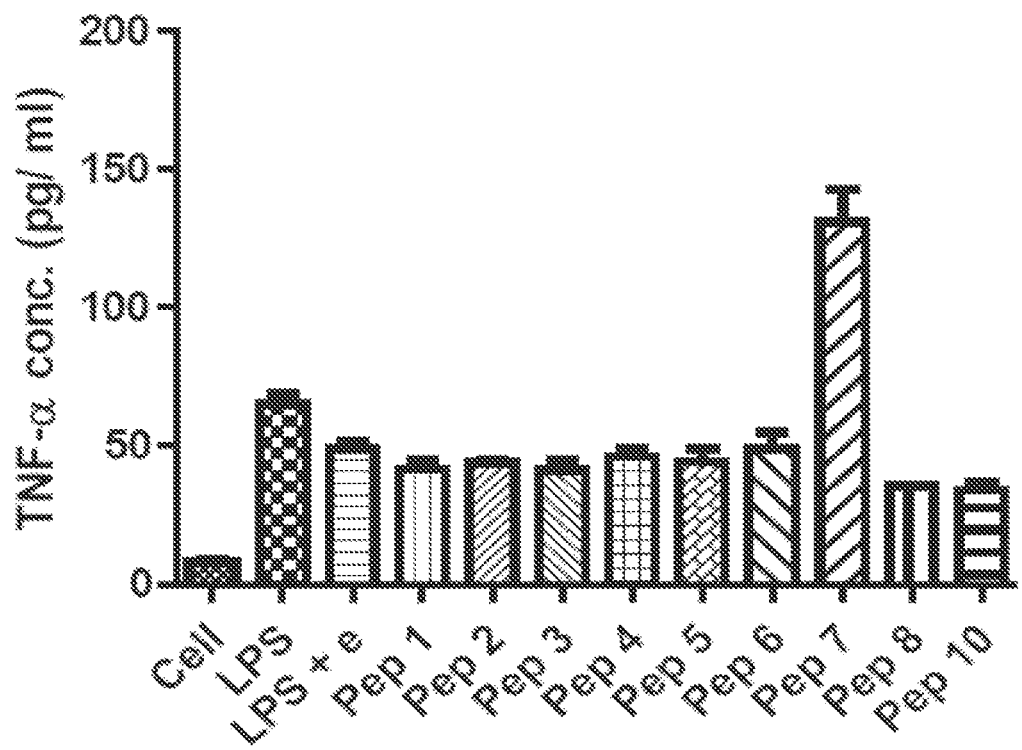
FIG. 17 to FIG. 35 are results from screening TNF-α inhibition effects on cell line THP-1.
Figure 18:
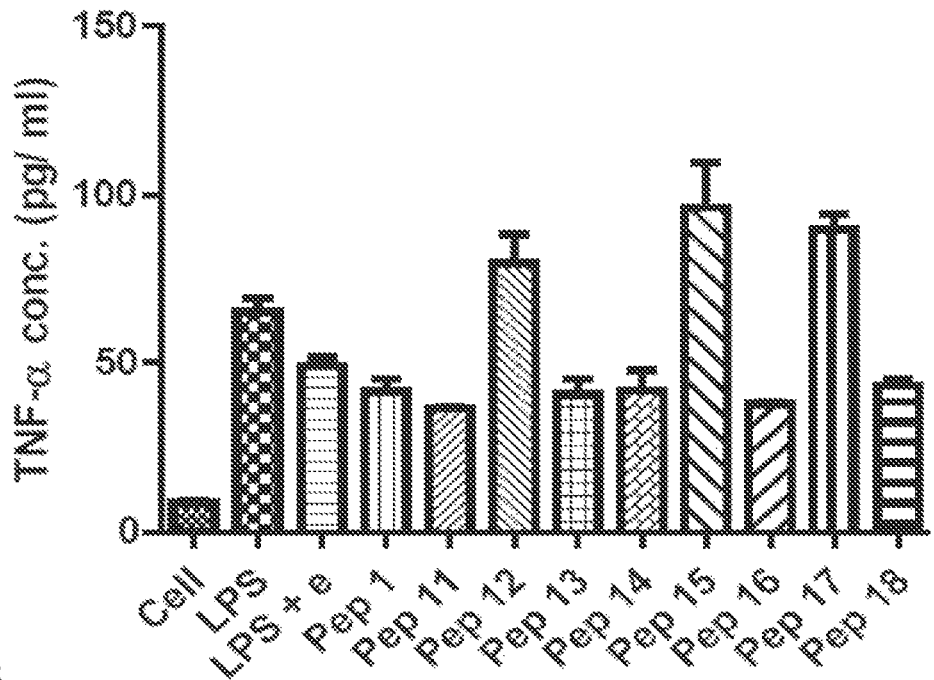
Figure 19:
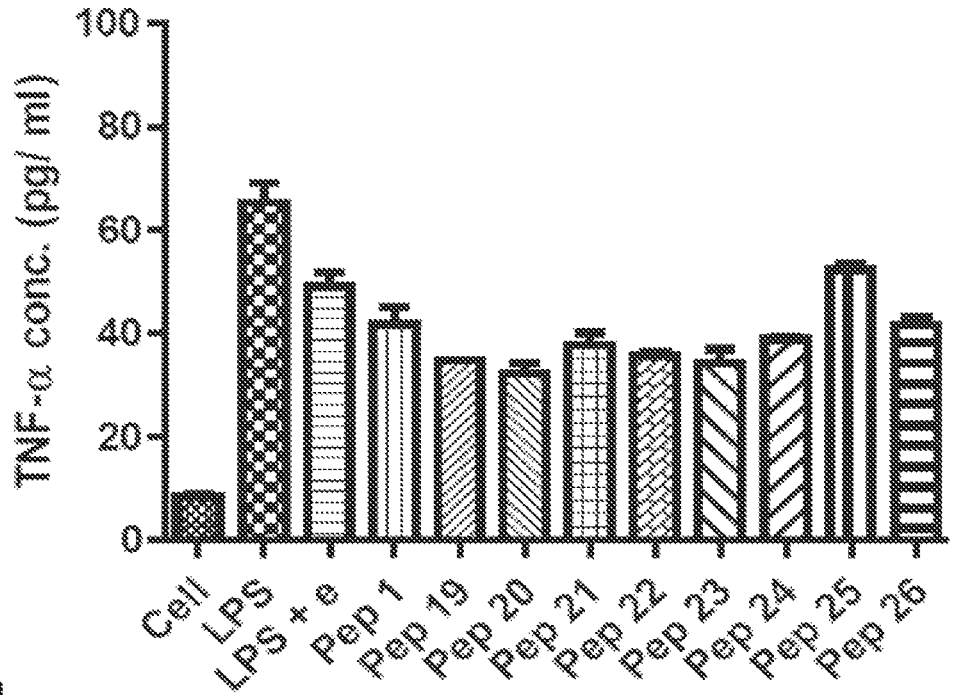
Figure 20:
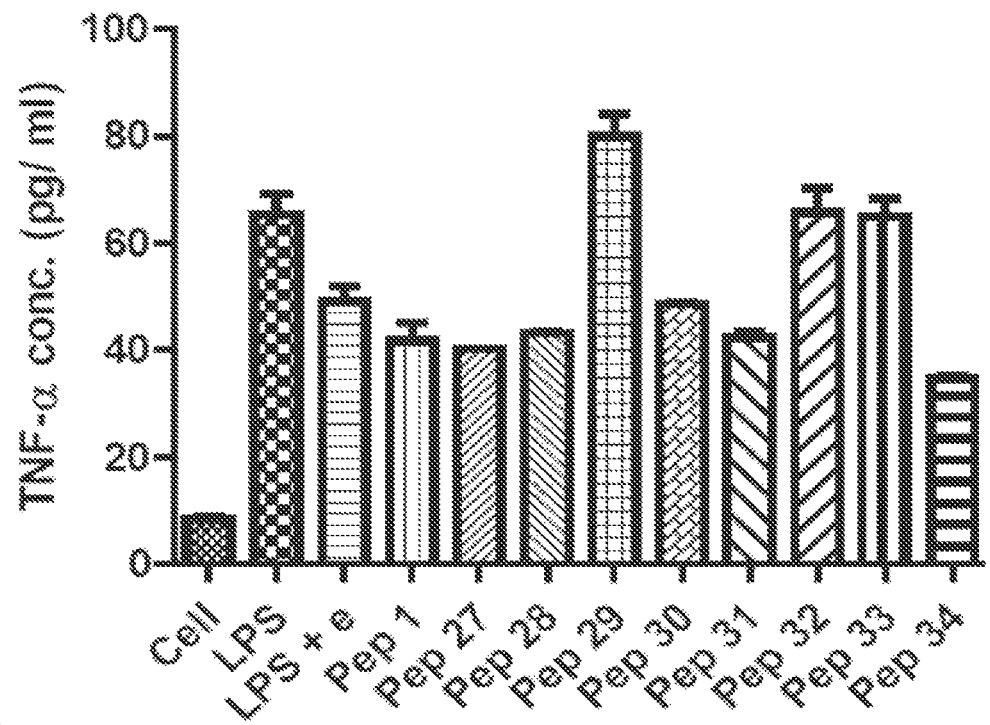
Figure 21:
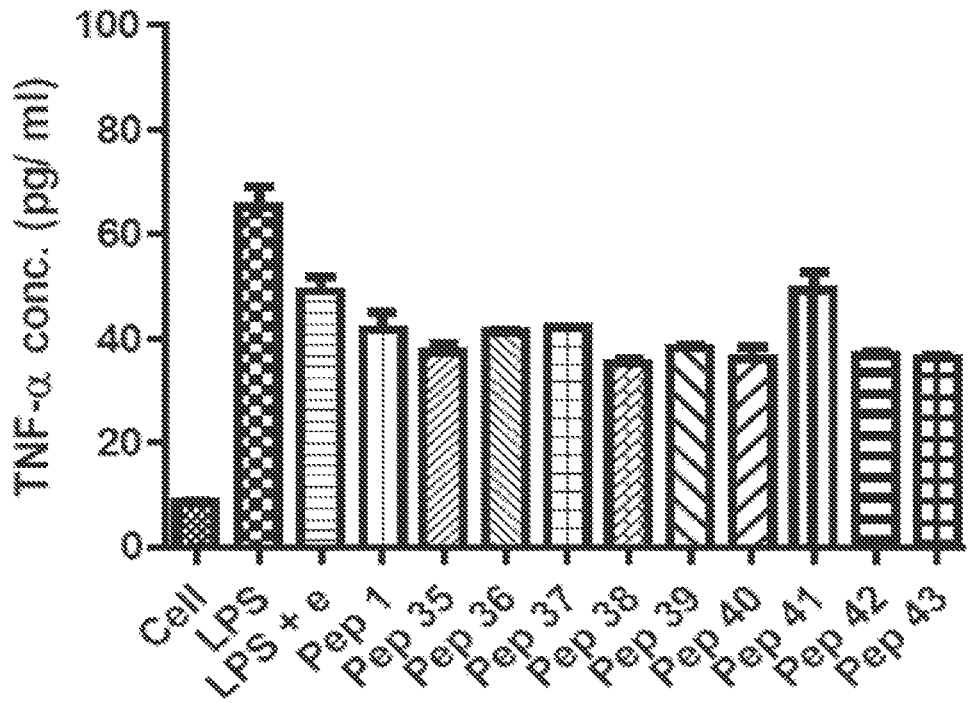
Figure 22:
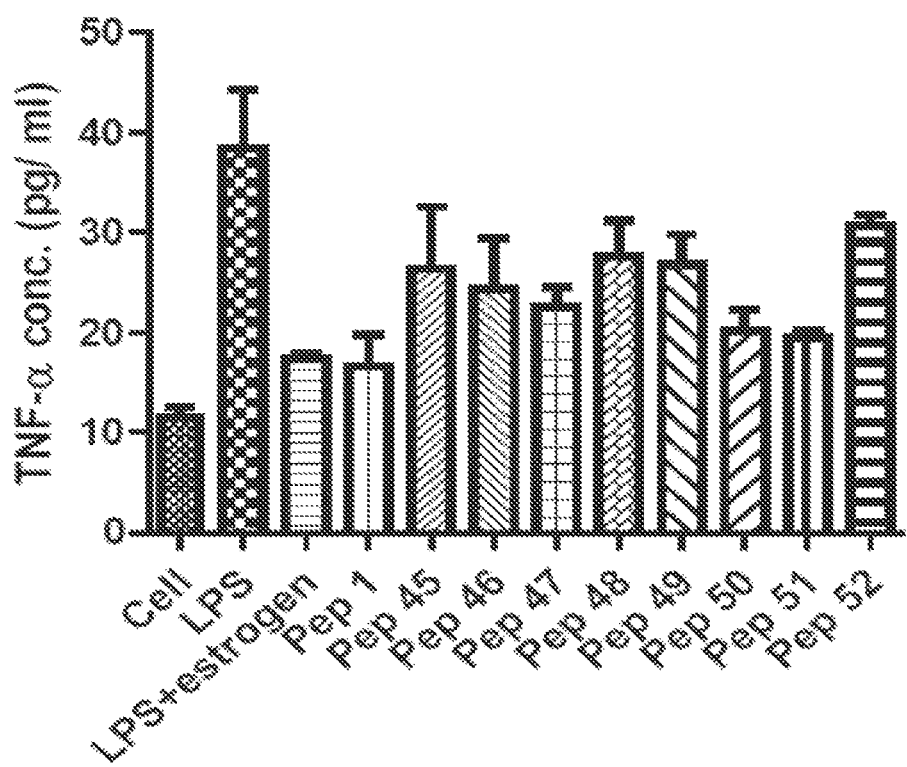
Figure 23:
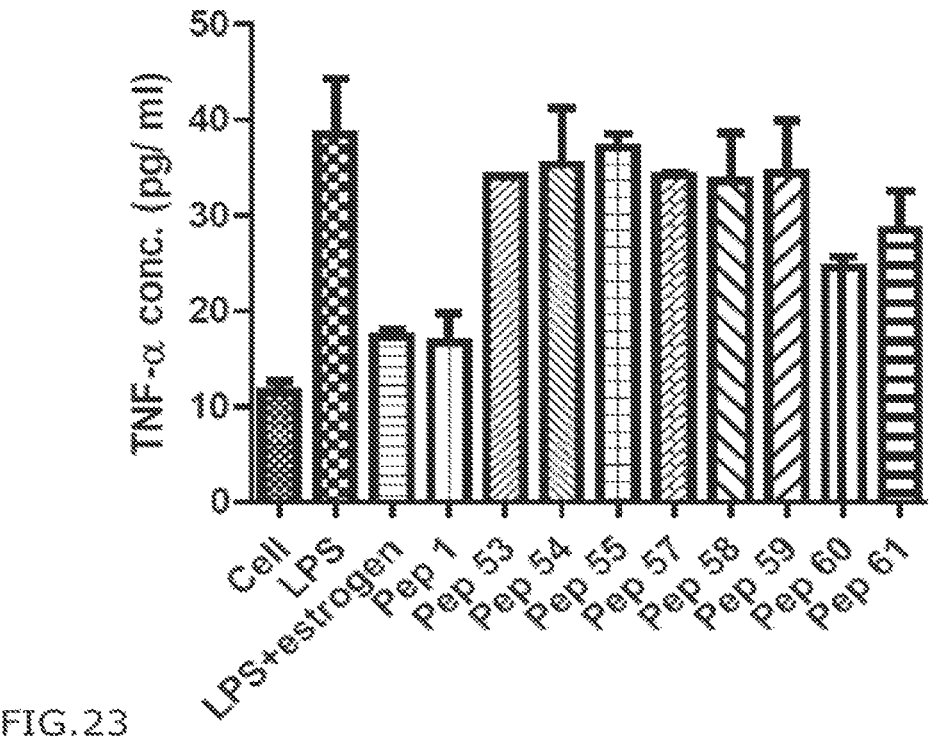
Figure 24:
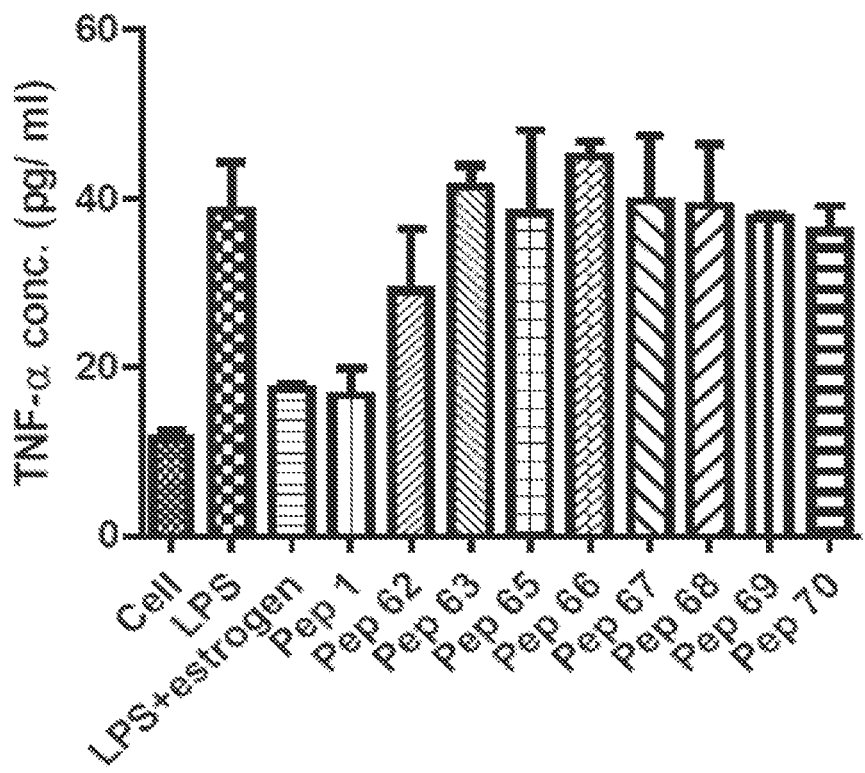
Figure 25:
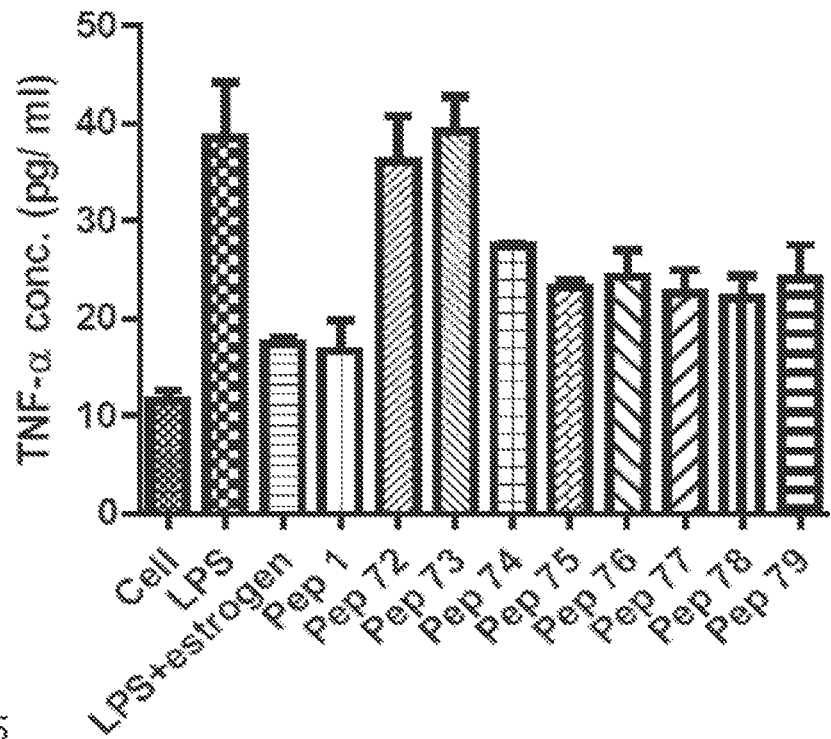
Figure 26:
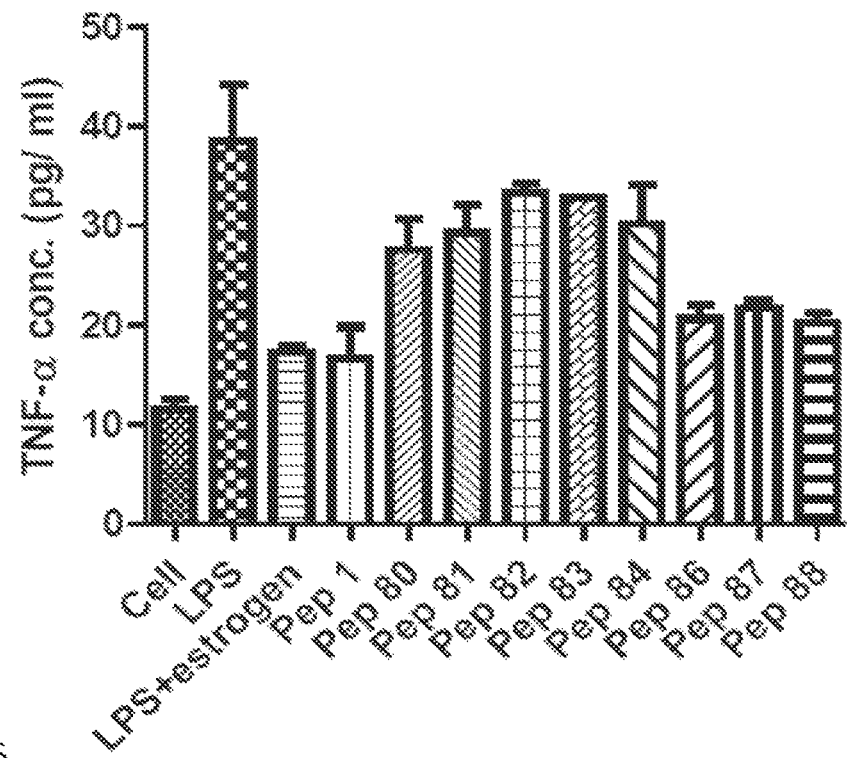
Figure 27:
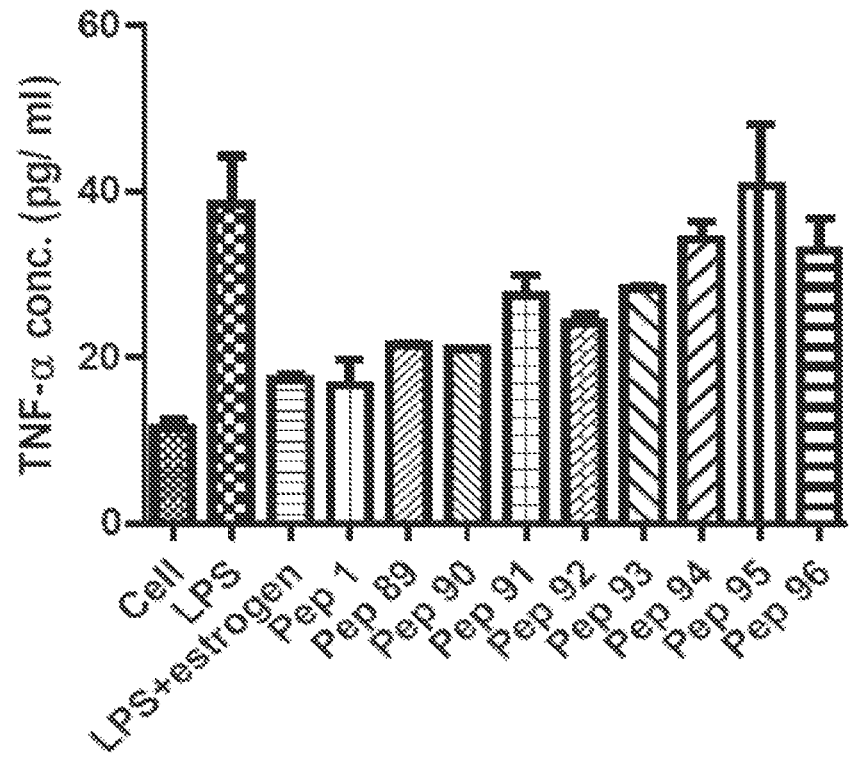
Figure 28:
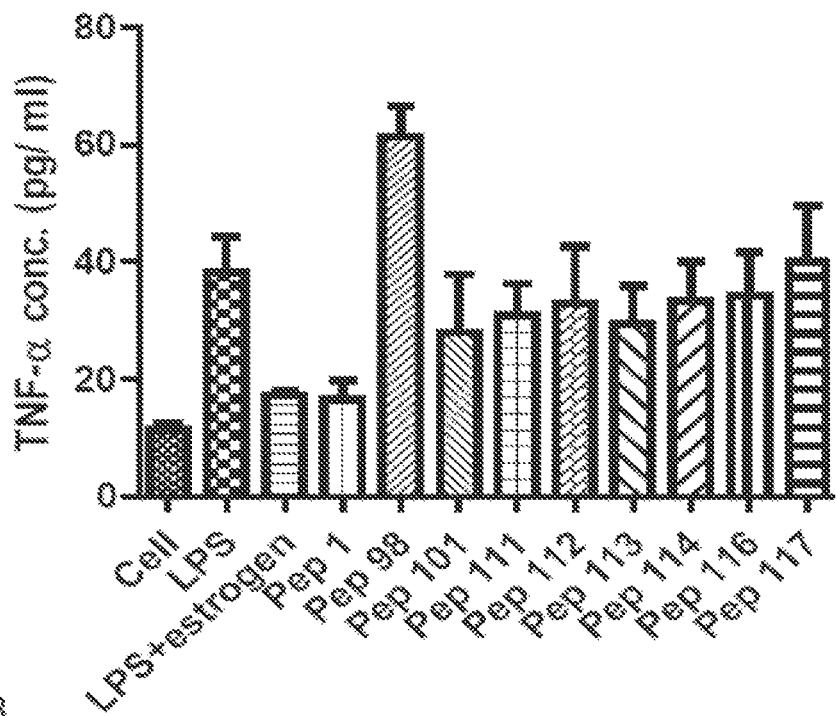
Figure 29:
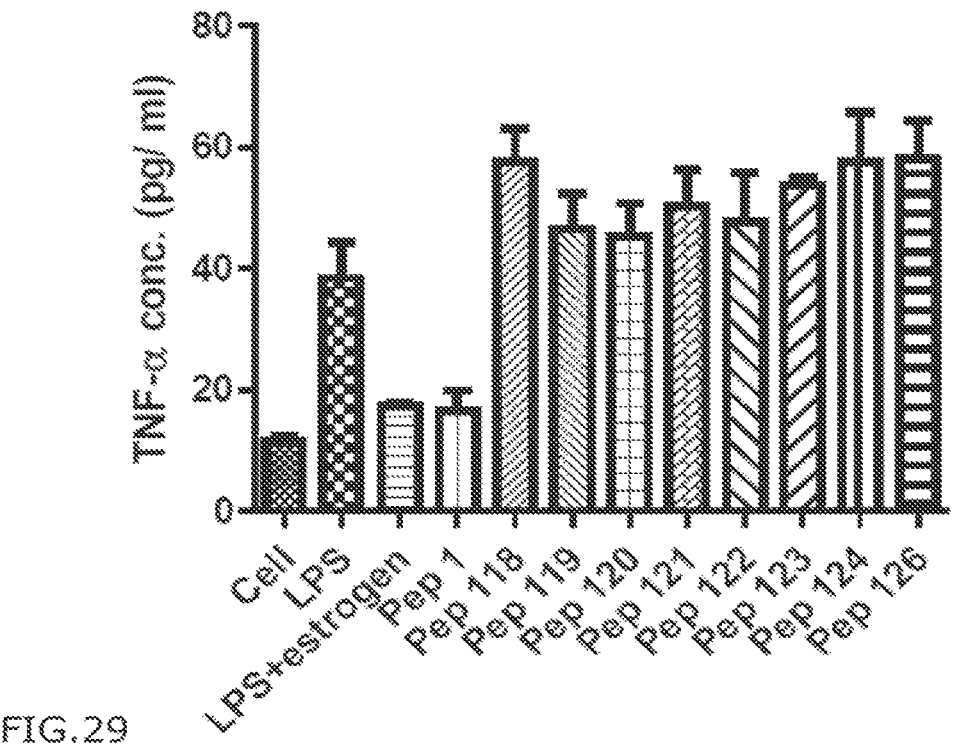
Figure 30:
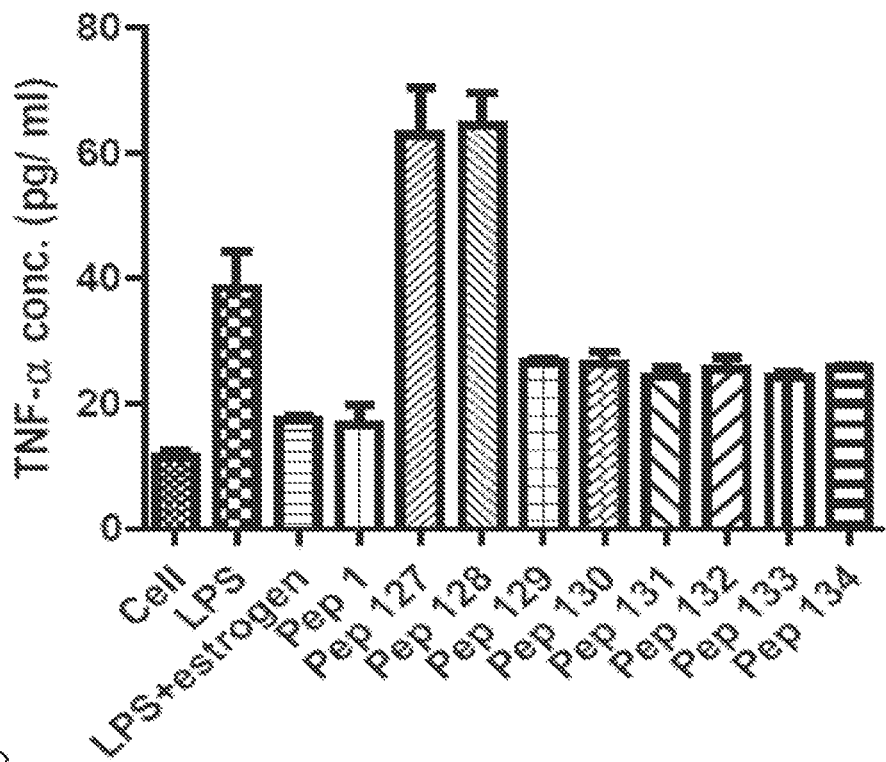
Figure 31:
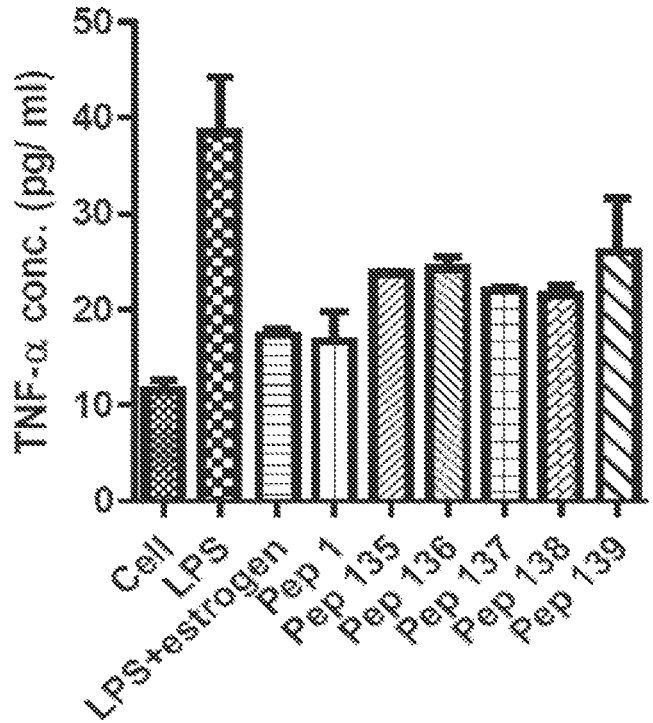
Figure 32:
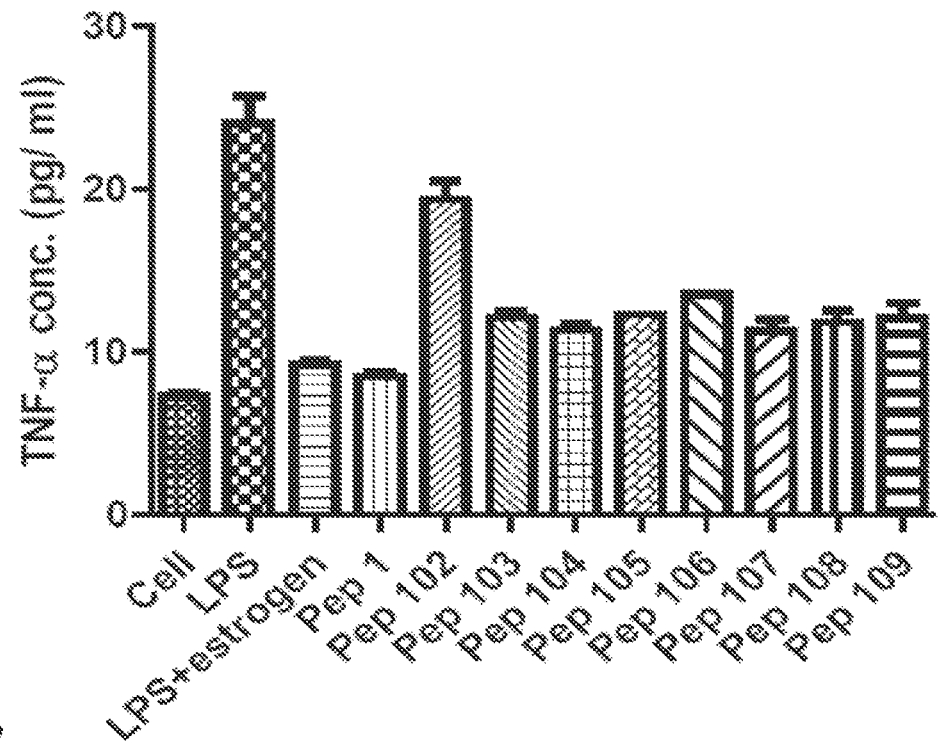
Figure 33:
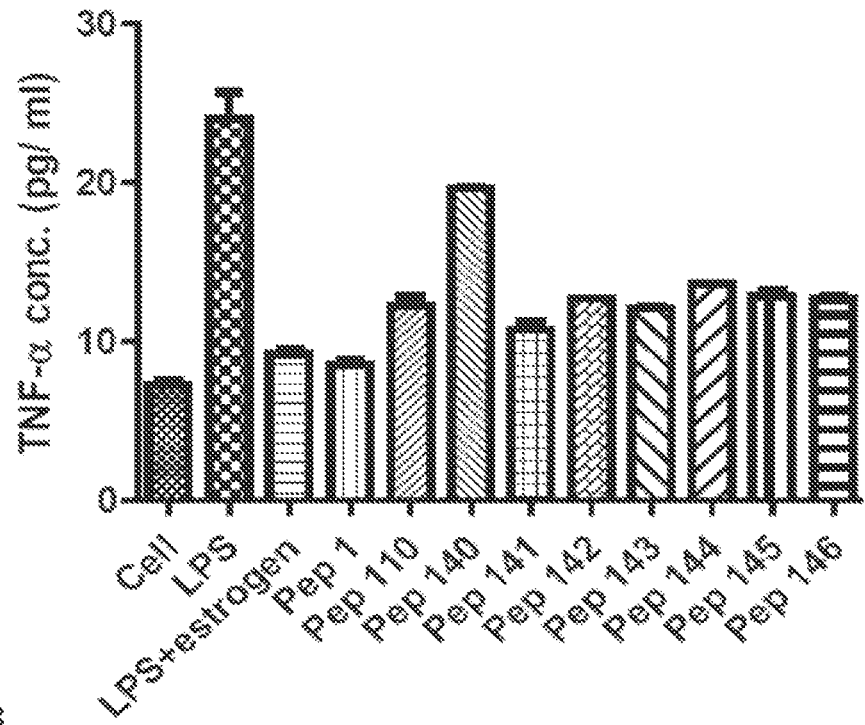
Figure 34:
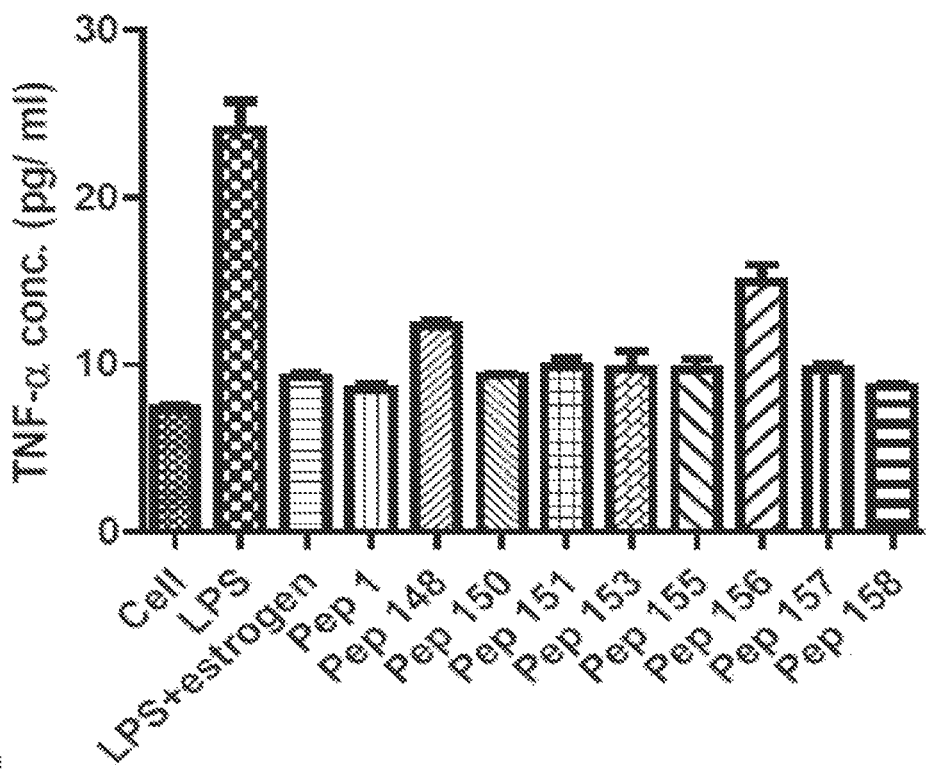
Figure 35:
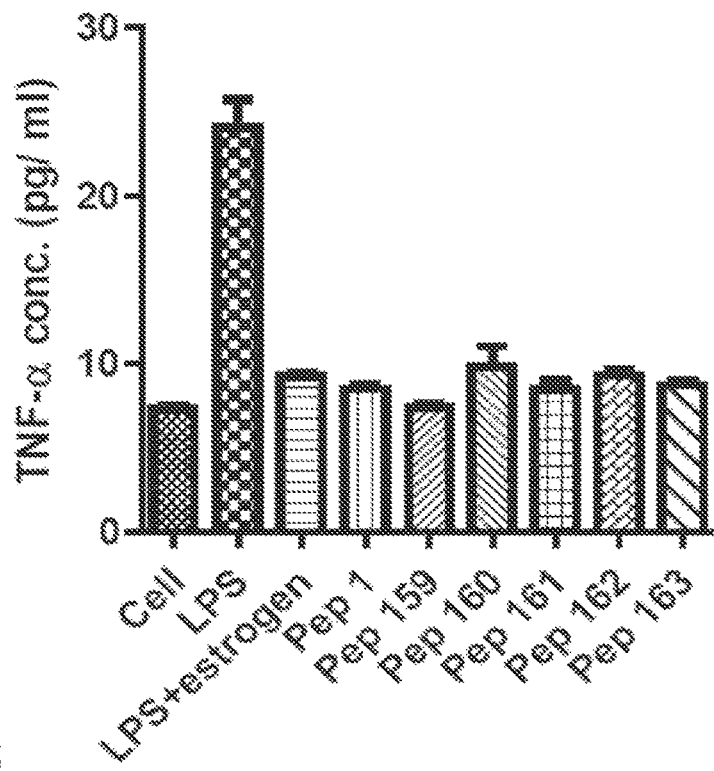

Since the present invention can have adaptability for diverse transformation and examples of practical application, below is a more detailed description of the present invention. Nevertheless, this is no means to limit the form of practical application; it should be understood that the intention is to include the concept and the extent of technology in all of the transformation, equivalents to alternatives. In describing the present invention, if any detailed description about the prior art is considered to deteriorate the fundamental principles of the present invention, the description will be omitted.

A telomere is known as a repetitive sequence of genetic material at the ends of chromosomes that prevent chromosomes from damage or merging of other chromosomes. The length of a telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells. The present invention was accomplished upon the discovery of telomerase-derived peptides with anti-inflammatory effects.

In one embodiment of the present invention, a peptide with anti-inflammatory activities is provided. The peptide comprises at least one amino acid sequence of SEQ ID NO: 1 to SEQ ID NO: 161, the peptide has above 80% homology with above-mentioned sequences, or the peptide is a fragment of the above-mentioned peptides.

The peptides described in SEQ ID NO: 1 to SEQ ID NO: 161 are as the following table 1. SEQ ID NO: 162 lists the order of full length of human telomerase protein. SEQ ID NO: 163 lists the telomerase-derived peptide that consists of 16 amino acid sequence.

The "name" in Table 1 below was used for distinction of peptides. In a different specific embodiment of the present invention, more than one peptide of the mentioned peptides in SEQ ID NO: 1 to SEQ ID NO: 161 comprise a "synthetic peptide", a synthesized peptide of selected areas of the telomerase. In the present specification, the term "pep" herein relates to a peptide that has any one of the SEQ ID NO: 1 to SEQ ID NO: 161, or, a peptide comprising of amino acid sequence above 80% homology with above-mentioned sequences, or a peptide fragment of above-mentioned peptides.

TABLE 1

| SEQ ID NO | NAME | POSITION IN TELOMERASE | SEQUENCE | LENGTH |
|---|---|---|---|---|
| 1. | pep2 | [660-689] | ALFSVLNYERARRPGLLGASVLGLDDIHRA | 30 aa |
| 2. | pep3 | [663-677] | SVLNYERARRPGLLG | 15 aa |
| 3. | pep4 | [674-683] | GLLGASVLGL | 10 aa |
| 4. | pep5 | [615-624] | ALLTSRLRFI | 10 aa |
| 5. | pep6 | [613-621] | RPALLTSRL | 9 aa |
| 6. | pep7 | [653-661] | RLTSRVKAL | 9 aa |
| 7. | pep8 | [691-705] | RTFVLRVRAQDPPPE | 15 aa |
| 8. | pep9 | [653-667] | RLTSRVKALFSVLNY | 15 aa |
| 9. | pep10 | [651-665] | AERLTSRVKALFSVL | 15 aa |
| 10. | pep11 | [667-675] | YERARRPGL | 9 aa |
| 11. | pep12 | [675-683] | LLGASVLGL | 9 aa |
| 12. | pep13 | [680-689] | VLGLDDIHRA | 10 aa |
| 13. | pep14 | [677-686] | GASVLGLDDI | 10 aa |
| 14. | pep15 | [660-669] | ALFSVLNYER | 10 aa |
| 15. | pep16 | [663-672] | SVLNYERARR | 10 aa |
| 16. | pep17 | [679-688] | SVLGLDDIHR | 10 aa |
| 17. | pep18 | [662-671] | FSVLNYERAR | 10 aa |
| 18. | pep19 | [666-675] | NYERARRPGL | 10 aa |
| 19. | pep20 | [667-676] | YERARRPGLL | 10 aa |
| 20. | pep21 | [672-681] | RPGLLGASVL | 10 aa |
| 21. | pep22 | [668-676] | ERARRPGLL | 9 aa |
| 22. | pep23 | [680-688] | VLGLDDIHR | 9 aa |
| 23. | pep24 | [663-671] | SVLNYERAR | 9 aa |
| 24. | pep25 | [664-672] | VLNYERARR | 9 aa |
| 25. | pep26 | [670-678] | ARRPGLLGA | 9 aa |
| 26. | pep27 | [673-681] | PGLLGASVL | 9 aa |
| 27. | pep28 | [671-679] | RRPGLLGAS | 9 aa |
| 28. | pep29 | [660-668] | ALFSVLNYE | 9 aa |
| 29. | pep30 | [674-682] | GLLGASVLG | 9 aa |
| 30. | pep31 | [679-687] | SVLGLDDIH | 9 aa |
| 31. | pep32 | [668-675] | ERARRPGL | 8 aa |
| 32. | pep33 | [670-677] | ARRPGLLG | 8 aa |
| 33. | pep34 | [674-681] | GLLGASVL | 8 aa |
| 34. | pep35 | [669-676] | RARRPGLL | 8 aa |
| 35. | pep36 | [676-683] | LGASVLGL | 8 aa |
| 36. | pep37 | [563-577] | VTETTFQKNRLFFYR | 15 aa |
| 37. | pep38 | [573-587] | LFFYRKSVWSKLQSI | 15 aa |
| 38. | pep39 | [583-597] | KLQSIGIRQHLKRVQ | 15 aa |
| 39. | pep40 | [603-617] | EAEVRQHREARPALL | 15 aa |

TABLE 1-continued

| SEQ ID NO | NAME | POSITION IN TELOMERASE SEQUENCE | | LENGTH |
|---|---|---|---|---|
| 40. | pep41 | [613-627] | RPALLTSRLRFIPKP | 15 aa |
| 41. | pep42 | [623-637] | FIPKPDGLRPIVNMD | 15 aa |
| 42. | pep43 | [643-657] | RTFRREKRAERLTSR | 15 aa |
| 43. | pep45 | [683-697] | LDDIHRAWRTFVLRV | 15 aa |
| 44. | pep46 | [693-707] | FVLRVRAQDPPPELY | 15 aa |
| 45. | pep47 | [721-735] | PQDRLTEVIASIIKP | 15 aa |
| 46. | pep48 | [578-592] | KSVWSKLQSIGIRQH | 15 aa |
| 47. | pep49 | [593-608] | LKRVQLRELSEAEVRQ | 16 aa |
| 48. | pep50 | [1-20] | MPRAPRCRAVRSLLRSHYRE | 20 aa |
| 49. | pep51 | [21-40] | VLPLATFVRRLGPQGWRLVQ | 20 aa |
| 50. | pep52 | [41-60] | RGDPAAFRALVAQCLVCVPW | 20 aa |
| 51. | pep53 | [61-80] | DARPPPAAPSFRQVSCLKEL | 20 aa |
| 52. | pep54 | [81-100] | VARVLQRLCERGAKNVLAFG | 20 aa |
| 53. | pep55 | [101-120] | FALLDGARGGPPEAFTTSVR | 20 aa |
| 54. | pep56 | [121-140] | SYLPNTVTDALRGSGAWGLL | 20 aa |
| 55. | pep57 | [141-160] | LRRVGDDVLVHLLARCALFV | 20 aa |
| 56. | pep58 | [161-180] | LVAPSCAYQVCGPPLYQLGA | 20 aa |
| 57. | pep59 | [181-200] | ATQARPPPHASGPRRRLGCE | 20 aa |
| 58. | pep60 | [201-220] | RAWNHSVREAGVPLGLPAPG | 20 aa |
| 59 | pep61 | [221-240] | ARRGGSASRSLPLPKRPRR | 20 aa |
| 60. | pep62 | [241-260] | GAAPEPERTPVGQGSWAHPG | 20 aa |
| 61. | pep63 | [261-280] | RTRGPSDRGFCVVSPARPAE | 20 aa |
| 62. | pep64 | [281-300] | EATSLEGALSGTRHSHPSVG | 20 aa |
| 63. | pep65 | [301-320] | RQHHAGPPSTSRPPRPWDTP | 20 aa |
| 64. | pep66 | [321-340] | CPPVYAETKHFLYSSGDKEQ | 20 aa |
| 65. | pep67 | [341-360] | LRPSFLLSSLRPSLTGARRL | 20 aa |
| 66. | pep68 | [361-380] | VETIFLGSRPWMPGTPRRLP | 20 aa |
| 67. | pep69 | [381-400] | RLPQRYWQMRPLFLELLGNH | 20 aa |
| 68. | pep70 | [401-420] | AQCPYGVLLKTHCPLRAAVT | 20 aa |
| 69. | pep71 | [421-440] | PAAGVCAREKPQGSVAAPEE | 20 aa |
| 70. | pep72 | [441-460] | EDTDPRRLVQLLRQHSSPWQ | 20 aa |
| 71. | pep73 | [461-480] | VYGFVRACLRRLVPPGLWGS | 20 aa |
| 72. | pep74 | [481-500] | RHNERRFLRNTKKFISLGKH | 20 aa |
| 73. | pep75 | [501-520] | AKLSLQELTWKMSVRDCAWL | 20 aa |
| 74. | pep76 | [521-540] | RRSPGVGCVPAAEHRLREEI | 20 aa |
| 75. | pep77 | [541-560] | LAKFLHWLMSVYVVELLRSF | 20 aa |
| 76. | pep78 | [561-580] | FYVTETTFQKNRLFFYRKSV | 20 aa |
| 77. | pep79 | [581-600] | WSKLQSIGIRQHLKRVQLRE | 20 aa |

TABLE 1-continued

| SEQ ID NO | NAME | POSITION IN TELOMERASE SEQUENCE | | LENGTH |
|---|---|---|---|---|
| 78. | pep80 | [601-620] | LSEAEVRQHREARPALLTSR | 20 aa |
| 79. | pep81 | [621-640] | LRFIPKPDGLRPIVNMDYVV | 20 aa |
| 80. | pep82 | [641-660] | GARTFRREKRAERLTSRVKA | 20 aa |
| 81. | pep83 | [661-680] | LFSVLNYERARRPGLLGASV | 20 aa |
| 82. | pep84 | [681-700] | LGLDDIHRAWRTFVLRVRAQ | 20 aa |
| 83. | pep85 | [701-720] | DPPPELYFVKVDVTGAYDTI | 20 aa |
| 84. | pep86 | [721-740] | PQDRLTEVIASIIKPQNTYC | 20 aa |
| 85. | pep87 | [741-760] | VRRYAVVQKAAHGHVRKAFK | 20 aa |
| 86. | pep88 | [761-780] | SHVSTLTDLQPYMRQFVAHL | 20 aa |
| 87. | pep89 | [781-800] | QETSPLRDAVVIEQSSSLNE | 20 aa |
| 88. | pep90 | [801-820] | ASSGLFDVFLRFMCHHAVRI | 20 aa |
| 89. | pep91 | [821-840] | RGKSYVQCQGIPQGSILSTL | 20 aa |
| 90. | pep92 | [841-860] | LCSLCYGDMENKLFAGIRRD | 20 aa |
| 91. | pep93 | [861-880] | GLLLRLVDDFLLVTPHLTHA | 20 aa |
| 92. | pep94 | [881-900] | KTFLRTLVRGVPEYGCVVNL | 20 aa |
| 93. | pep95 | [901-920] | RKTVVNFPVEDEALGGTAFV | 20 aa |
| 94. | pep96 | [921-940] | QMPAHGLFPWCGLLLDTRTL | 20 aa |
| 95. | pep97 | [941-960] | EVQSDYSSYARTSIRASLTF | 20 aa |
| 96. | pep98 | [961-980] | NRGFKAGRNMRRKLFGVLRL | 20 aa |
| 97. | pep99 | [981-1000] | KCHSLFLDLQVNSLQTVCTN | 20 aa |
| 98. | pep100 | [1001-1020] | IYKILLLQAYRFHACVLQLP | 20 aa |
| 99. | pep101 | [1021-1040] | FHQQVWKNPTFFLRVISDTA | 20 aa |
| 100. | pep102 | [1041-1060] | SLCYSILKAKNAGMSLGAKG | 20 aa |
| 101. | pep103 | [1061-1080] | AAGPLPSEAVQWLCHQAFLL | 20 aa |
| 102. | pep104 | [1081-1100] | KLTRHRVTYVPLLGSLRTAQ | 20 aa |
| 103. | pep105 | [1101-1120] | TQLSRKLPGTILTALEAAAN | 20 aa |
| 104. | pep106 | [1121-1132] | PALPSDFKTILD | 12 aa |
| 105. | pep107 | [1-10] | MPRAPRCRAV | 10 aa |
| 106. | pep108 | [11-30] | RSLLRSHYREVLPLATFVRR | 20 aa |
| 107. | pep109 | [31-50] | LGPQGWRLVQRGDPAAFRAL | 20 aa |
| 108. | pep110 | [51-70] | VAQCLVCVPWDARPPPAAPS | 20 aa |
| 109. | pep111 | [71-90] | FRQVSCLKELVARVLQRLCE | 20 aa |
| 110. | pep112 | [91-110] | RGAKNVLAFGFALLDGARGG | 20 aa |
| 111. | pep113 | [111-130] | PPEAFTTSVRSYLPNTVTDA | 20 aa |
| 112. | pep114 | [131-150] | LRGSGAWGLLLRRVGDDVLV | 20 aa |
| 113. | pep115 | [151-170] | HLLARCALFVLVAPSCAYQV | 20 aa |
| 114. | pep116 | [171-190] | CGPPLYQLGAATQARPPPHA | 20 aa |
| 115. | pep117 | [191-210] | SGPRRRLGCERAWNHSVREA | 20 aa |
| 116. | pep118 | [211-230] | GVPLGLPAPGARRRGGSASR | 20 aa |

TABLE 1-continued

| SEQ ID NO | NAME | POSITION IN TELOMERASE SEQUENCE | | LENGTH |
|---|---|---|---|---|
| 117. | pep119 | [231-250] | SLPLPKRPRRGAAPEPERTP | 20 aa |
| 118. | pep120 | [251-270] | VGQGSWAHPGRTRGPSDRGF | 20 aa |
| 119. | pep121 | [271-290] | CVVSPARPAEEATSLEGALS | 20 aa |
| 120. | pep122 | [291-310] | GTRHSHPSVGRQHHAGPPST | 20 aa |
| 121. | pep123 | [311-330] | SRPPRPWDTPCPPVYAETKH | 20 aa |
| 122. | pep124 | [331-350] | FLYSSGDKEQLRPSFLLSSL | 20 aa |
| 123. | pep125 | [351-370] | RPSLTGARRLVETIFLGSRP | 20 aa |
| 124. | pep126 | [371-390] | WMPGTPRRLPRLPQRYWQMR | 20 aa |
| 125. | pep127 | [391-410] | PLFLELLGNHAQCPYGVLLK | 20 aa |
| 126. | pep128 | [411-430] | THCPLRAAVTPAAGVCAREK | 20 aa |
| 127. | pep129 | [431-450] | PQGSVAAPEEEDTDPRRLVQ | 20 aa |
| 128. | pep130 | [451-470] | LLRQHSSPWQVYGFVRACLR | 20 aa |
| 129. | pep131 | [471-490] | RLVPPGLWGSRHNERRFLRN | 20 aa |
| 130. | pep132 | [491-510] | TKKFISLGKHAKLSLQELTW | 20 aa |
| 131. | pep133 | [511-530] | KMSVRDCAWLRRSPGVGCVP | 20 aa |
| 132. | pep134 | [531-550] | AAEHRLREEILAKFLHWLMS | 20 aa |
| 133. | pep135 | [551-570] | VYVVELLRSFFYVTETTFQK | 20 aa |
| 134. | pep136 | [571-590] | NRLFFYRKSVWSKLQSIGIR | 20 aa |
| 135. | pep137 | [591-610] | QHLKRVQLRELSEAEVRQHR | 20 aa |
| 136. | pep138 | [611-630] | EARPALLTSRLRFIPKPDGL | 20 aa |
| 137. | pep139 | [631-650] | RPIVNMDYVVGARTFRREKR | 20 aa |
| 138. | pep140 | [651-670] | AERLTSRVKALFSVLNYERA | 20 aa |
| 139. | pep141 | [671-690] | RRPGLLGASVLGLDDIHRAW | 20 aa |
| 140. | pep142 | [691-710] | RTFVLRVRAQDPPPELYFVK | 20 aa |
| 141. | pep143 | [711-730] | VDVTGAYDTIPQDRLTEVIA | 20 aa |
| 142. | pep144 | [731-750] | SIIKPQNTYCVRRYAVVQKA | 20 aa |
| 143. | pep145 | [751-770] | AHGHVRKAFKSHVSTLTDLQ | 20 aa |
| 144. | pep146 | [771-790] | PYMRQFVAHLQETSPLRDAV | 20 aa |
| 145. | pep147 | [791-810] | VIEQSSSLNEASSGLFDVFL | 20 aa |
| 146. | pep148 | [811-830] | RFMCHHAVRIRGKSYVQCQG | 20 aa |
| 147. | pep149 | [831-850] | IPQGSILSTLLCSLCYGDME | 20 aa |
| 148. | pep150 | [851-870] | NKLFAGIRRDGLLLRLVDDF | 20 aa |
| 149. | pep151 | [871-890] | LLVTPHLTHAKTFLRTLVRG | 20 aa |
| 150. | pep152 | [891-910] | VPEYGCVVNLRKTVVNFPVE | 20 aa |
| 151. | pep153 | [911-930] | DEALGGTAFVQMPAHGLFPW | 20 aa |
| 152. | pep154 | [931-950] | CGLLLDTRTLEVQSDYSSYA | 20 aa |
| 153. | pep155 | [951-970] | RTSIRASLTFNRGFKAGRNM | 20 aa |
| 154. | pep156 | [971-990] | RRKLFGVLRLKCHSLFLDLQ | 20 aa |

TABLE 1-continued

| SEQ ID NO | NAME | POSITION IN TELOMERASE | SEQUENCE | LENGTH |
|---|---|---|---|---|
| 155. | pep157 | [991-1010] | VNSLQTVCTNIYKILLLQAY | 20 aa |
| 156. | pep158 | [1011-1030) | RFHACVLQLPFHQQVWKNPT | 20 aa |
| 157. | pep159 | [1031-1050) | FFLRVISDTASLCYSILKAK | 20 aa |
| 158. | pep160 | [1051-1070] | NAGMSLGAKGAAGPLPSEAV | 20 aa |
| 159. | pep161 | [1071-1090] | QWLCHQAFLLKLTRHRVTYV | 20 aa |
| 160. | pep162 | [1091-1110] | PLLGSLRTAQTQLSRKLPGT | 20 aa |
| 161. | pep163 | [1111-1132] | TLTALEAAANPALPSDFKTILD | 22 aa |
| 162. | Telomerase | [1-1132] | MPRAPRCRAVRSLLRSHYREVLPLATFVRR LGPQGWRLVQRGDPAAFRALVAQCLVCVPW DARPPPAAPSFRQVSCLKELVARVLQRLCERG AKNVLAFGFALLDGARGGPPEAFTTSVRSYLP NTVTDALRGSGAWGLLLRRVGDDVLVHLLAR CALFVLVAPSCAYQVCGPPLYQLGAATQARPP PHASGPRRRLGCERAWNHSVREAGVPLGLPA PGARRRGGSASRSLPLPKRPRRGAAPEPERTP VGQGSWAHPGRTRGPSDRGFCVVSPARPAE EATSLEGALSGTRHSHPSVGRQHHAGPPSTS RPPRPWDTPCPPVYAETKHFLYSSGDKEQLR PSFLLSSLRPSLTGARRLVETIFLGSRPWMPG TPRRLPRLPQRYWQMRPLFLELLGNHAQCPY GVLLKTHCPLRAAVTPAAGVCAREKPQGSVA APEEEDTDPRRLVQLLRQHSSPWQVYGFVRA CLRRLVPPGLWGSRHNERRFLRNTKKFISLG KHAKLSLQELTWKMSVRDCAWLRRSPGVGC VPAAEHRLREEILAKFLHWLMSVYVVELLRSF FYVTETTFQKNRLFFYRKSVWSKLQSIGIRQH LKRVQLRELSEAEVRQHREARPALLTSRLRFI PKPDGLRPIVNMDYVVGARTFRREKRAERLT SRVKALFSVLNYERARRPGLLGASVLGLDDIH RAWRTFVLRVRAQDPPPELYFVKVDVTGAYD TIPQDRLTEVIASIIKPQNTYCVRRYAVVQKA AHGHVRKAFKSHVSTLTDLQPYMRQFVAHLQ ETSPLRDAVVIEQSSSLNEASSGLEDVFLRFM CHHAVRIRGKSYVQCQGIPQGSILSTLLCSLC YGDMENKLFAGIRRDGLLLRLVDDFLLVTPHL THAKTFLRTLVRGVPEYGCVVNLRKTVVNFPV EDEALGGTAFVQMPAHGLFPWCGLLLDTRTL EVQSDYSSYARTSIRASLTFNRGFKAGRNMR RKLFGVLRLKCHSLFLDLQVNSLQTVCTNIYK ILLLQAYRFHACVLQLPFHQQVWKNPTFFLRV ISDTASLCYSILKAKNAGMSLGAKGAAGPLPS EAVQWLCHQAFLLKLTRHRVTYVPLLGSLRTA QTQLSRKLPGTTLTALEAAANPALPSDFKTIL D | 1132 aa |
| 163. | pep 1 | [611-626] | EARPALLTSRLRFIPK | 16 aa |

In one embodiment of the present invention, a polynucleotide that codes a peptide with anti-inflammatory activities is provided. The polynucleotide codes a peptide comprising at least one amino acid sequence of SEQ ID NO: 1 to SEQ ID NO: 161, a peptide having above 80% homology with above-mentioned sequences, or a peptide being a fragment of the above-mentioned peptides. The polynucleotide mentioned above enables production of the peptides in large quantities. For example, cultivation of vectors that include polynucleotides encoding peptides allows production of peptides in large quantities.

The peptides disclosed herein can Include a peptide comprising amino acid sequence above 80%, above 85%, above 90%, above 95%, above 96%, above 97%, above 98%, or above 99% homology. Moreover, the peptides disclosed In the present invention can include a peptide comprising SEQ ID NO: 1 or its fragments, and a peptide with more than 1 transformed amino acid, more than 2 transformed amino acid, more than 3 transformed amino acid, more than 4 transformed amino acid, more than 5 transformed amino acid, more than 6 transformed amino acid, or more than 7 transformed amino acid.

In the present specification and claims, the terms "homology" and "sequence identity" are used interchangeably to indicate the degree of sequence overlap between two amino acid (or if relevant: nucleic acid) sequences.

Unless otherwise stated the term "Sequence identity" for peptides as used herein refers to the sequence identity calculated as $(n_{ref}-n_{dif}) \cdot 100/n_{ref}$, wherein $n_{dif}$ is the total number of non-identical residues in the two sequences when aligned so that a maximum number of amino acids are identical and wherein $n_{ref}$ is the number of residues in the shortest of the sequences. Hence, the DNA sequence agtcagtc will have a sequence identity of 75% with the sequence aatcaatc ($n_{dif}=2$ and $n_{ref}=8$).

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

In one embodiment of the present invention, changes in amino acid sequence belong to the modification of peptide's physical and chemical characteristics. For example, amino acid transformation can be performed by improving thermal stability of the peptide, altering substrate specificity, and changing the optimal pH.

In one embodiment of the present invention, a peptide comprising amino acid sequence of at least one of SEQ ID NO: 1 to SEQ ID NO: 161, a peptide comprising of amino acid sequence above 80% homology with above-mentioned sequences, or a peptide fragment of above-mentioned peptides is preferably made of 30 or less amino acids.

In one embodiment of the present invention, a peptide comprising amino acid sequence of at least one of SEQ ID NO: 1 to SEQ ID NO: 161, a peptide comprising of amino acid sequence above 80% homology with above-mentioned sequences, or a peptide fragment of above-mentioned peptides comprises a peptide originages from telomerase, more specifically, telomerase of Homo sapiens.

The term "amino acid" herein includes not only the 22 standard amino acids that are naturally integrated into peptide but also the D-Isomers and transformed amino acids. Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, plamitoylation), alkylation, carboxylation, hydroxylation, glycation, biotinylation, ubiquitinylation, transformation in chemical properties (e.g. β-removing deimidation, deamidation) and structural transformation (e.g. formation of disulfide bridge). Also, changes of amino acids are included and the changes of amino acids occur due to chemical reaction during the combination process with crosslinkers for formation of a peptide conjugate.

A peptide disclosed herein may be a wild-type peptide that has been identified and isolated from natural sources. On the other hand, when compared to peptide fragments of SEQ ID NO: 1, the peptides disclosed herein may be artificial mutants that comprise one or more substituted, deleted and/or inserted amino acids. Amino acid alteration in wild-type polypeptide—not only in artificial mutants—comprises conservative substitution of amino acids that do not influence protein folding and or activation. Examples of conservative substitution belong to the group consisting of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activity are known in the art of the present invention. Most common occurred alteration are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations. Another example of conservative substitutions are shown in the following table 2.

TABLE 2

| Original amino acid | Examples of residue substitution | Preferable residue substitution |
|---|---|---|
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial transformation of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:

(1) hydrophobicity: Norleucine, met, ala, vat, leu, ile;
(2) neutral hydrophilicity: cys, ser, thr;
(3) acidity: asp, glu;
(4) basicity: asn, gln, his, lys arg;
(5) residue that affects chain orientation: gly, pro; and
(6) aromaticity: trp, tyr, phe.

Non-conservative substitutions may be performed by exchanging a member of the above classes to that of a different class. Any cysteine residues that are not related in maintaining the proper three-dimensional structure of the peptide can typically be substituted into serine, thus increasing the oxidative stability of the molecule and preventing improper crosslinkage. Conversely, improvement of stability can be achieved by adding cysteine bond(s) to the peptide.

Altered types of amino acids variants of peptides are those that antibody glycosylation pattern changed. The term "change" herein relates to deletion of carbohydrate residues and/or addition of at least one glycosylated residues that do not exist within a peptide.

Glycosylation in peptides are typically N-connected or O-connected. The term "N-connected" herein relates to that carbohydrate residues are attached to the side chain of asparagine residues. As tripeptide sequences, asparagine-X-serine and asparagine-X-threonine (where the X is any amino acid except proline) are the recognition sequence for attaching carbohydrate residue enzymatically to the side chain of asparagine. Therefore, with the presence of one of these tripeptide sequences in a polypeptide, the potential glycosylation sites are created. "O-connected glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing amino acid sequence to contain tripeptide sequence mentioned above (for N-linked glycosylation sites). These changes may be made by addition of at least one serine or theronine residues to the first antibody sequence, or by substitution with those residues (for O-linked glycosylation sites).

In one embodiment of the present invention, a polynucleotide is a nucleic acid molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those.

A HMGB1 protein is known as a cytokine. It first undergoes acetylation and translocation to cytoplasm by external stimulation. Then it is secreted out of the cell, therefore serving the role of inflammation-causing cytokine. Because when one has an inflammation due to such activity, HMGB1 protein is secreted out of the cell, and patients with inflammatory diseases such as Churg strauss syndrome, rheumatoid arthritis and Sjogren's syndrome will present with elevated serum levels of HMGB1. Hence, if nucleus contains large amount of HMGB1 even when there is a stimulus that causes inflammation, it is suggestive of the fact that HMGB1 is not being secreted out of the cell, which means inflammation is being suppressed.

In one embodiment of the present invention, when treated a cell with a peptide comprising any one amino acid sequence of SEQ ID NO: 1 to SEQ ID NO: 161, a peptide having above 80% homology of amino acid sequence with above-mentioned sequences, or a fragment of the above-mentioned peptides, amount of HMGB1 within the nucleus increases. This represents that the peptides mentioned above have excellent inflammation preventive or suppressive effects.

Also, in specific embodiments of the present invention, a peptide comprising any one amino acid sequence of SEQ ID NO: 1 to SEQ ID NO: 161, a peptide having above 80% homology of amino acid sequence with above-mentioned sequences, or a fragment of the above-mentioned peptides, has an advantage in that it has high feasibility due to its low toxicity within a cell.

In the present invention, an "inflammatory disease" is a broad indication that refers to any disease that designates inflammation as a main cause or inflammation caused by disease. Specifically, an inflammatory disease includes (1) general or localized inflammatory disease (for example, allergies; immune-complex disease; hayfever; hypersensitive shock; endotoxin shock; cachexia, hyperthermia; granulomatosis; or sarcoidosis); (2) gastro-intestinal related diseases (for example, appendicitis; gastric ulcer; duodenal ulcer; peritonitis; pancreatitis; ulcerative, acute, or ischemic colitis; cholangitis; cholecystitis, steatorrhea, hepatitis, Crone's disease; or Whipple's Disease); (3) dermal related diseases (for example, psoriasis; burns; sunburns; dermatitis; Urticarial warts or wheal); (4) vascular related diseases (for example, angiitis; vasculitis; endocarditis; arteritis; atherosclerosis; thrombophlebitis; pericarditis; congestive heart failure; myocarditis; myocardial ischemia; periarteritis nodosa; recurrent stenosis; Buerger's disease; or rheumatic fever); (5) respiratory diseases (for example, asthma; epiglottitis; bronchitis; emphysema; rhinitis; cystic fibrosis; interstitial pneumonitis; COPD (chronic obstructive pulmonary disease); adult respiratory distress syndrome; coniosis; alveolitis; bronchiolitis; pharyngitis; pleurisy; or sinusitis); (6) bone, joint, muscle and connective tissue related diseases (for example, eosinophilic granuloma; arthritis; arthralgia; osteomyelitis; dermatomyositis; fasciitis; Paget's disease; gout; periodontal disease; rheumatoid arthritis; myasthenia gravis; ankylosing spondylitis; or synovitis); (7) urogenital disorders (for example, epididymitis; vaginitis; prostatitis; or urethritis); (8) central or peripheral nervous system related diseases (for example, Alzheimer's disease; meningitis; encephalitis; multiple sclerosis; cerebral infarction; cerebral embolism; Guillain-Barre syndrome; neuritis; neuralgia; spinal cord injury; paralysis; or uveitis); (9) virus (for example, influenza; respiratory syncytial virus; HIV; hepatitis B; hepatitis C; or herpes virus), infectious disease (for example, Dengue fever; or septicemia), fungal infection (for example, candidiasis); or bacterial, parasitic, and similar microbial infection (for example, disseminated bacteremia; malaria; onchocerciasis; or amebiasis); (10) autoimmune disease (for example, thyroiditis; lupus; Goodpasture's syndrome; allograft rejection; graft versus host disease; or diabetes); and (11) cancer or tumor disease (for example, Hodgkin's disease), but not limited to those.

Treating the inflammatory component of such diseases has been a major goal of the global pharmaceutical industry for a number of decades, and a wide variety of useful treatments have been developed. Examples include the corticosteroids (a range of natural, semisynthetic and synthetic agents designed to mimic the effect of cortisol, including prednisolone, methylprednisolone, dexamethasone, betamethasone, fluticasone and so forth), cyclooxygenase inhibitors (both non-selective or cox-1 selective, such as indomethacin, sulfasalzine and aspirin, and more recently cox-2 selective, such as celecoxib), leukotriene blockers (such as monteleukast) and anti-TNFs (such as modified monoclonal neutralising antibodies, including infliximab (Remicade™)

and adalimumab (Humira™), TNF receptor fusion proteins, such as etanercept (Enbrel™), as well as small molecule TNF-α synthesis inhibitors like thalidomide).

In one embodiment of the present invention, an anti-inflammatory composition comprising a peptide as an active ingredient is provided. The peptide comprises at least one amino acid sequence of SEQ ID NO: 1 to SEQ ID NO: 161, the peptide has above 80% homology with above-mentioned sequences, or the peptide is a fragment of the above-mentioned peptides.

In one embodiment of the present invention, the anti-inflammatory composition may contain 0.1 µg/mg to 1 mg/mg, specifically 1 µg/mg to 0.5 mg/mg, more specifically 10 µg/mg to 0.1 mg/mg of a peptide comprising of amino acid sequence of at least one of SEQ ID NO: 1 to SEQ ID NO: 161, a peptide comprising of amino acid sequence above 80% homology with above-mentioned sequences, or peptide fragment of above-mentioned peptides. When the peptide is contained in the above mentioned range, all the safety and stability of the composition may be satisfied and appropriate in terms of cost-effectiveness.

In one embodiment of the present invention, the composition may have application with all animals including human, dog, chicken, pig, cow, sheep, guinea pig, and monkey.

In one embodiment of the present invention, the medical composition for the use of treatment or prophylaxis of Inflammatory disease with an active ingredient that is comprised of a peptide consisting of an amino acid sequence from SEQ ID NO: 1 to SEQ ID NO: 161, a peptide comprising of amino acid sequence above 80% homology with above-mentioned sequences, or peptide fragment of SEQ ID NO:1, is provided. In one embodiment of the present invention, the pharmaceutical composition may be administered through oral, rectal, transdermal, intravenous, intramuscular, intraperitoneal, in the bone marrow, epidural or subcutaneous means.

Forms of oral administration may be, but not limited to, tablets, pills, soft or hard capsules, granules, powders, solution, or emulsion. Forms of non-oral administration may be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition can be manufactured by conventional methods of the industry in the art.

In one embodiment of the present invention, the active ingredient of the medical composition may vary according to the patient's age, sex, weight, pathology and state, administration route, or prescriber's judgment. Dosage based on these factors is determined within levels of those skilled in the art, and the daily dose for example may be, but not limited to, 0.1 µg/kg/day to 1 g/kg/day, specifically 1 µg/kg/day to 10 mg/kg/day, more specifically 10 µg/kg/day to 1 mg/kg/day, more specifically 50 µg/kg/day to 100 µg/kg/day.

In one embodiment of the present invention, the pharmaceutical composition may be administered, but not limited to, 1 to 3 times a day.

In one embodiment of the present invention, a skin external composition for improvement or prevention of skin inflammation is provided. The skin external composition may contain an active ingredient that is a peptide comprising of an amino acid sequence from SEQ ID NO: 1 to SEQ ID NO: 161, a peptide comprising of amino acid sequence above 80% homology with above-mentioned sequences, or peptide fragment of above-mentioned peptides.

In another embodiment of the present invention, a cosmetic composition for improvement or prevention of skin inflammation is provided. The cosmetic composition may contain an active ingredient that is a peptide comprising of an amino acid sequence from SEQ ID NO: 1 to SEQ ID NO: 161, a peptide comprising of amino acid sequence above 80% homology with above-mentioned sequences, or peptide fragment of above-mentioned peptides.

In one embodiment of the present invention, external application composition or cosmetic composition may be provided in all forms appropriate for topical applications. For example, forms can be provided as solutions, emulsions obtained by dispersion of oil phase in water, emulsion obtained by dispersion of water in oil phase, suspension, solid, gel, powder, paste, foam or aerosol. These forms can be manufactured by conventional methods of the industry in the art.

In one embodiment of the present invention, the cosmetic composition may include, within levels that will not harm the main effect, other ingredients that can desirably increase the main effect. In one embodiment of the present invention, the cosmetic composition may additionally include moisturizer, emollient agents, surfactants, UV absorbers, preservatives, fungicides, antioxidants, pH adjusting agent, organic or inorganic pigments, aromatics, cooling agent or antiperspirant. The formulation ratio of the above-mentioned ingredients can be decided by those skilled in the art within levels that will not harm the purpose and the effects of the present invention, and the formulation ratio based on total weight of the cosmetic composition can be 0.01 to 5% by weight, specifically 0.01 to 3% by weight.

In one embodiment of the present invention, a food composition for inflammation prevention or suppression is provided. The food composition may contain with an active ingredient that is a peptide comprising of an amino acid sequence from SEQ ID NO: 1 to SEQ ID NO: 161, a peptide comprising of amino acid sequence above 80% homology with above-mentioned sequences, or peptide fragment of above-mentioned peptides.

In one embodiment of the present invention, food composition is not limited to forms, but for example may be granules, powder, liquid, and solid forms. Each form can be formed with ingredients commonly used in the industry appropriately chosen by those skilled in the art, in addition to the active ingredient, and can increase the effect with other ingredients.

Decision for dosage on the above-mentioned active ingredient is within the level of those skilled in the art, and daily dosage for example may be 1 µg/kg/day to 10 mg/kg/day, more specifically 10 µg/kg/day to 1 mg/kg/day, more specifically 50 µg/kg/day to 100 µg/kg/day, but not limited to these numbers and can vary according to age, health status, complications and other various factors.

In one embodiment of the present invention, a use of prevention or treatment of inflammatory disease with a peptide comprising of an amino acid sequence from SEQ ID NO: 1 to SEQ ID NO: 161, a peptide comprising of amino acid sequence above 80% homology with above-mentioned sequences, or peptide fragment of above-mentioned peptides, is provided.

In one embodiment of the present invention, the method of prevention or treatment of inflammatory disease with applying peptides mentioned above in patients is provided.

In one embodiment of the present invention, a kit for prophylaxis or treatment of inflammatory diseases is provided. The kit may contain: a peptide with anti-inflammatory activity or a composition comprising of the peptide, wherein the peptide comprises any one amino acid sequence of SEQ ID NO: 1 to SEQ ID NO: 161, the peptide has above 80% homology with above-mentioned sequences, or the peptide is a fragment of the above-mentioned peptides; and instructions including at least one of administration dose, administration route, administration frequency, and indication of the peptide or composition.

The terms used herein is intended to be used to describe the embodiments, not to limit the present invention. Terms without numbers in front are not to limit the quantity but to show that there may be more than one thing of the term used. The term "including", "having", "consisting", and "comprising" shall be interpreted openly (i.e. "Including but not limited to").

Mention of range of numbers is used instead of stating separate numbers within the range, so unless it is explicitly stated, each number can be read as separate numbers integrated herein. The end values of all ranges are Included in the range and can be combined independently.

Unless otherwise noted or clearly contradicting in context, all methods mentioned herein can be performed in the proper order. The use of any one embodiment and all embodiment, or exemplary language (e.g., that use "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meaning normally understood by a person skilled in the art that the present invention belongs to.

The preferred embodiments of the present invention are the best mode known to the inventors to perform the present invention. It may become clear to those skilled in the art after reading the statements ahead of the variations in the preferred embodiments. The present inventors hope that those skilled in the art can use the variations adequately and present invention be conducted in other ways than listed herein. Thus, the present invention, as allowed by the patent law, includes equivalents, and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Tumor necrosis factor (TNF), particularly TNF-α, is known to be released from inflammatory cells and cause various cytotoxic reactions, immunological reactions and inflammatory reactions. TNF-α is known to be involved in the occurrence and prolongation of many inflammatory and autoimmune diseases and further cause serious septicemia and septic shock when it is released into the blood and acts systemically. Because TNF-α is a factor associated widely with the immune system of a living body, the development of agents inhibiting TNF-α is actively carried out. TNF-α is biosynthesized in an inactive form and becomes an active form by being cleaved by protease; the enzyme responsible for the activation is called a tumor necrosis factor-converting enzyme (TACE). Thus, a substance inhibiting this TACE can treat, improve, or prevent diseases, pathologic conditions, abnormal conditions, troubles, adverse symptoms and the like ascribed to TNF-α.

High-mobility group box 1 (HMGB1) protein exists in high concentrations in thymus, lymph nodes, testes, and in fetal liver, and with exception to liver and brain cells, usually exists inside of the nucleus. The said HMGB1 protein has 3 domains consisting of A-box, B-box, and C-terminal.

It was reported by Tracey et al., 1999 that HMGB1 protein has a role as a cytokine which induces inflammation, and the mechanism of said HMGB1's inflammation induction is by an external stimulus causing acetylation of HMGB1 which then moves from the nucleus into the cytoplasm. Afterward, it is known to be secreted out of the cell, or secreted out from the cell in necrosis. (Bonaldi T et al., EMBO J, (22)5551-60, 2003).

The invention is further described by the figures, the following examples and experiments, which are solely for the purpose of illustrating specific embodiments of this invention, and are not to be construed as limiting the scope of the invention in any way.

EXAMPLE 1

Synthesis of PEP-1 and Measurement of Anti-Inflammatory Activities of PEP-1 (SEQ ID NO: 1)

Experiment 1. Synthesis of PEP-1 (SEQ ID NO: 1)

A peptide comprised of 16 amino acids with the chemical structure 1 as below having the sequence SEQ ID: 1 (PEP-1) derived from human telomerase was synthesized:

<Chemical Structure 1>

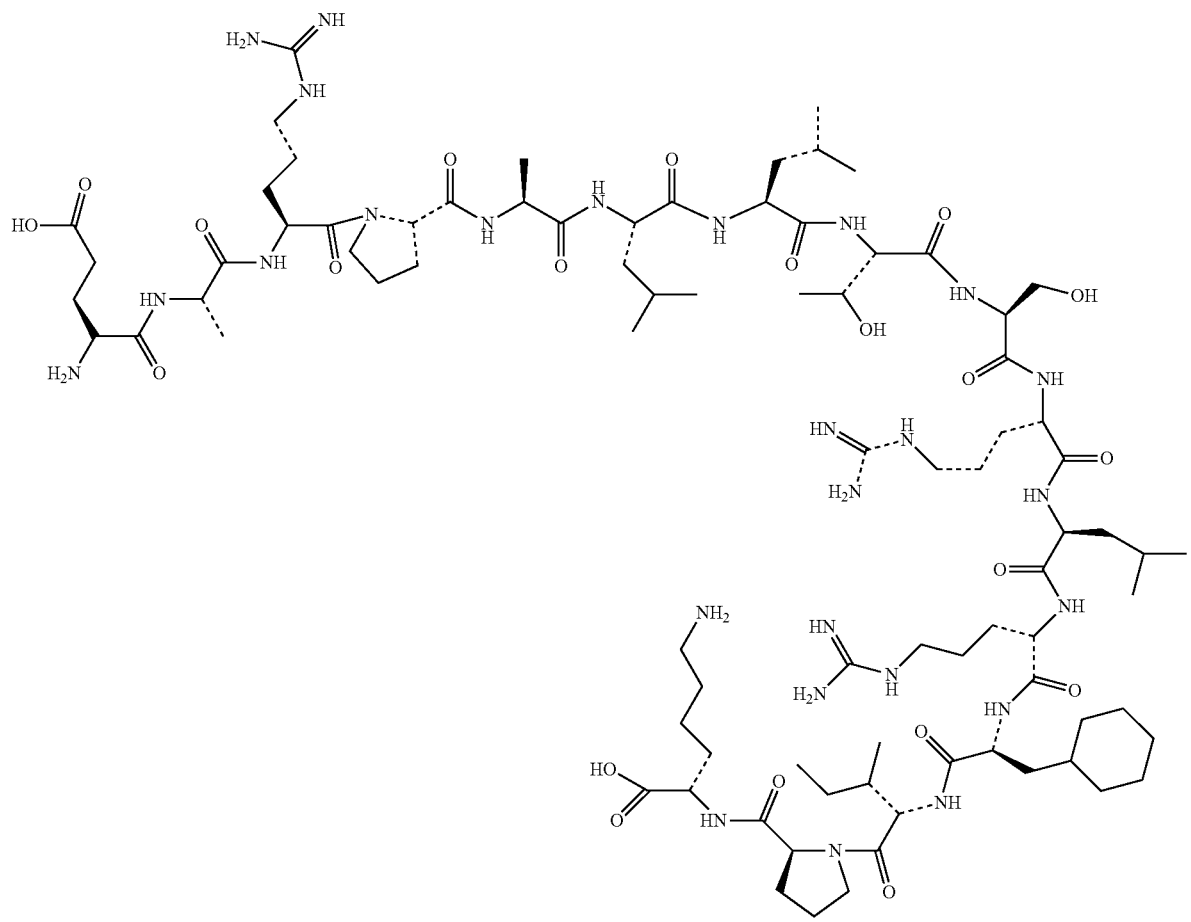

SEQ ID NO: 1 (PEP-1) was synthesized according to the existing method of solid phase peptide synthesis. In detail, the peptides were synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to resin were used as follows:

NH$_2$-Lys(Boc)-2-chloro-Trityl Resin
NH$_2$-Ala-2-chloro-Trityl Resin
NH$_2$-Arg(Pbf)-2-chloro-Trityl Resin All the amino acid materials to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in acid. Such as:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. In 20% of DMF, piperidine was used to remove Fmoc. In order to remove the protection from residue or to separate the synthesized peptide from Resin, cleavage cocktail [TFA (trifluoroacetic acid)/TIS (triisopropylsilane)/EDT (ethanedithiol)/H$_2$O=92.5/2.5/2.5/2.5] was used.

Synthesized the peptide by using the solid phase scaffold combined to starting amino acid with the amino acid protection, reacting the corresponding amino acids separately, washing with solvent and deprotected, and repeating the process. After cutting off the synthesized peptide from the resin, it was purified by HPLC and verify for synthesis by MS, and then freeze-dried.

Specific synthesis process of PEP 1 is described by the following.

1) Coupling

Melted the amino acid (8 equivalent) protected with NH$_2$-Lys(Boc)-2-chloro-Trityl Resin, and coupling agent HBTU (8 equiv.)/HOBt (8equiv.)/NMM (16 equiv.) and added to DMF, then let react in room temperature for 2 hours, then washed with DMF, MeOH, and DMF in that order.

2) Fmoc deprotection

Added 20% piperidine in DMF and reacted in room temperature for 5 minutes 2 times, then washed with DMF, MeOH, and DMF in that order.

3) Make the basic framework of peptide by repeating reactions 1 and 2 repeatedly.

4) Cleavage: Add Cleavage Cocktail to the completely synthesized peptide and separated the peptide from the resin.

5) Add cooling diethyl ether into obtained mixture, and then centrifugation is used to precipitate gathered peptide.

6) After purification by Prep-HPLC, check the molecular weight by LC/MS and lyophilize to produce in powder form.

Experiment 2: Anti-Inflammatory Activity Measurement of PEP 1

Cell Lines Culture

Raw 264.7macrophage cell (KCBL, 40071) from Korea Cell Bank was maintained in Dulbecco's modified Eagle's medium (DMEM; PAA, Austria) containing 10% fetal bovine serum (FBS; Gibco Laboratories), 100 unit/mL of streptomycin, and penicillin (Gibco Laboratories) at 37° C. with 5% $CO_2$. Raw 264.7 cells were seeded into a 96-well plate at a density of $1 \times 10^6$ cells/mL and incubated overnight. On the following day, the medium was replaced with fresh medium and 5 µg/mL of peptide (obtained as described in Experiment example 1) was added to the cells. After 30 min incubation of cells with the peptide 50 µL of LPS (to a final concentration of 1 µg/mL) was added, and cells were incubated for additional 24 hr. The experimental sample with the induction of inflammatory response was treated with 1 µg/mL mL lipopolysaccharide (LPS; Sigma, USA) and control sample was treated with phosphate buffered saline (PBS; pH 7.2). The supernatant samples from each condition was collected in eppendorf tubes and subjected to further analysis.

Experiment 2-1. NO Level Analysis

The level of nitric oxide (NO) was measured in Raw 264.7 cell ($1 \times 10^6$ cell/ml) using Griess reagent system (Promega, USA). Culture medium of 50 µl was added to a 96-well plate and Griess reagent I (NED) solution and Griess reagent II (Sulfaniliamide solution) are added in the same amount. After 10 min incubation of cells with the reagents, the optical density at 540 nm was measured within 30 min using a microplate reader (Molecular Devices, USA). The concentration of NO was calculated by using a standard curve (0~100 µM) of sodium nitrite.

As shown in Table 3 below, stimulation of cells with LPS increased the expression of NO, but in co-treatment with LPS and Pep1, the expression level of NO mentioned above decreased. NO is produced during inflammation, and the result showing Pep1 reduced NO level to 65% of the control strongly support the anti-inflammatory effect of Pep1.

TABLE 3

The measurement of anti-inflammatory effect of human telomerase derived PEP 1

| Test sample | | NO Expression Level of control (%) | Decreased NO Expression Level (%) |
|---|---|---|---|
| PBS | | 0 | — |
| LPS 1 µg/mL | PBS | 100 | 0 |
| | PEP 1 (0.5 µg/mL) | 35 | 65 |

Experiment 2-2. Analysis of Cytokine Inhibitory Effect

To investigate the effect of PEP1 on inhibiting pro-inflammatory cytokine production RAW 264.7 cell were pre-treated with PEP 1 at a concentration of 5 µg/mL challenged with LPS at a concentration of 1 µg/mL, and cells were further incubated for 24 hr. The supernatant samples containing cell culture medium was collected and analyzed for the cytokine levels using ELISA kits (eBioscience, San Diego).

96 wells plates were coated with 100 µl of capture antibodies (diluted in coating buffer to the concentration recommended by manufacturer's protocol) overnight at 4° C. Then, after washing the plates 5 times, 200 µL of assay diluents was added to each well and incubated for 1 hr at room temperature for blocking. After washing each well with wash buffer five times, cell culture sample or each cytokine standard protein sample was diluted and 100 µl of each added into each well. The plate containing samples were incubated overnight at 4° C. Then, after washing the plate five times with the wash buffer, 100 µl of secondary antibody conjugated to avidin was added and incubated for 1 hr at room temperature.

Following incubation with the secondary antibody, the plate was washed five times and incubated with 100 µl of avidin-HRP (BD Bioscience) for 30 min at room temperature. After washing the plate seven times, 100 µl of TMB solution (Pierce) was added and incubated for 15 min at room temperature. The reaction was stopped by adding 50 µl of 2N $H_2SO_4$ in each well The optical density at 450 nm was measured using a microplate reader. Statistical analysis was performed by variance analysis using ANOVA procedure of SPSS program, and verified the significance between analyses using Duncan's multiple range test.

Experiment 2-3. IL-6 Secretion Measurement

As shown in Table 4 below, treatment with LPS alone increased the cytokine IL-6 (interleukin-6) secretion. However, co-treatment with LPS and PEP-1 showed a decrease in the level of the pro-inflammatory cytokine IL-6 secretion. More importantly, after the treatment with PEP-1, the level of pro-inflammatory cytokine secretion decreased by more than 70%, which indicates a robust anti-inflammatory effect of Pep1.

TABLE 4

Cytokine IL-6 production inhibition by PEP-1

| Test sample | | cytokine IL-6 production | |
|---|---|---|---|
| | | % of control | inhibition % |
| PBS | | 0 | — |
| LPS 1 µg/ml | PBS | 100 | 0 |
| | PEP 1 (5 µg/ml) | 28 | 72 |

Experiment 2-4, HMGB1, TNF-α, COX-2 Expression Inhibition

Protein expression level was determined by Western blot analysis. Cells grown in PEP-1 containing medium were washed with PBS, treated with 0.05% trypsin-EDTA, and collected by centrifugation. The collected cells were dissolved in an appropriate volume of lysis buffer. Intracellular debris was pelleted by centrifugation, and equal amount of protein from each sample was separated by SDS-polyacrylamide gel electrophoresis. The separated protein was transferred to nitrocellulose membrane (Schleicherand Schuell, Keene, NH, USA), then was tested for the antibody specific for each protein. The membrane was incubated with ECL (enhanced chemiluminoesence) solution(Amersham Life Science Corp., Arlington Heights, IL, USA), exposed to X-ray, and the level of protein expression was analyzed according to the exposure level shown on the X-ray film.

Western blot analysis was performed to determine the inhibitory effect of Ppep1 on the cytokine protein expression. As shown in Table 5 below, stimulation of cells with LPS increased the expression of cytokines; HMGB1, TNF-α and COX. However, if cells were treated with both LPS and Pep1, the expression level of pro-inflammatory cytokines mentioned above decreased. The result showing the treatment with Pep1 decreased pro-inflammatory cytokine levels by more than 70% provide strong evidence supporting the anti-inflammatory effect of Pep1.

TABLE 5

The measurement of inhibitory effect of Pep1 on pro-inflammatory cytokine expression level.

| Test sample | | Cytokine Expression Level (band intensity) % of control | | |
|---|---|---|---|---|
| | | HMGB1 | TNF-α | COX-2 |
| PBS | | — | — | — |
| LPS 1 µg/ml | PBS | 100 | 100 | 100 |
| | PEP 1 (5 µg/ml) | 30 | 25 | 22 |

EXAMPLE 2

TNF-α Inhibitory Effect of PEP RIA Series (Sequence No. 1 to 161) Peptides

Based on the results from Example 1 in which the SEQ ID NO: 1 (PEP1) has the TNF-α inhibitory effect, experiment using peptides SEQ ID NO: 1 to 161 were carried out to confirm their TNF-α inhibitory effect. The synthesis of peptides SEQ ID NO: 1 to 161 used the same method mentioned above in Example 1 (method used for synthesis of PEP1), but the amino acids added were different.

Experiment 1: Cell Culture

PBMC (peripheral blood mononuclear cells) layer was separated from blood samples (50 ml) collected in healthy subjects using Biocoll Separating Solution (Biochrom AG, Berlin, Germany). The collected PBMC were enriched in RPMI 1640 medium containing 20% human serum for 30 mins, and then transferred to 100-mm polystyrene cell culture plate coated with human serum for incubation for 2 hrs at 37° C., 5% $CO^2$ incubator. Monocytes were detached from the bottom of the plate using cold PBS, and incubated to reach the number of $1\times10^5$ cell/well in 96-well plate with RPMI 1640 medium (supplemented with penicillin-streptomycin; 100 mg/ml, human serum; 20%) over night.

Experiment 2: Analysis of TNF-α Inhibitory Effect in PBMC-Derived Monocyte

ELISA was performed to find out how the peptides of the PEP RIA series influence TNF-α level. PBMC-derived monocytes were incubated to reach the number of $1\times10^5$ cells per well in a 96-well plate and then treated with LPS (lipopolysaccharide; 10 ng/ml, Sigma) for 2 hours. To the monocytes that were washed three times with PBS, OPTI-MEM culture medium was added to induce cell starvation for an hour, 4 µM of the peptide was taken out and incubated for 2 hours. There were three negative control groups. The first group was not treated with anything. The second group that was treated with estrogen (in this experiment, estradiol was used as a kind of estrogen). The third group was treated with LPS (10 ng/ml) or with LPS (10 ng/ml) as well as estrogen (20 nM). PEP1 that was confirmed to have TNF-α inhibiting activity was used as a positive control to measure TNF-α inhibiting activity. After incubation, TNF-α was measured by following the ELISA kit manual (R&D, Minneapolis, MN, USA). The details of quantification method can be found in Experiment 2.2 of Example 1.

Using the method stated above, Peptides with TNF-α inhibiting effect were screened. PBMC-derived monocytes were stimulated with LPS (10 ng/ml), which is endotoxin, for 2 hours and were induced to starve by adding OPTI-MEM for 1 hour. After that, 4 µM of 161 peptides were treated and incubated for 2 hrs. The amount of TNF-α in the cell culture medium was measured using ELISA, and the peptides with TNF-α inhibiting effect were screened by comparing to the negative and positive controls (FIG. 1 to FIG. 16).

The followings are the peptides that showed TNF-α inhibiting effect when compared to the control group that was treated with only LPS: SEQ ID NO: 1 to SEQ ID NO: 6, SEQ ID NO: 9, SEQ ID NO: 11, SEQ ID NO: 14 to 21, SEQ ID NO: 23 to SEQ ID NO: 37, SEQ ID NO: 39 to SEQ ID NO: 44, SEQ ID NO: 47 to SEQ ID NO: 53, SEQ ID NO: 55 to SEQ ID NO: 61, SEQ ID NO: 63 to SEQ ID NO: 82, SEQ ID NO: 84 to SEQ ID NO: 94, SEQ ID NO: 96, SEQ ID NO: 99 to SEQ ID NO: 104, SEQ ID NO: 107 to SEQ ID NO: 109, SEQ ID NO: 115, SEQ ID NO: 116, SEQ ID NO: 120 to SEQ ID NO: 122, SEQ ID NO: 124, SEQ ID NO: 129 to SEQ ID NO: 133, SEQ ID NO: 142 to SEQ ID NO: 144, SEQ ID NO: 146, SEQ ID NO: 148, SEQ ID NO: 149, and SEQ ID NO: 155 to SEQ ID NO: 159.

Also, the followings are the peptides that showed TNF-α inhibiting effect when compared to the group treated with LPS and estrogen: SEQ ID NO: 15 to SEQ ID NO: 18, SEQ ID NO: 23 to SEQ ID NO: 27, SEQ ID NO: 29, SEQ ID NO: 31 to SEQ ID NO: 34, SEQ ID NO: 39 to SEQ ID NO: 41, SEQ ID NO: 47, SEQ ID NO:48, SEQ ID NO: 51 to SEQ ID NO: 53, SEQ ID NO: 55 to SEQ ID NO: 58, SEQ ID NO: 61, SEQ ID NO: 65 to SEQ ID NO: 68, SEQ ID NO: 70, SEQ ID NO: 73 to SEQ ID NO: 79, SEQ ID NO: 81, SEQ ID NO: 82, SEQ ID NO: 84 to SEQ ID NO: 87, SEQ ID NO: 8=90 to SEQ ID NO: 94, SEQ ID NO: 96, SEQ ID NO: 99, SEQ ID NO: 101 to SEQ ID NO: 104, SEQ ID NO: 107 to SEQ ID NO: 109, SEQ ID NO: 120, SEQ ID NO: 121, SEQ ID NO: 129 to SEQ ID NO: 132, SEQ ID NO: 142 to SEQ ID NO: 144, SEQ ID NO: 146, SEQ ID NO: 148, SEQ ID NO: 149, and SEQ ID NO: 157 to SEQ ID NO: 159.

Experiment 3: Analysis of Peptides Affecting TNF-α Level in THP1 Cell Line

Experiment was carried out using THP-1 cell line (American Type Culture Collection (ATCC), Manassas, VA, USA) which is human acute monocytic leukemia.

THP-1 cells were incubated to reach the number of $1\times10^5$ cells per well in a 96-well plate with RPMI 1640 medium for 24 hrs, followed by addition of 100 µM of PMA (phorbol 12-myristate 13-acetate) for the differentiation into macrophage. After differentiation of THP-1 into macrophage by PMA for a day, LPS was treated for 2 hrs and washed off. Starvation for an hour and PEP1 treatment followed.

THP-1 cell differentiated by PMA was treated with LPS (lipopolysaccharide; 10 ng/ml, Sigma) for 2 hours, followed by 2 times washes with PBS. To the cells, OPTI-MEM culture medium was added to induce cell starvation for an hour, and 1 μM of 161 peptides was taken out and incubated for an hour. After incubation, TNF-α level was measured by using the ELISA kit and the peptides which reduce the TNF-α level were screened (FIG. 17 to FIG. 35).

As a result, peptide SEQ ID NO: 1 to SEQ ID NO: 5, SEQ ID NO: 7, SEQ ID NO: 9, SEQ ID NO: 10, SEQ ID NO: 12, SEQ ID NO: 13, SEQ ID NO: 15, SEQ ID NO: 17 to SEQ ID NO: 27, SEQ ID NO: 29, SEQ ID NO: 30, SEQ ID NO: 32 to SEQ ID NO: 53, SEQ ID NO: 55 to SEQ ID NO: 60, SEQ ID NO: 67, SEQ ID NO: 68, SEQ ID NO: 70, SEQ ID NO: 72 to SEQ ID NO: 82, SEQ ID NO: 84 to SEQ ID NO: 92, SEQ ID NO: 94, SEQ ID NO: 99 to SEQ ID NO: 112, SEQ ID NO: 114, SEQ ID NO: 127 to SEQ ID NO: 144, SEQ ID NO: 146, SEQ ID NO: 148, SEQ ID NO: 149, SEQ ID NO: 151 and SEQ ID NO: 153 to SEQ ID NO: 161 appeared to reduce the TNF-α level compared to control group treated only with LPS.

In addition, SEQ ID NO: 1 to SEQ ID NO: 5, SEQ ID NO: 7, SEQ ID NO: 9, SEQ ID NO: 10, SEQ ID NO: 12, SEQ ID NO: 13, SEQ ID NO: 15, SEQ ID NO: 17 to SEQ ID NO: 23, SEQ ID NO: 25 to SEQ ID NO: 27, SEQ ID NO: 29, SEQ ID NO: 30, SEQ ID NO: 33 to SEQ ID NO: 43, SEQ ID NO: 156, SEQ ID NO: 157 and SEQ ID NO: 159 were selected as peptides which reduce the expression level of TNF-α compared to that of group treated with LPS and estrogen.

EXAMPLE 3

Effects of Peptides (SEQ ID No:1 to 161) on Inflammation by Amyloid-β Protein

HMGB1 first undergoes acetylation and translocation to cytoplasm by external stimulation. Then it is secreted out of the cell, therefore serving the role of Inflammation-causing cytokine. Because when one has an inflammation due to such activity, HMGB1 protein is secreted from the cell, and patients with inflammatory diseases such as Churg strauss syndrome, rheumatoid arthritis and Sjogren's syndrome will present with elevated serum levels of HMGB1. Hence, if nucleus contains large amount of HMGB1 even when there is a stimulus that causes inflammation, it is suggestive of the fact that HMGB1 is not being secreted out of the cell, which means inflammation is being suppressed.

Experiment 1. Cell Culture

Undifferentiated PC12 cells (ATCC, Rockville, MD, USA) were maintained in ogarithmic-phase growth on poly-1-lysine (Sigma, Saint Louis, MO, USA)—precoated 100 mm dishes (Corning, PA, USA) in RPMI 1640 medium (GIBCO, Grand Island, NY, USA) containing 10% heat-inactivated horse serum, 5% heat-inactivated fetal bovine serum, 100 units/ml penicillin, and 100 g/ml streptomycin. Cultures were incubated at 37° C. in a humidified atmosphere with 5% $CO^2$. The cultures were grown to 50% confluence and were harvested in $Ca^{2+}/Mg^{2+}$-free Hank's balanced salt solution containing 1 mM EDTA. Cells were plated at a density of $1\times10^6$ cells/100 mm dish and incubated for 24 hrs. For neuronal differentiation, PC12 cells were serum-starved for 12 hrs (RPMI1640 medium containing 100 units/ml penicillin and 100 g/ml streptomycin without horse serum or fetal bovine serum); thereafter, the cells were maintained in serum-free medium. After two days the medium was replaced with fresh serum-free medium. On day three, NGF (50 ng/ml, Sigma, Saint Louis, MO, USA) was added to the medium, and the cultures were maintained for an additional three days. After differentiation, nPC12 cells were incubated with 20 μM amyloid-β with several concentrations of the peptides [0 (control), 1, 10, and 50 μM] for 48 hrs.

Experiment 2. Western Blot Analysis

Levels of HMGB1 were analyzed by western blotting. Briefly, $5\times10^6$ cells were washed twice in cold PBS, incubated for 10 min on ice in lysis buffer [50 mM Tris (pH 8.0), 150 mM NaCl, 0.02% sodium azide, 0.2% SDS, 100 μg/ml phenyl methyl sulfonyl fluoride (PMSF), 50 μl/ml aprotinin, 1% Igepal 630, 100 mM NaF, 0.5% sodium deoxy choate, 0.5 mM EDTA, 0.1 mM EGTA]; unbroken cells and nuclei were pelleted by centrifugation for 10 min at 2000×g and the lysates were cleared by centrifugation at 10,000×g. The antibodies used were: anti-HMGB1 (1:1000, Cell Signaling, Beverly, MA, USA) and anti-β-tubulin (1:1000, Cell Signaling, Beverly, MA, USA). The membranes were washed with Tris-buffered saline containing 0.05% Tween-20 (TBST), and then processed using HRP-conjugated anti-rabbit antibody (Amersham Pharmacia Biotech, Piscataway, NJ, USA) followed by ECL detection (Amersham Pharmacia Biotech,). The blots were quantified with an image analyzer (GE Healthcare, ImageQuant LAS 4000).

Figure 36:
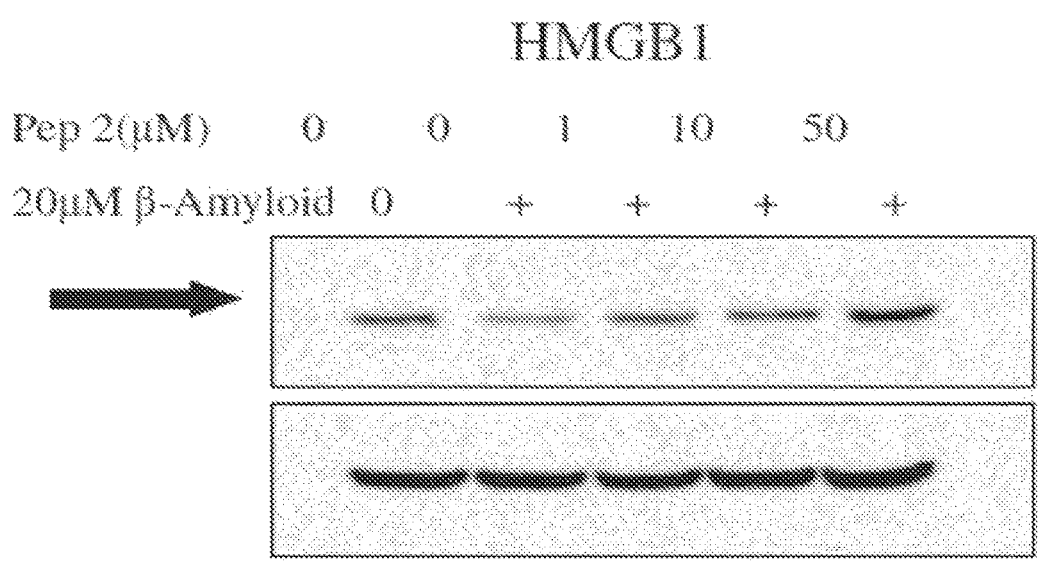
FIG. 36 to FIG. 108 are the western blot results of selected peptides which showed accumulation of HMGB1 in the cell.
Figure 37:
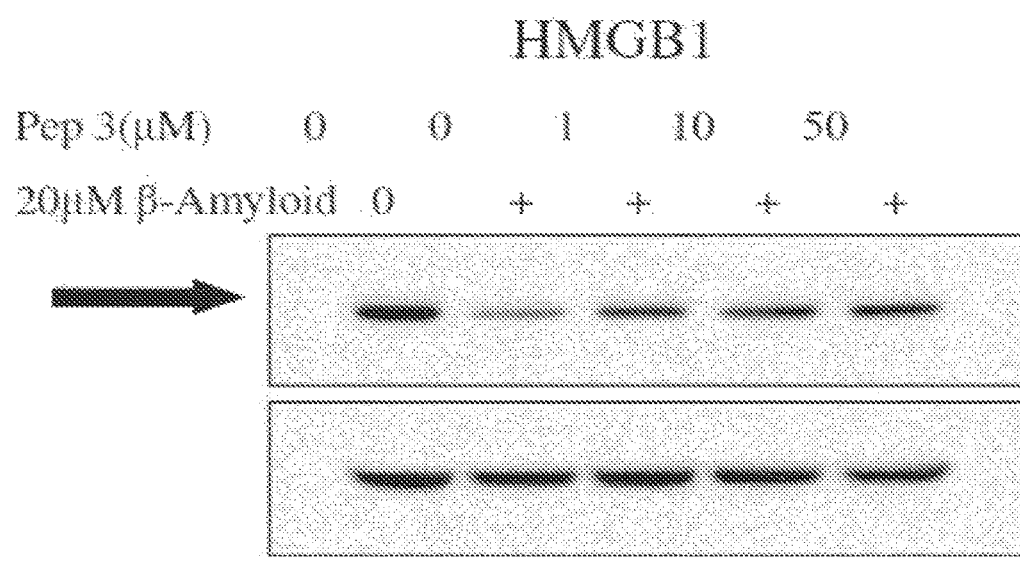
Figure 38:
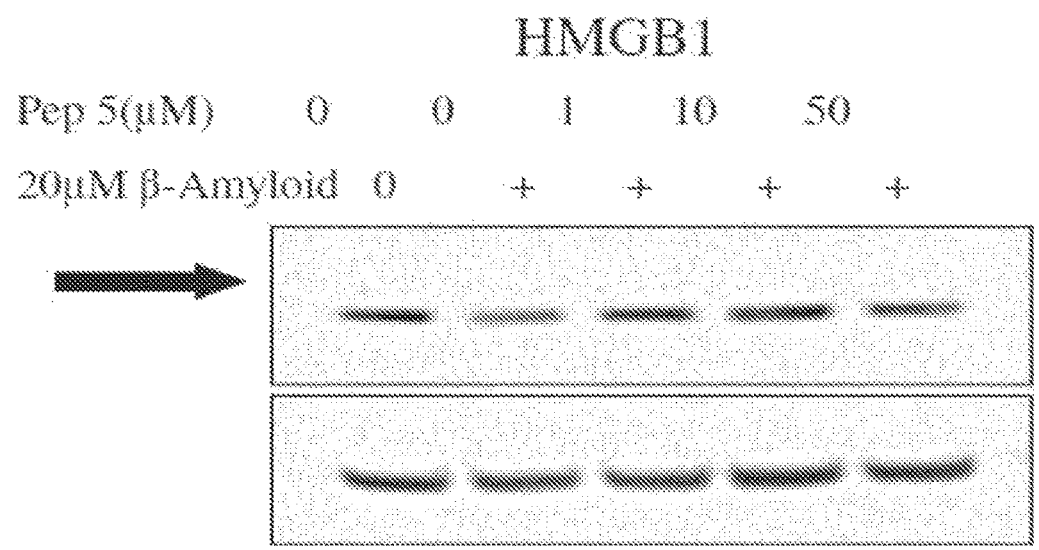
Figure 39:
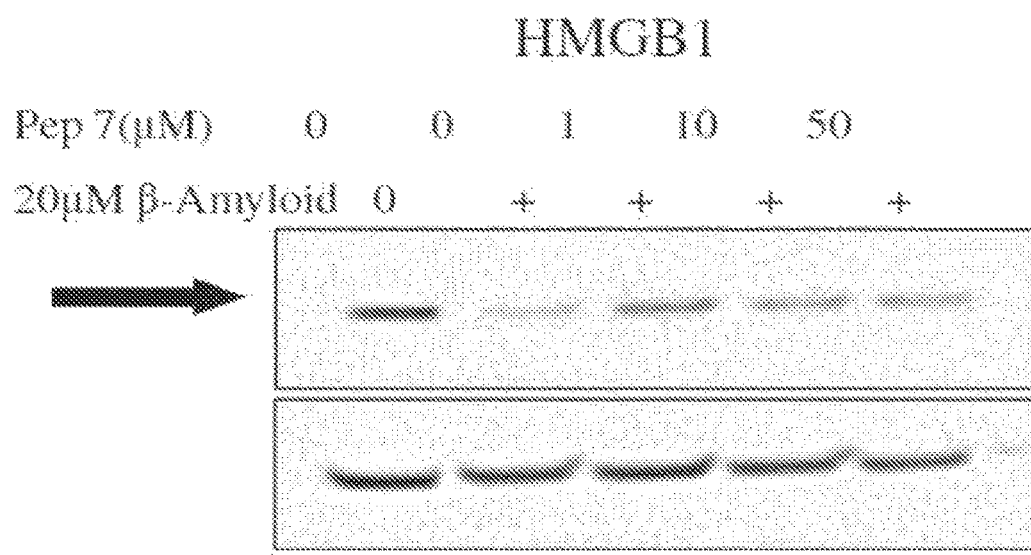
Figure 40:
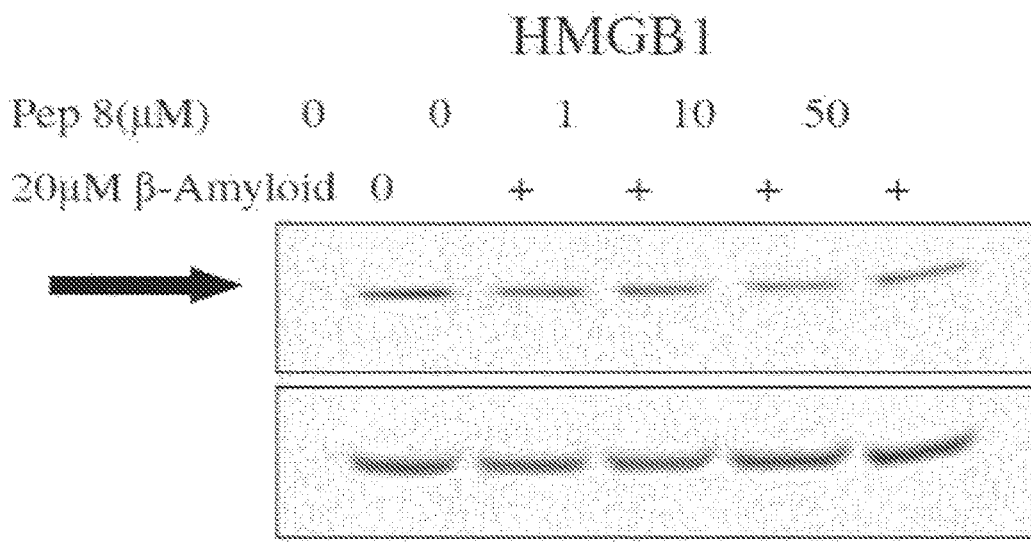
Figure 41:
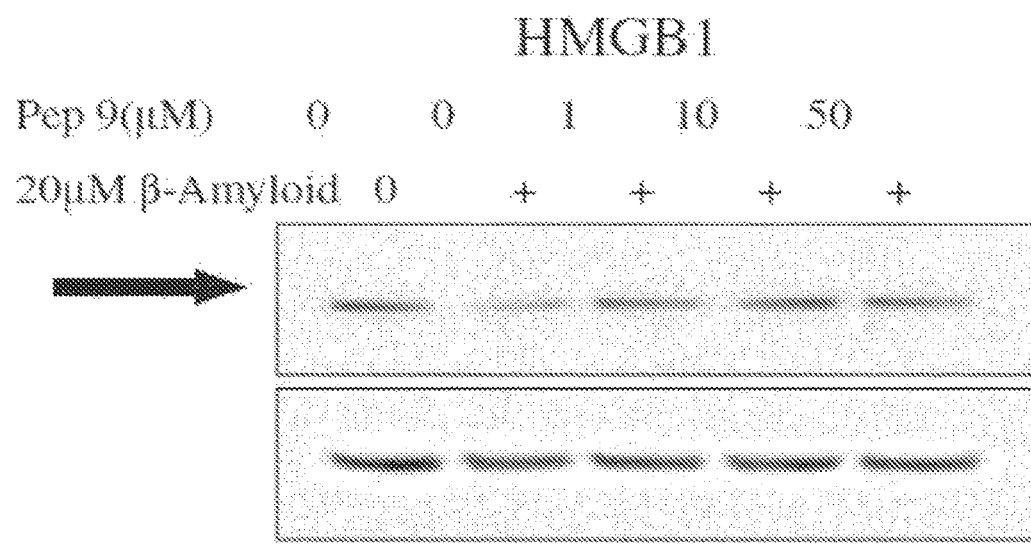
Figure 42:
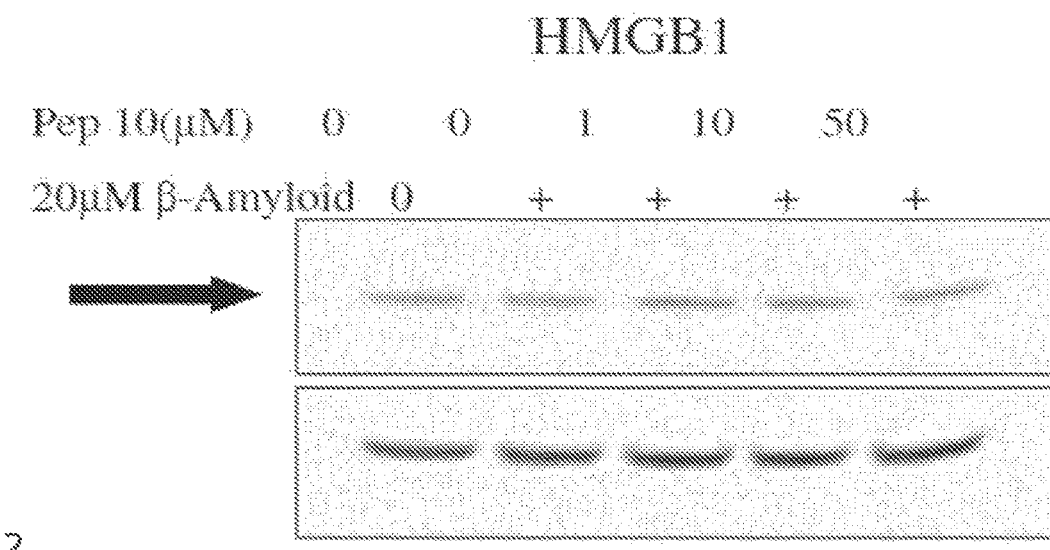
Figure 43:
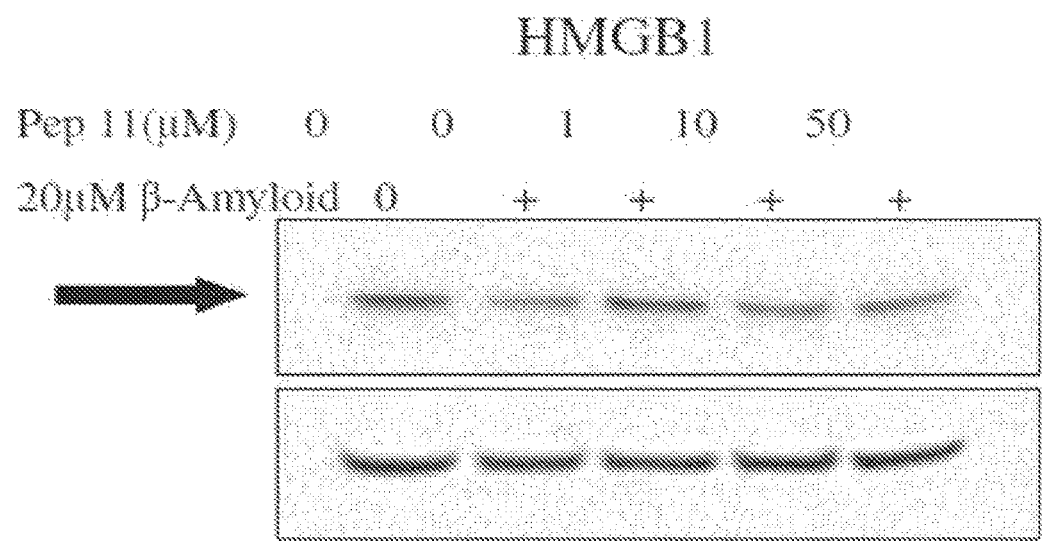
Figure 44:
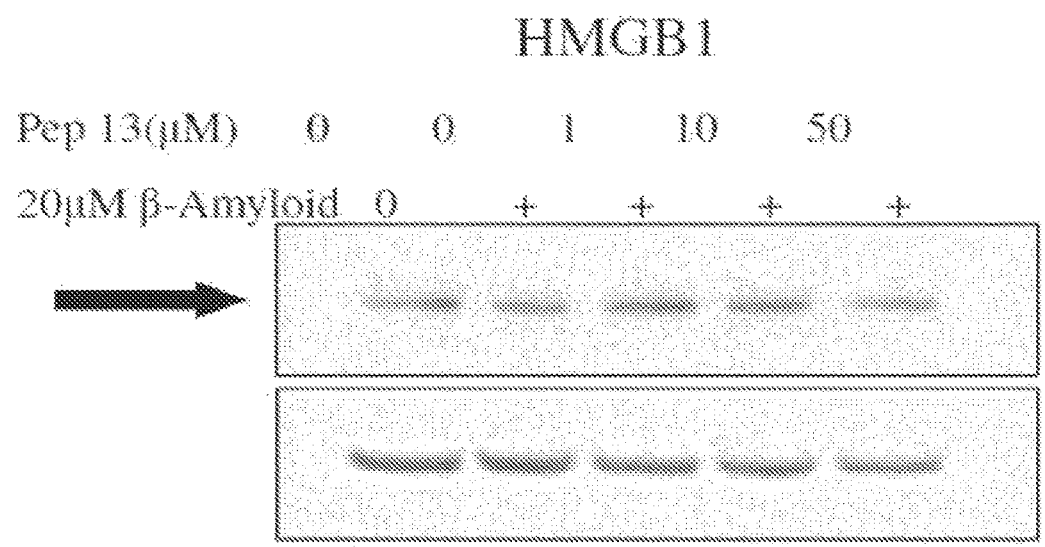
Figure 45:
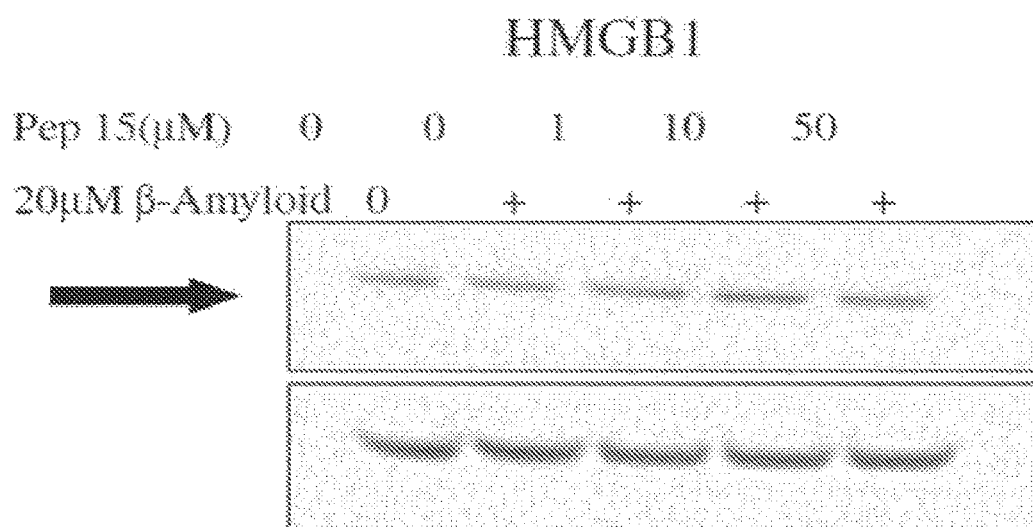
Figure 46:
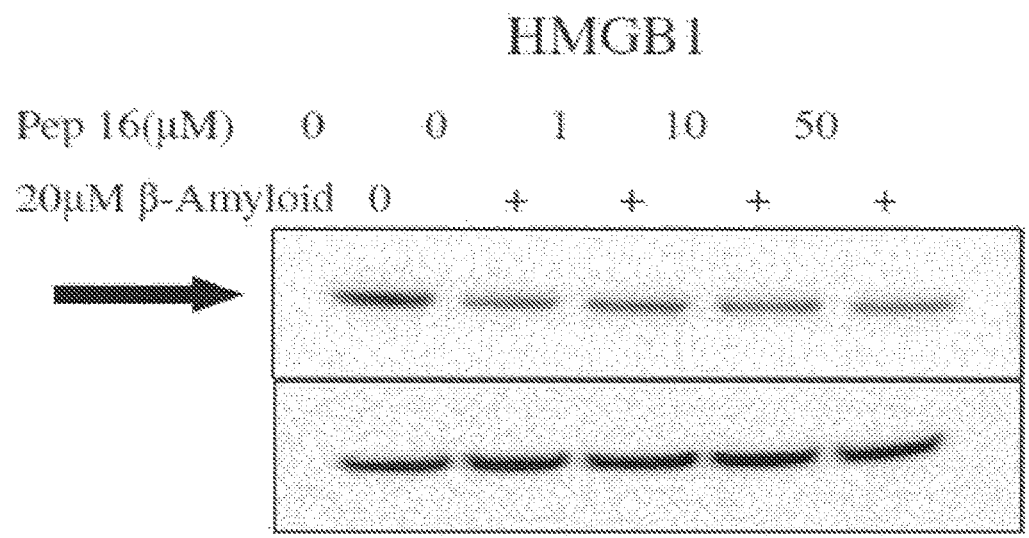
Figure 47:
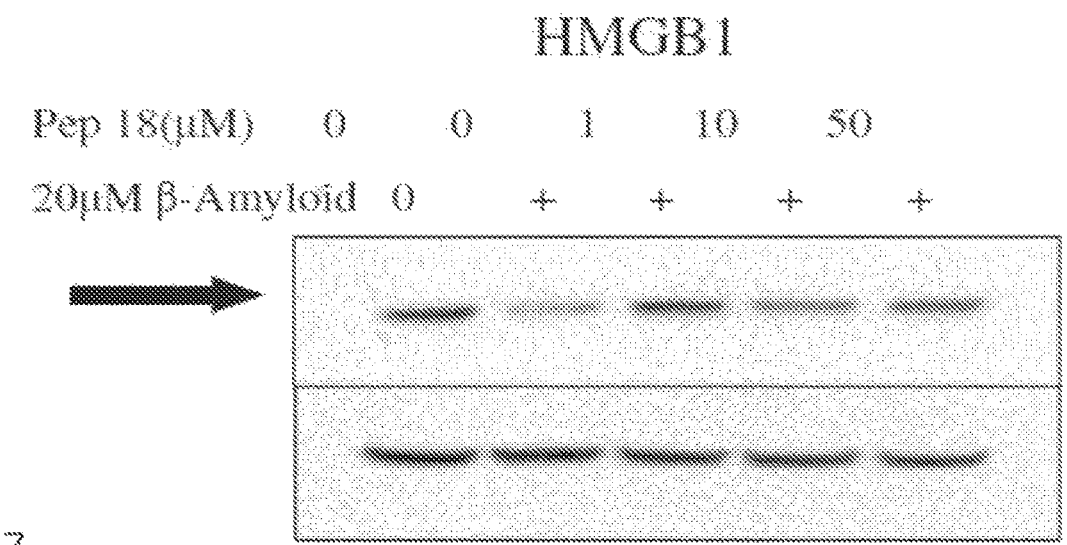
Figure 48:
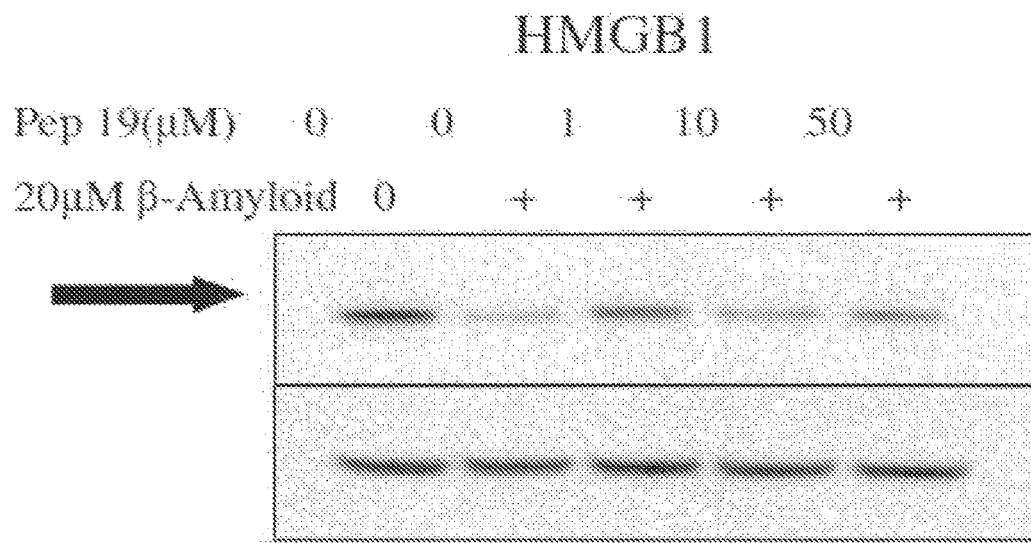
Figure 49:
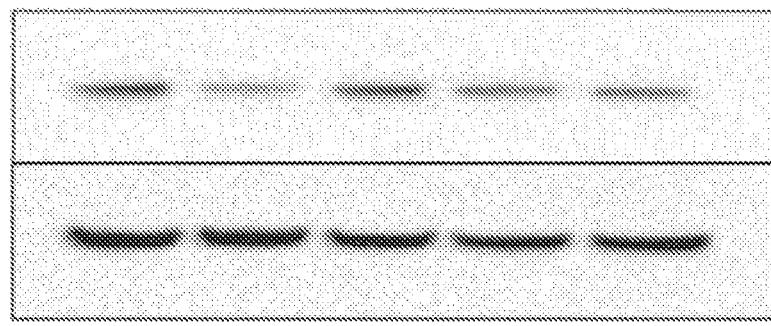
Figure 50:
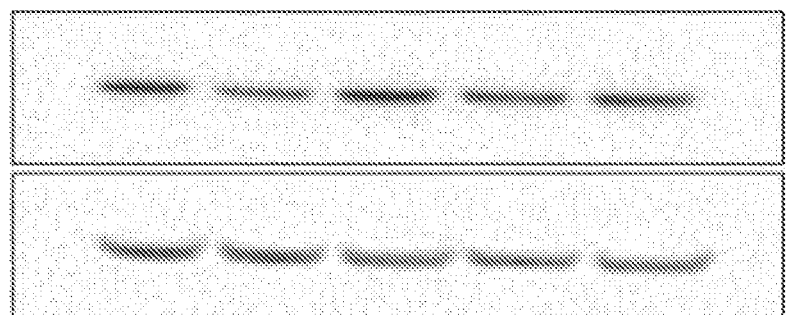
Figure 51:
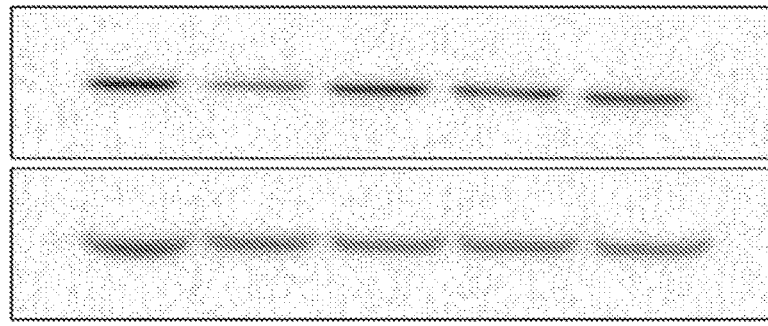
Figure 52:
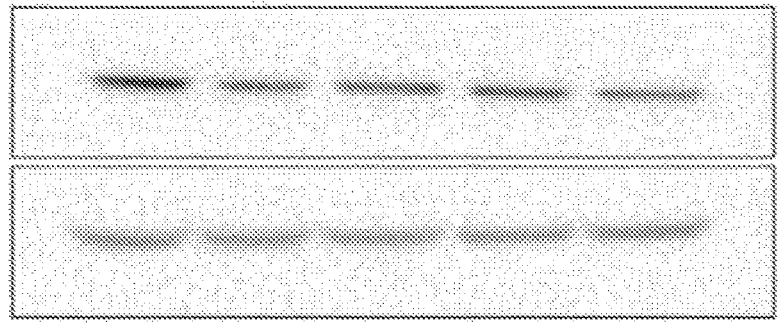
Figure 53:
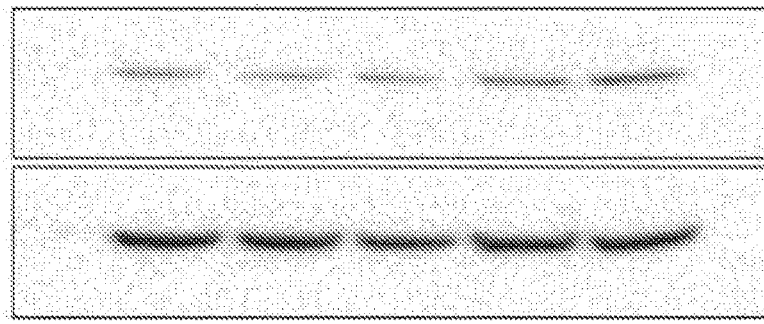
Figure 54:
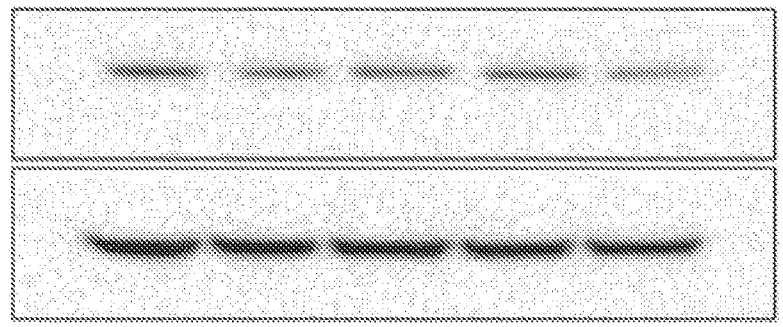
Figure 55:
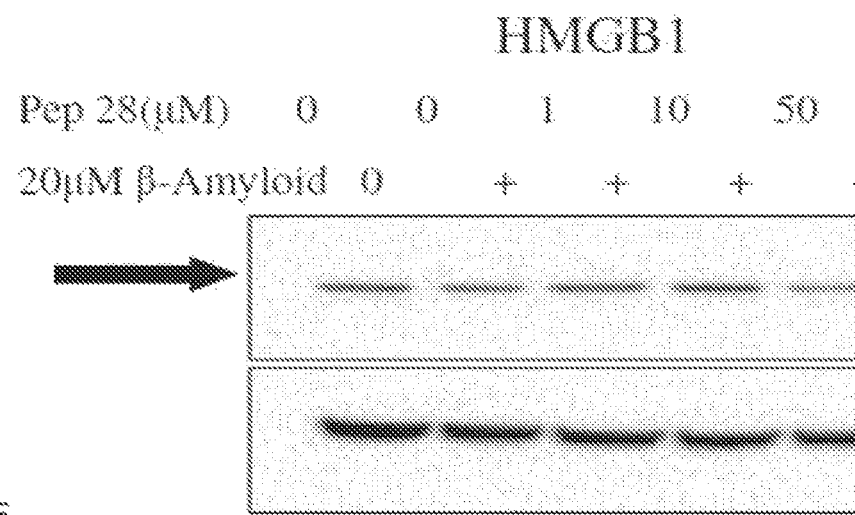
Figure 56:
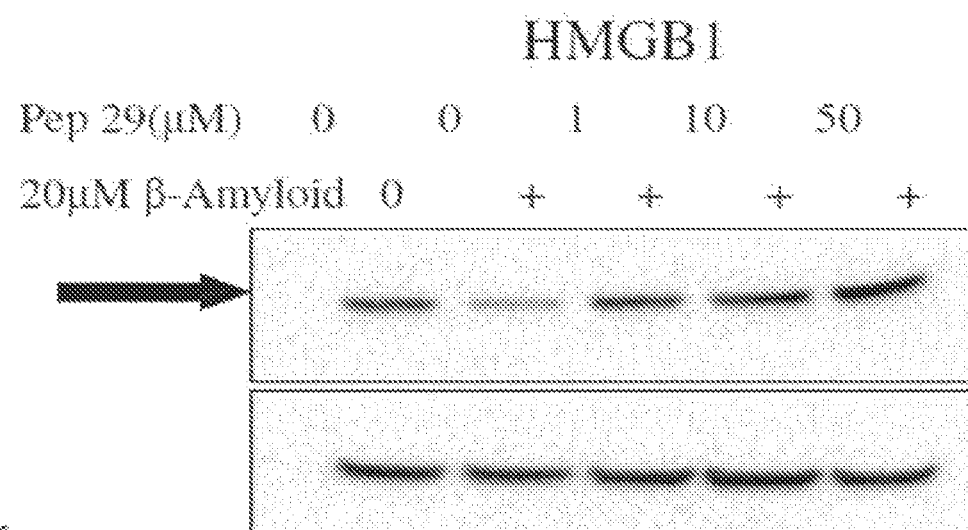
Figure 57:
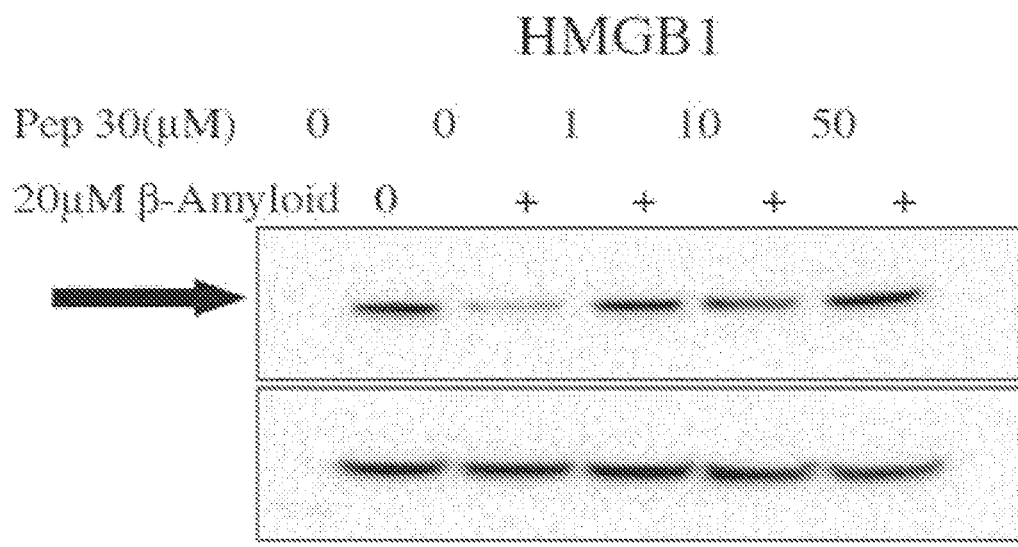
Figure 58:
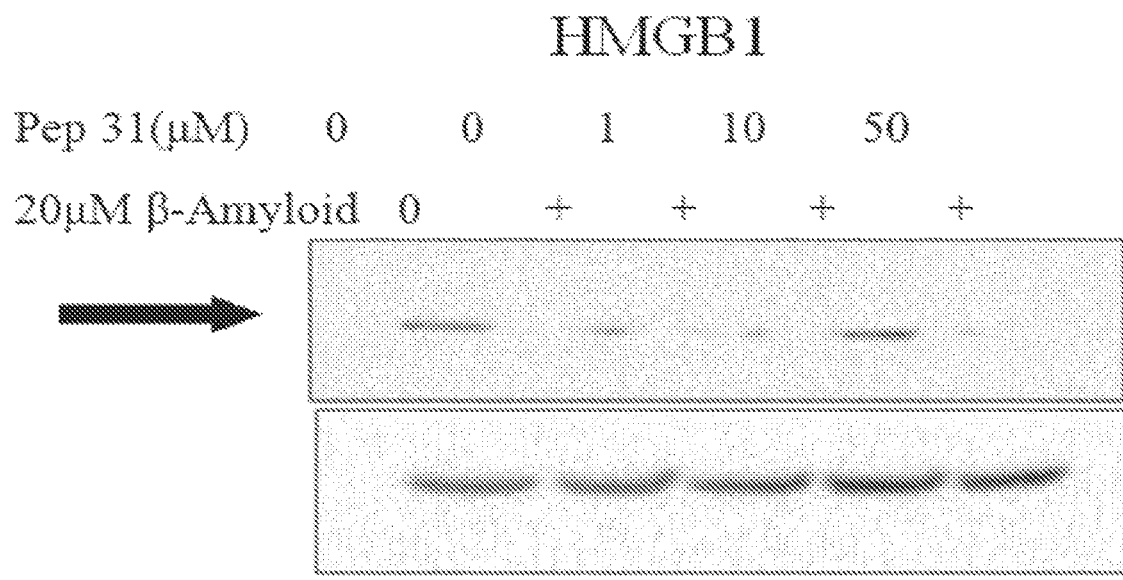
Figure 59:
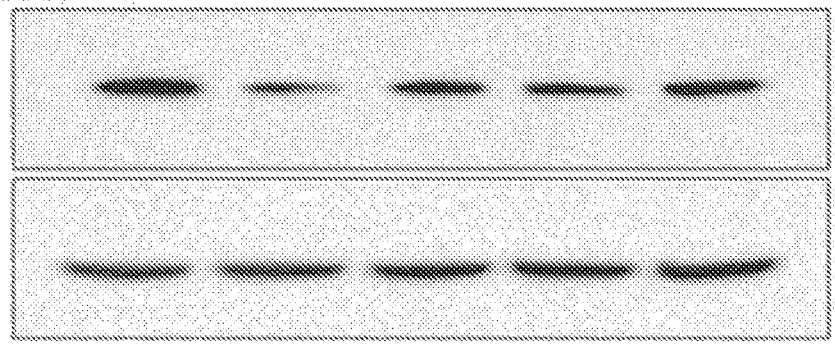
Figure 60:
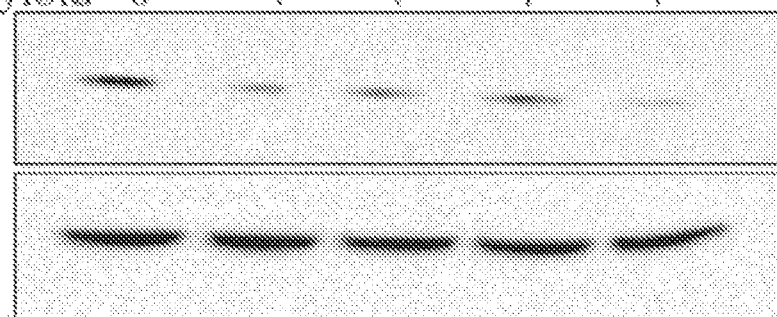
Figure 61:
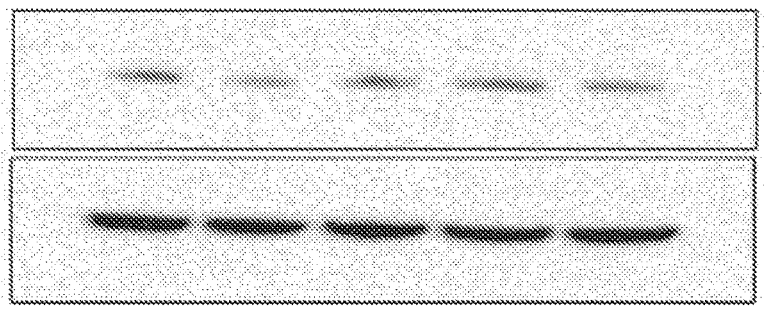
Figure 62:
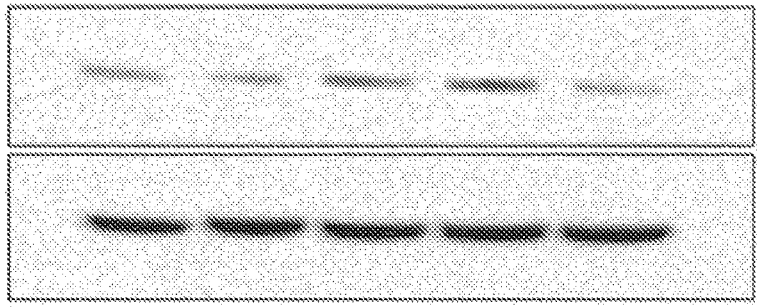
Figure 63:
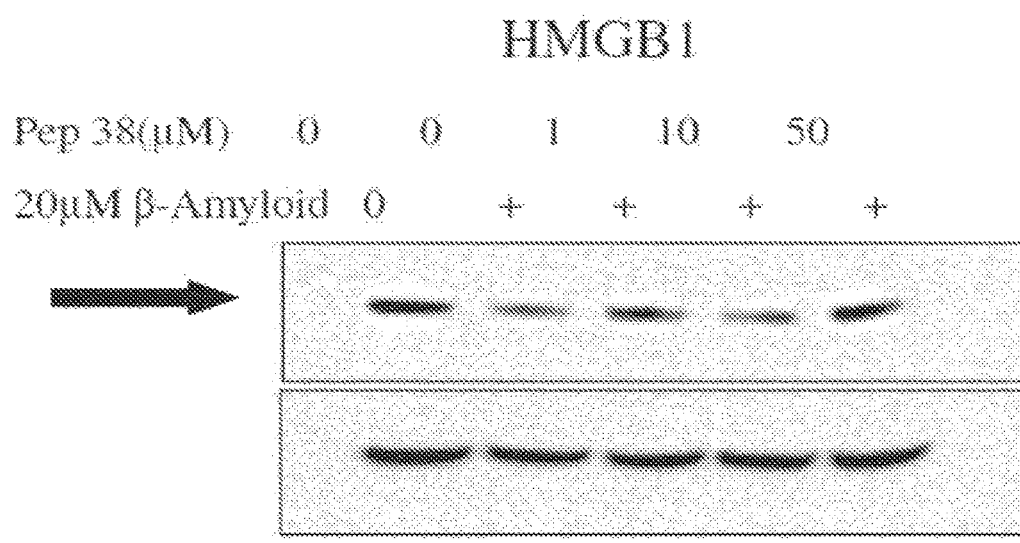
Figure 64:
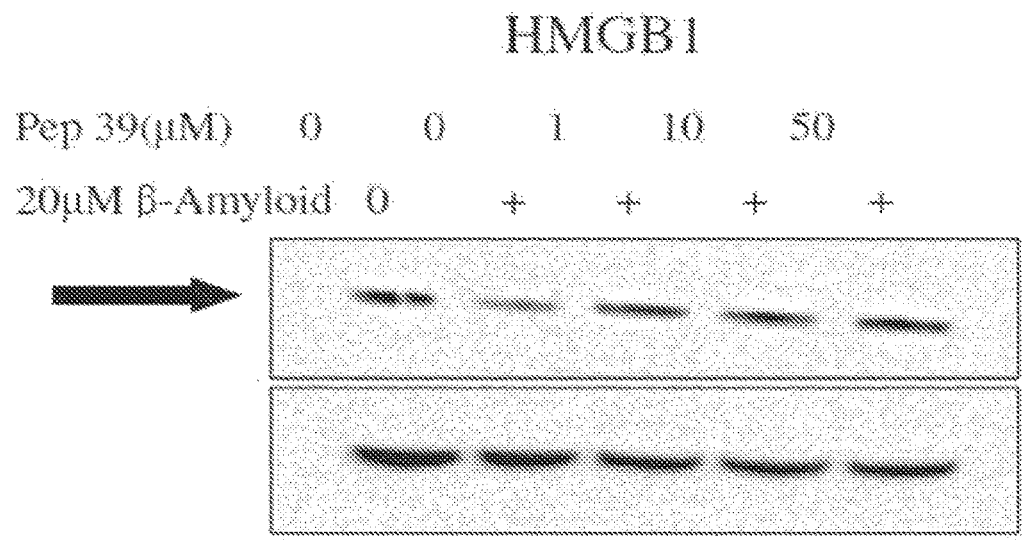
Figure 65:
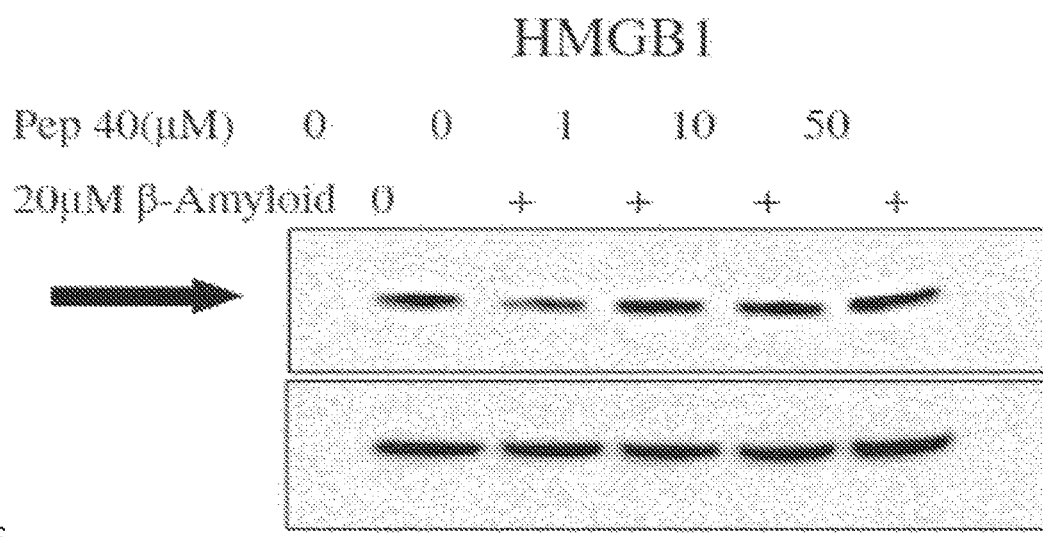
Figure 66:
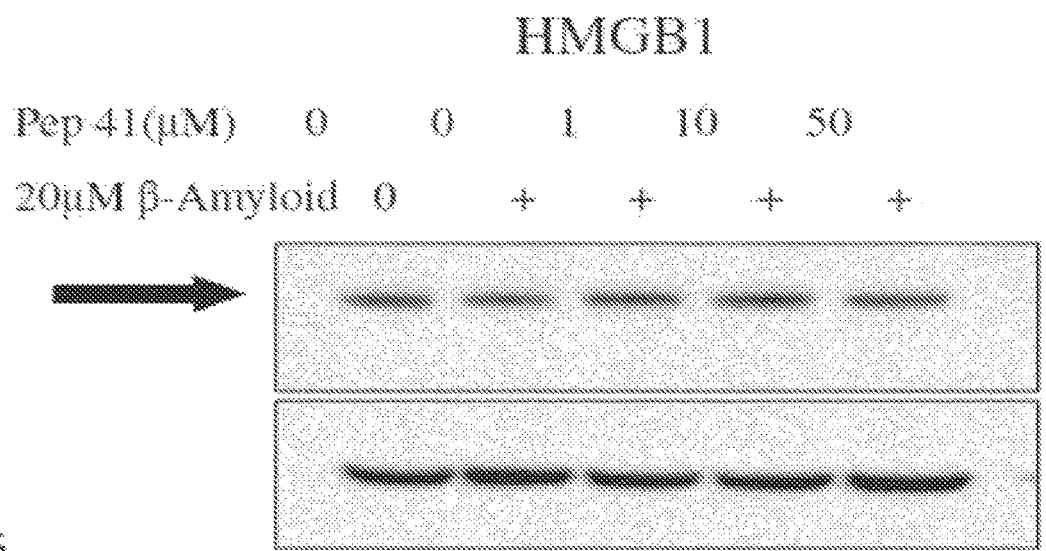
Figure 67:
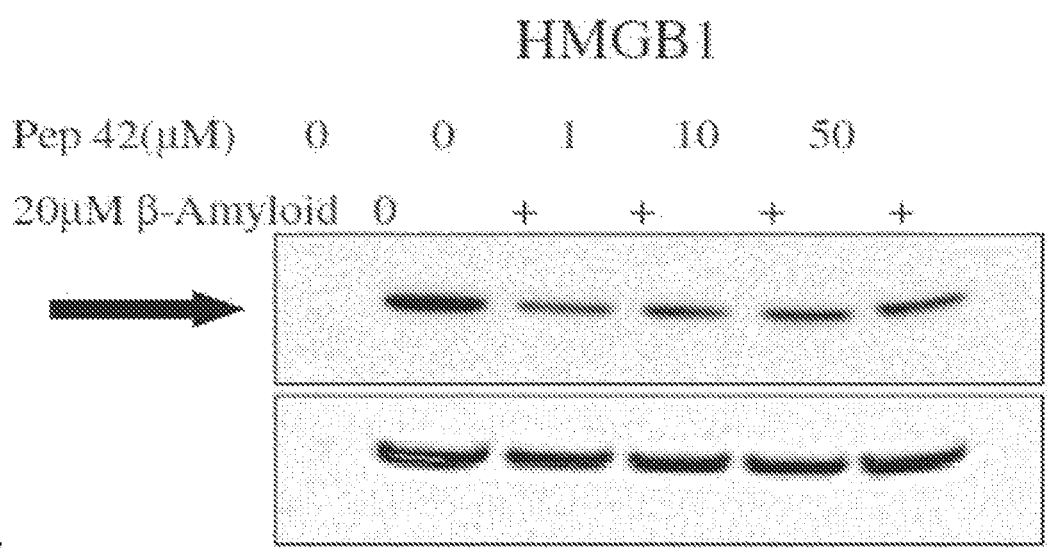
Figure 68:
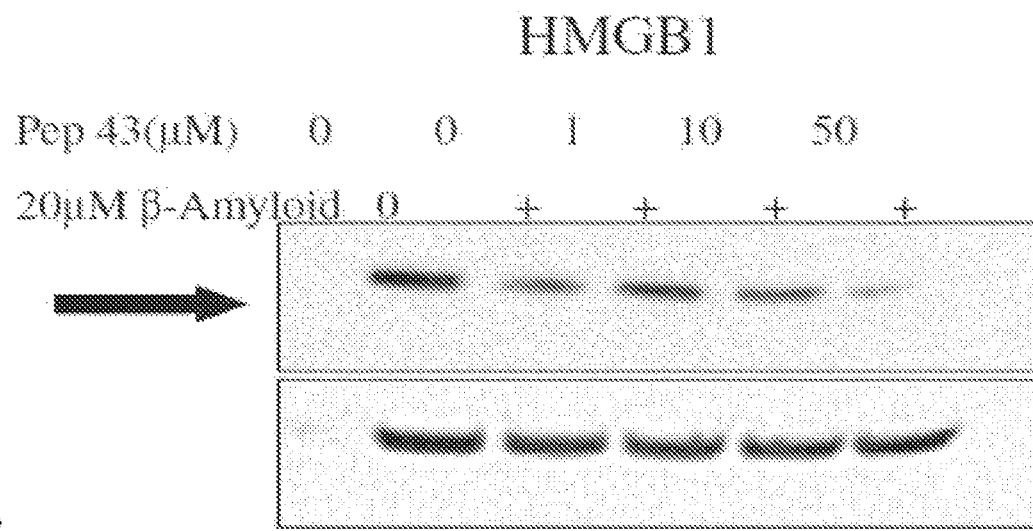
Figure 69:
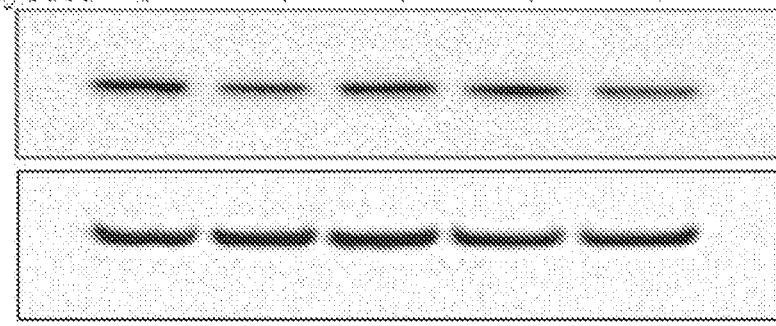
Figure 70:
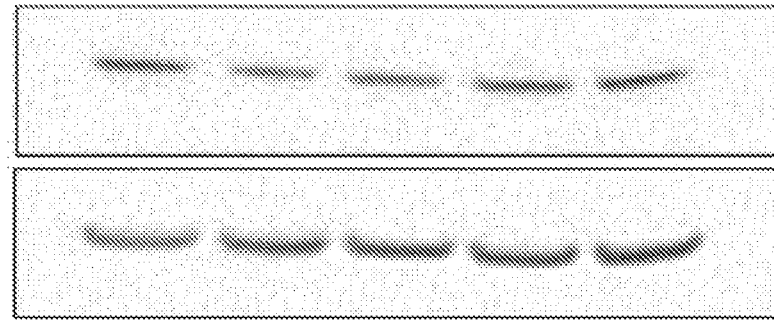
Figure 71:
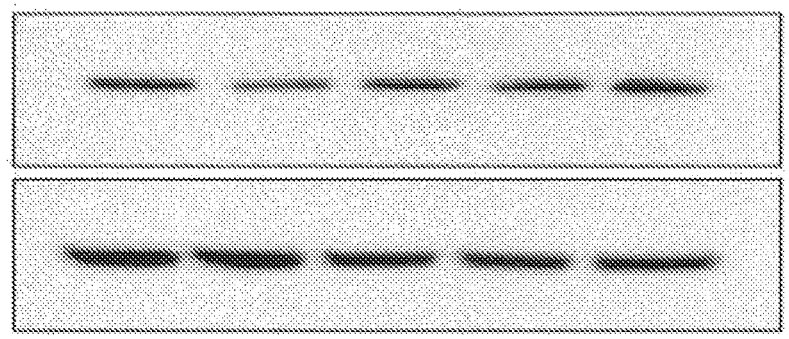
Figure 72:
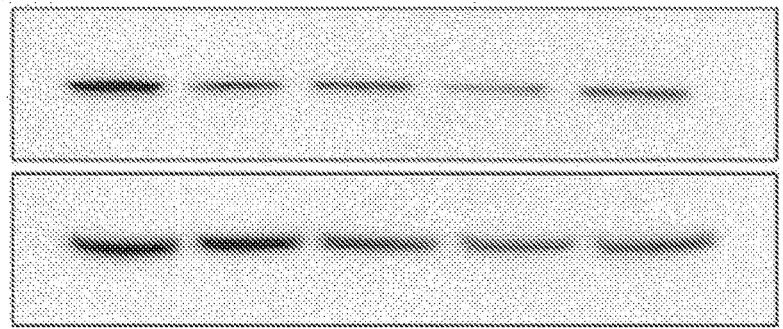
Figure 73:
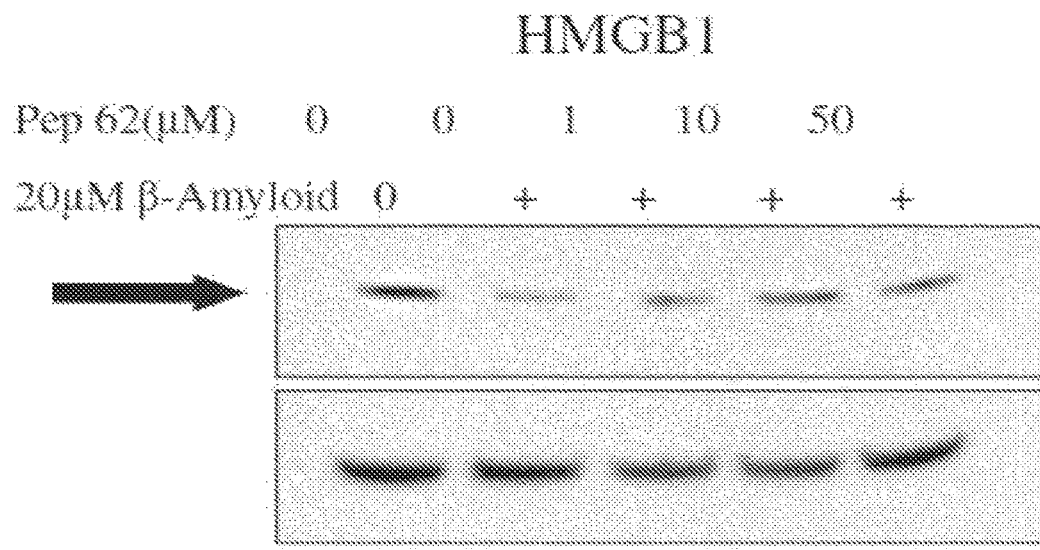
Figure 74:
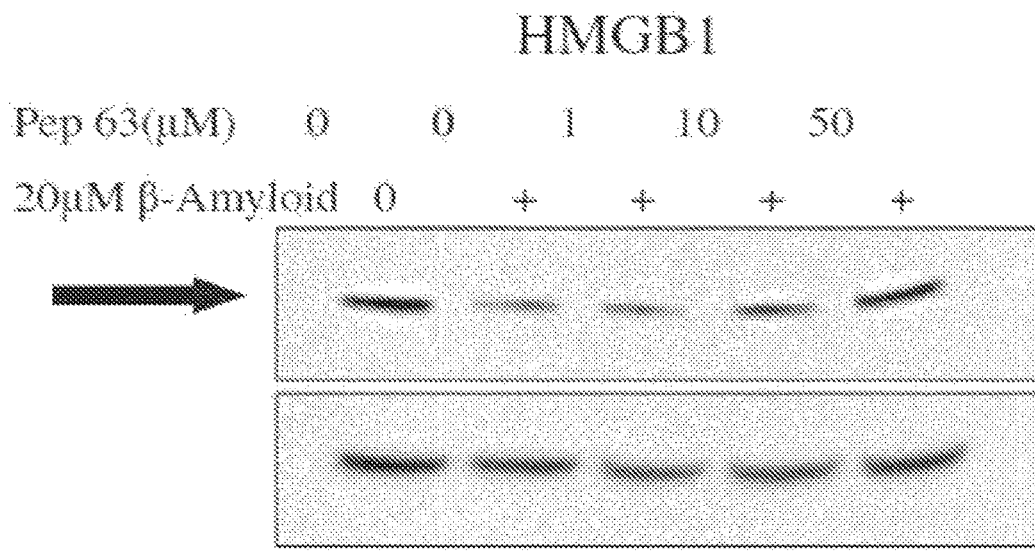
Figure 75:
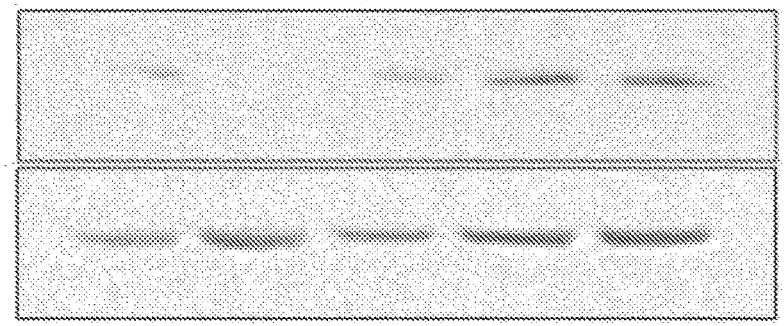
Figure 76:
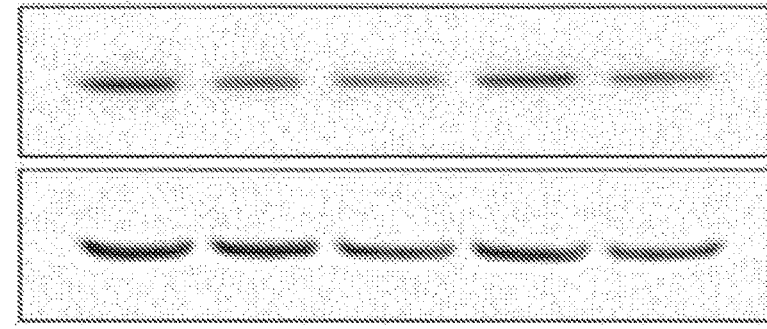
Figure 77:
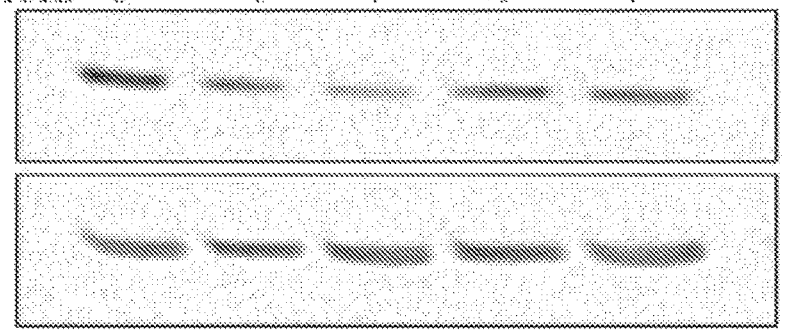
Figure 78:
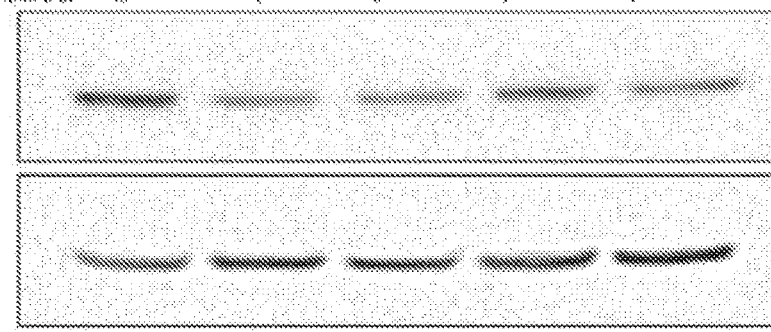
Figure 79:
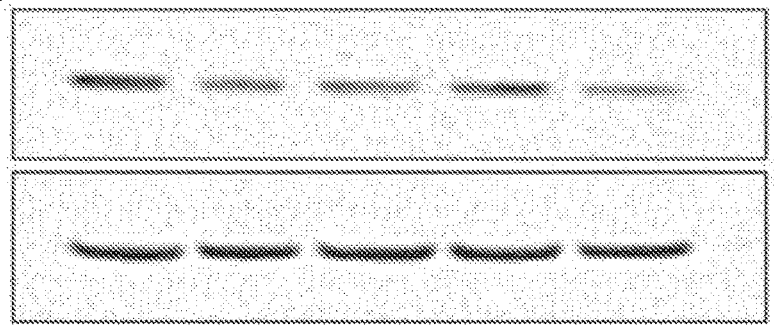
Figure 80:
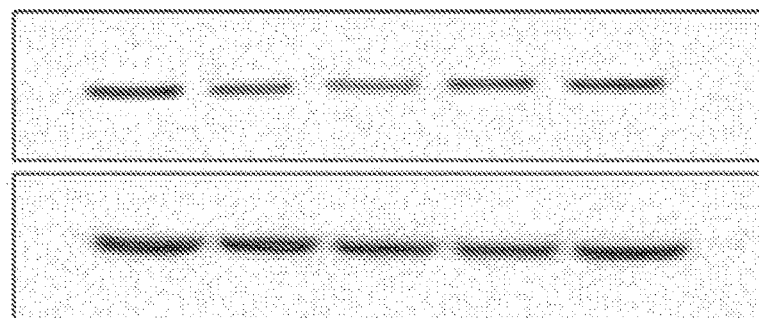
Figure 81:
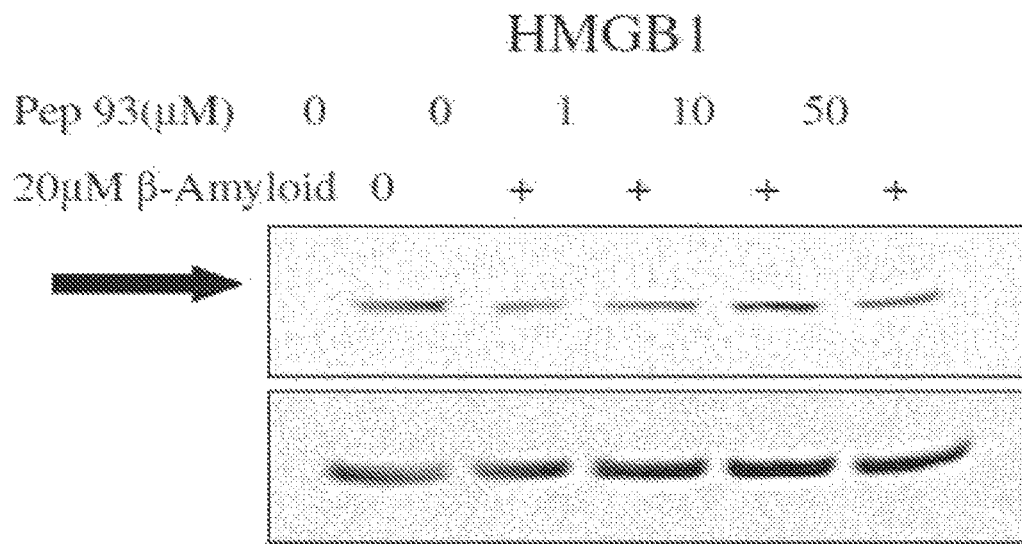
Figure 82:
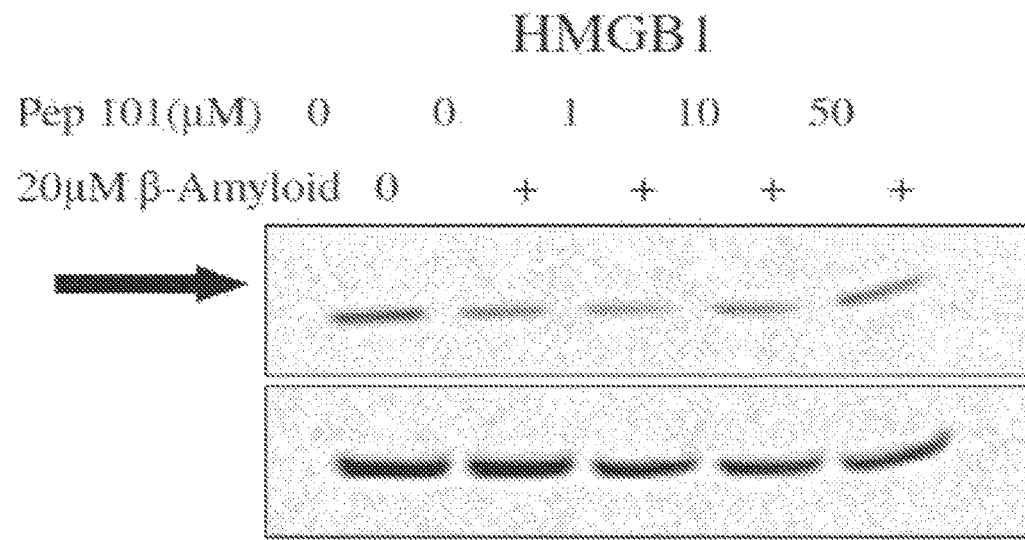
Figure 83:
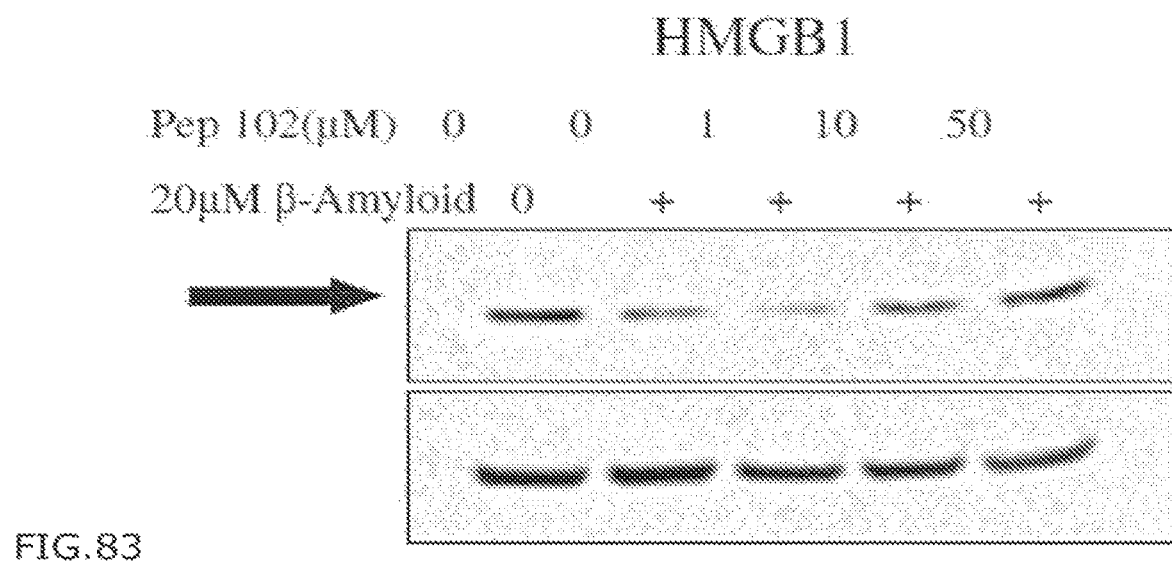
Figure 84:
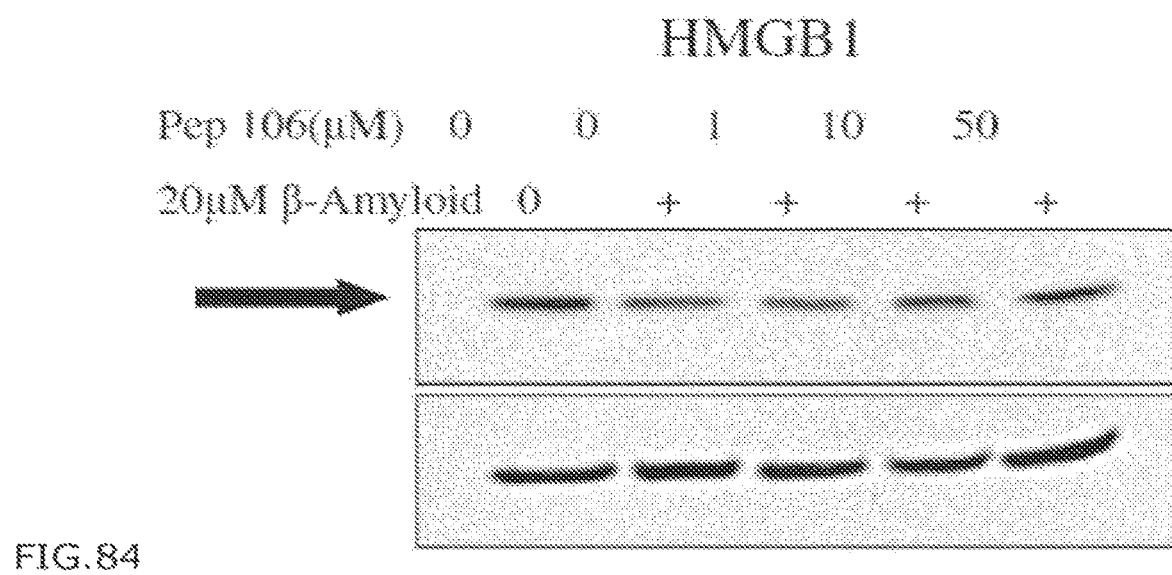
Figure 85:
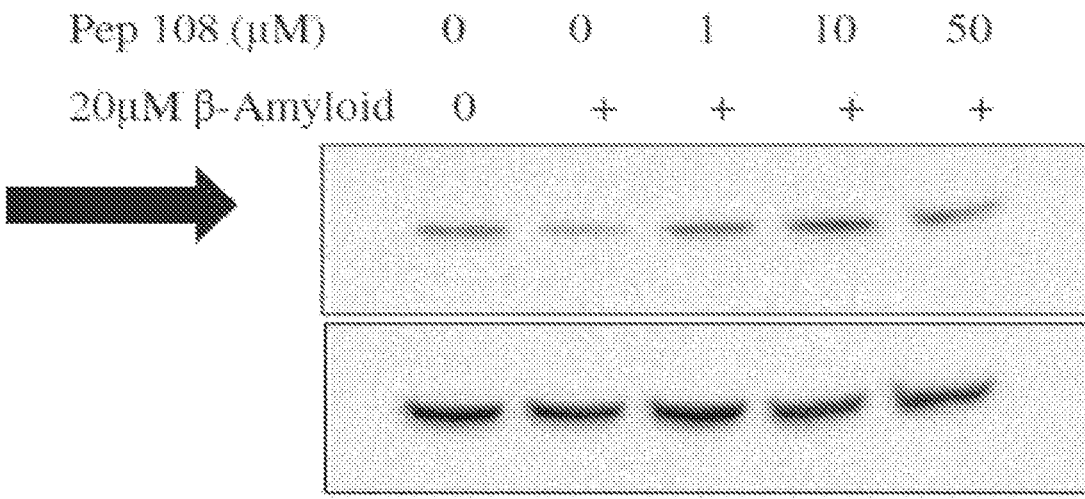
Figure 86:
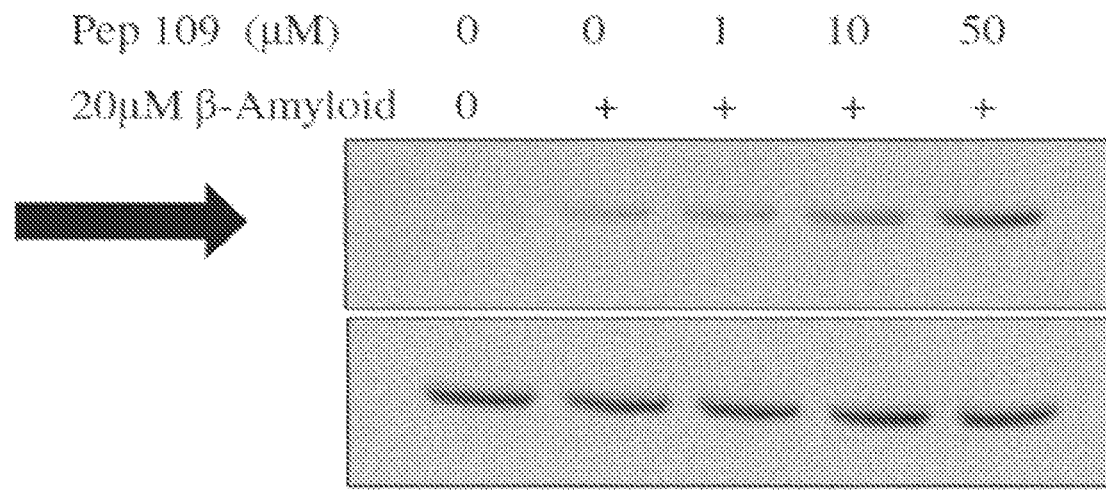
Figure 91:
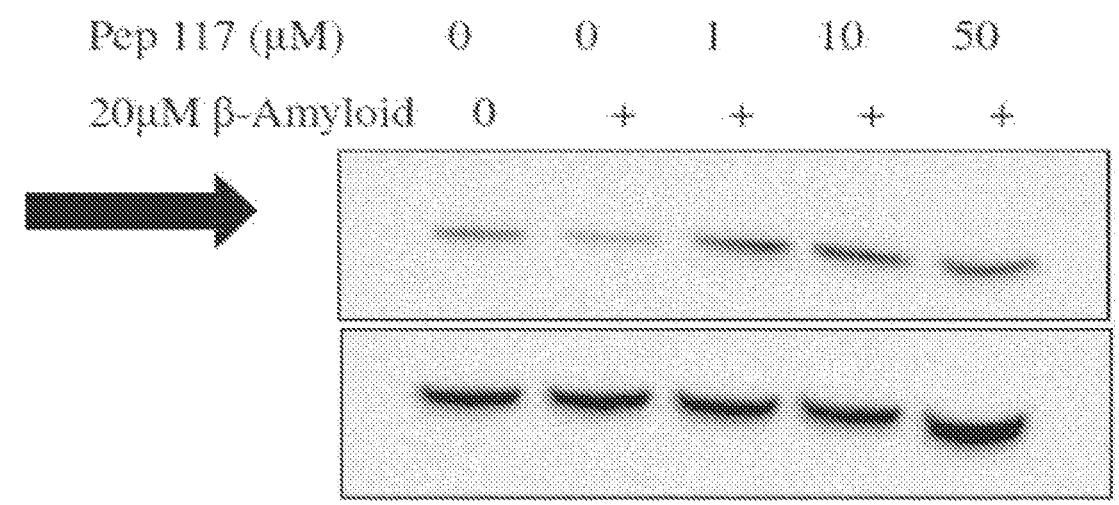
Figure 92:
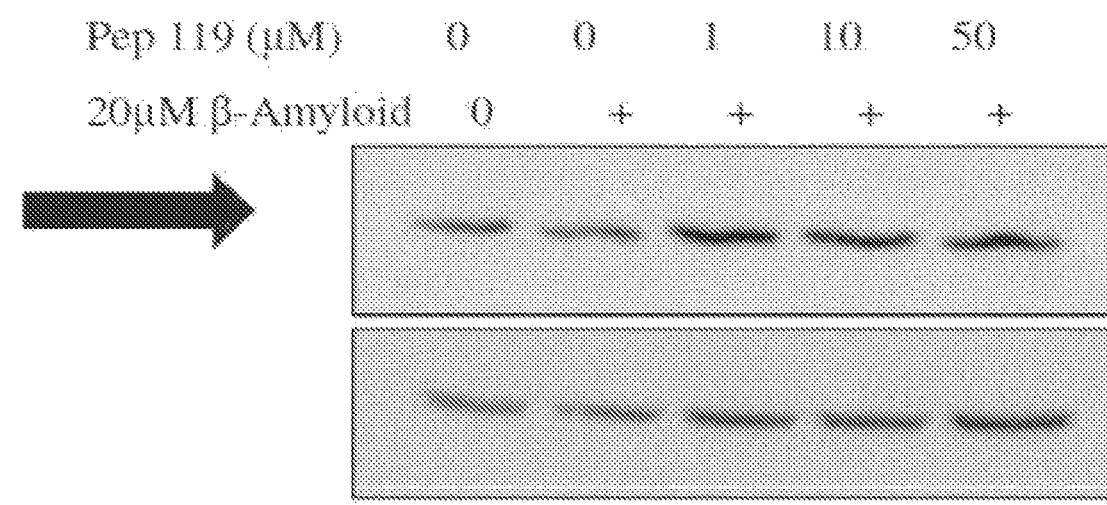
Figure 95:
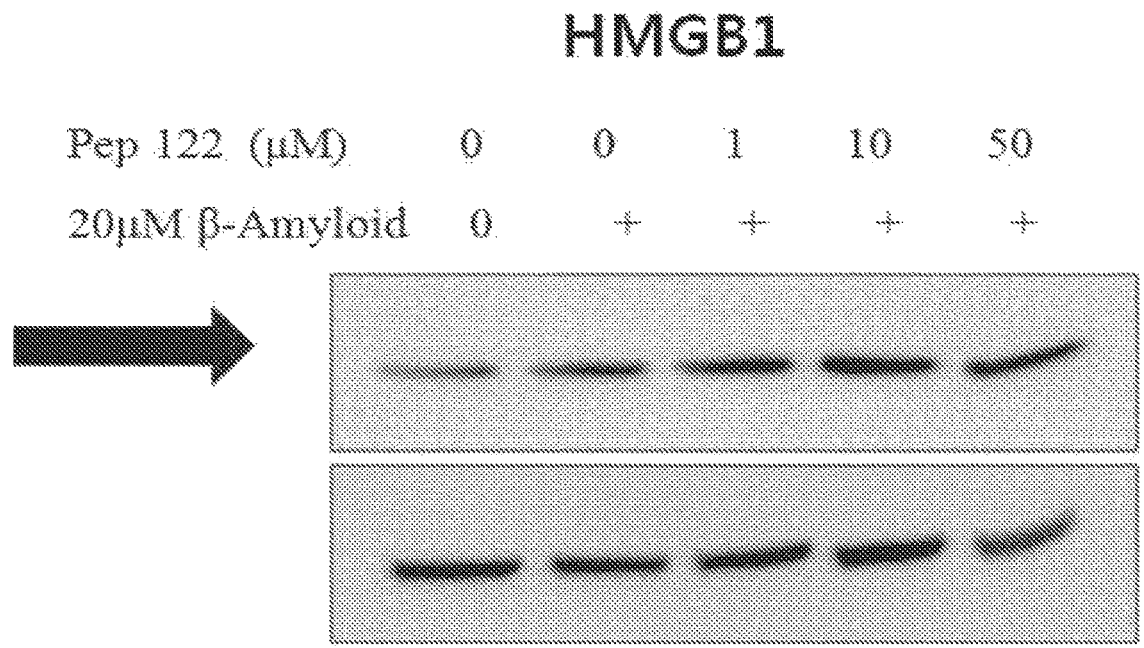
Figure 96:
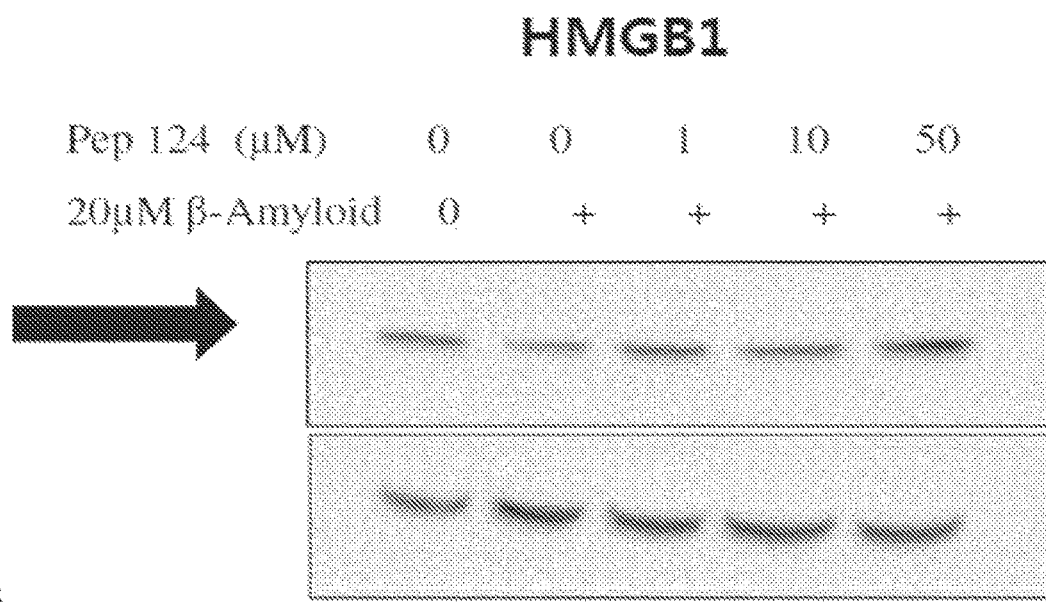
Figure 97:
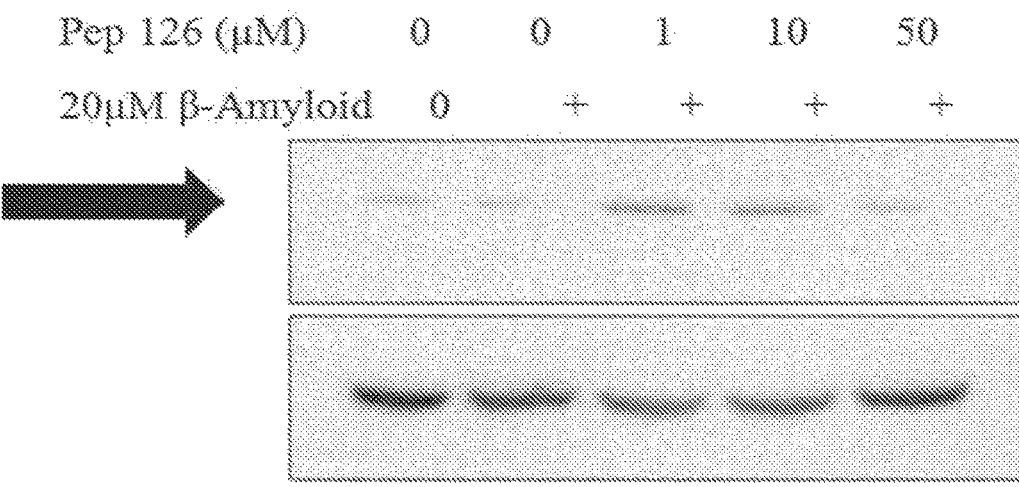
Figure 98:
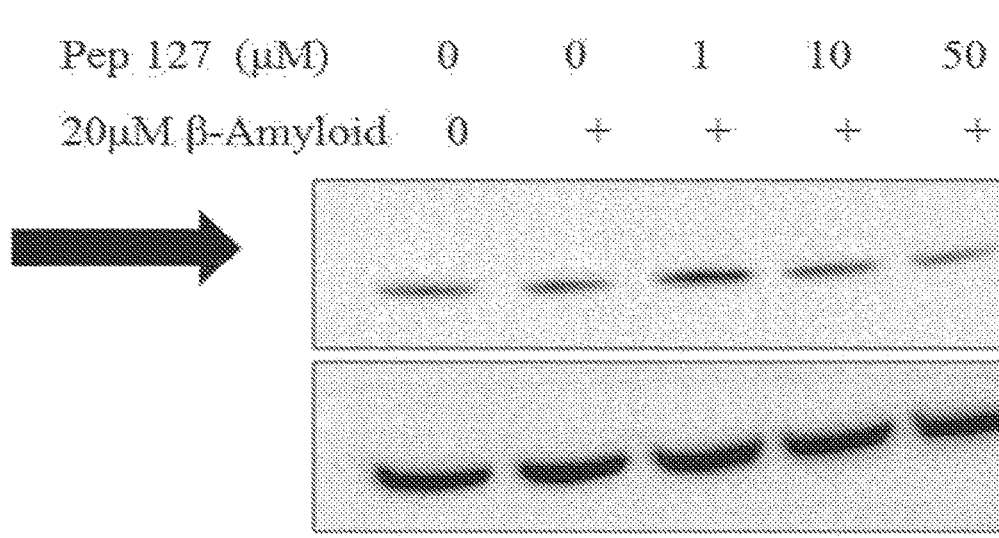
Figure 99:
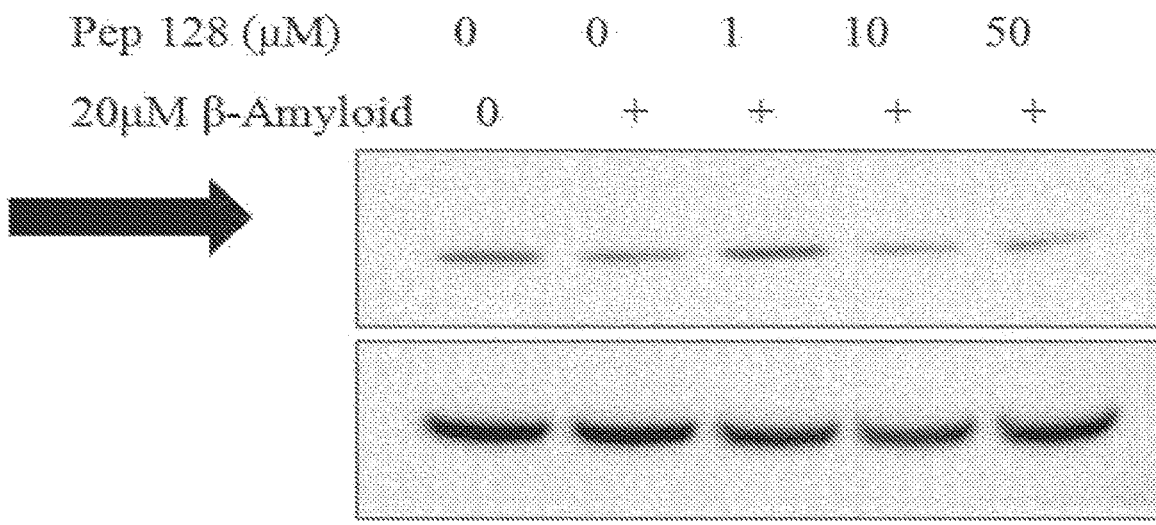
Figure 100:
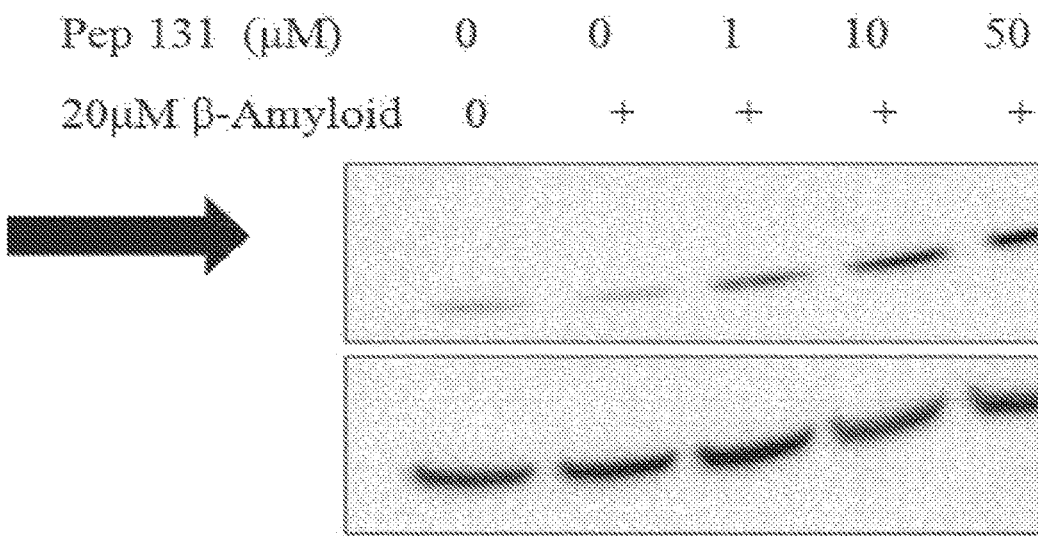
Figure 101:
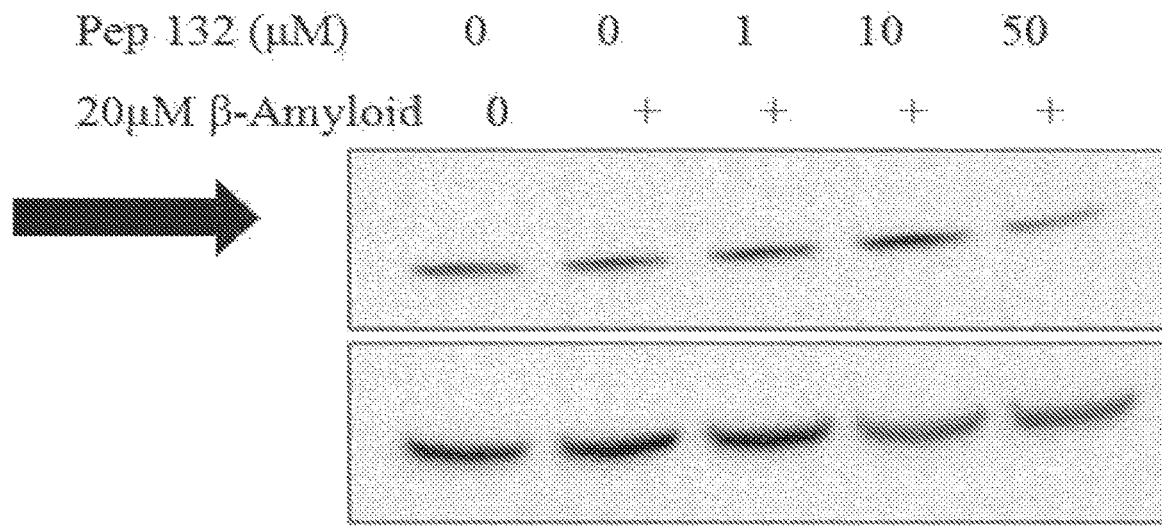
Figure 102:
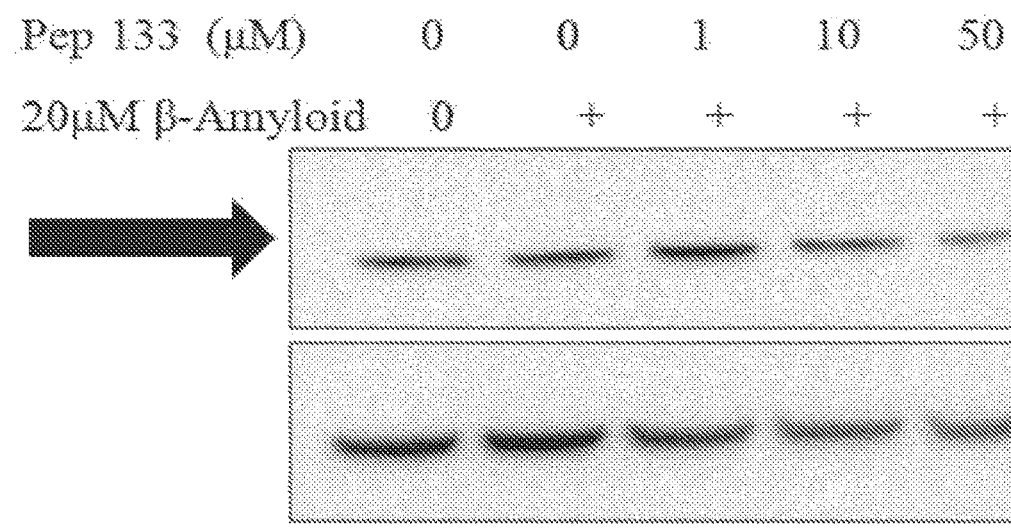
Figure 103:
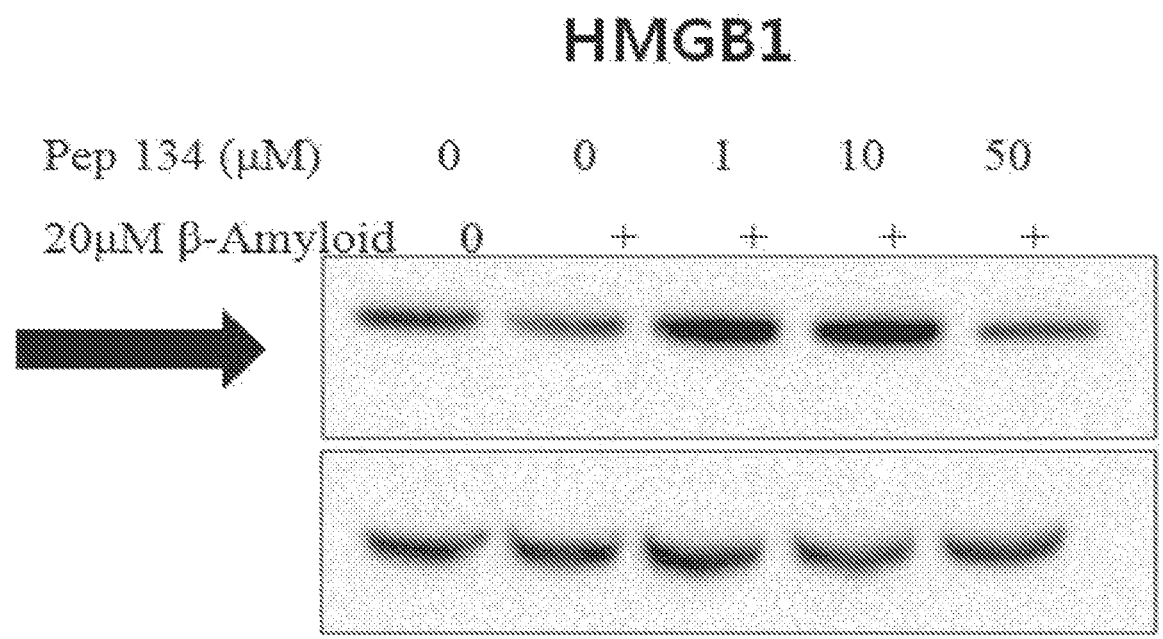
Figure 104:
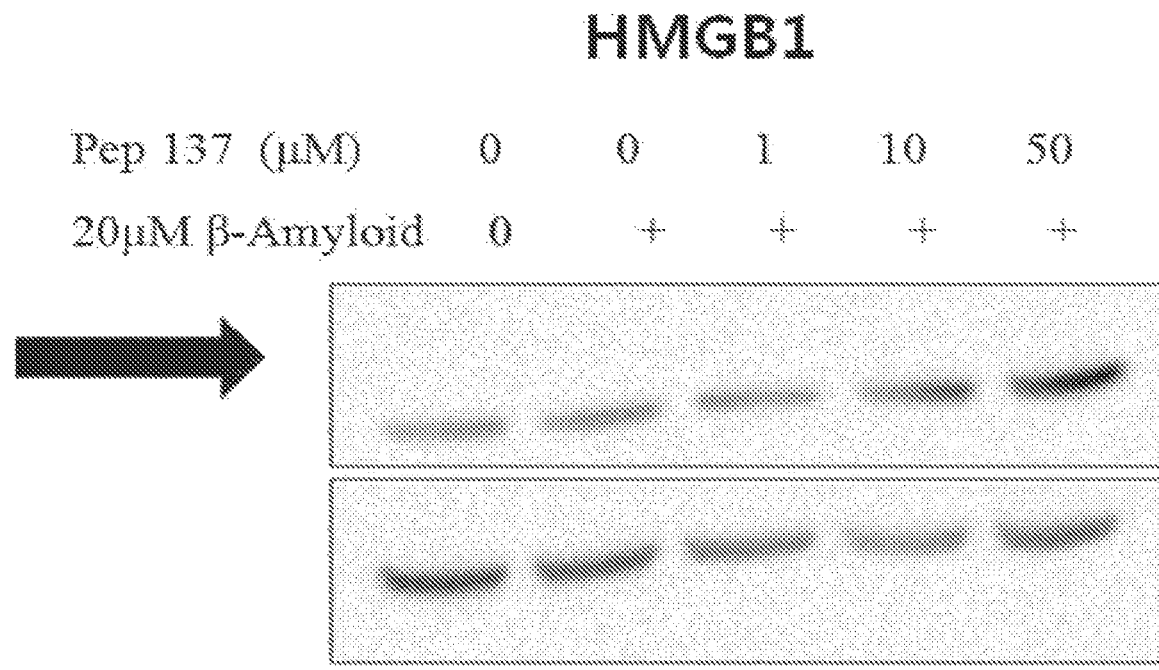
Figure 105:
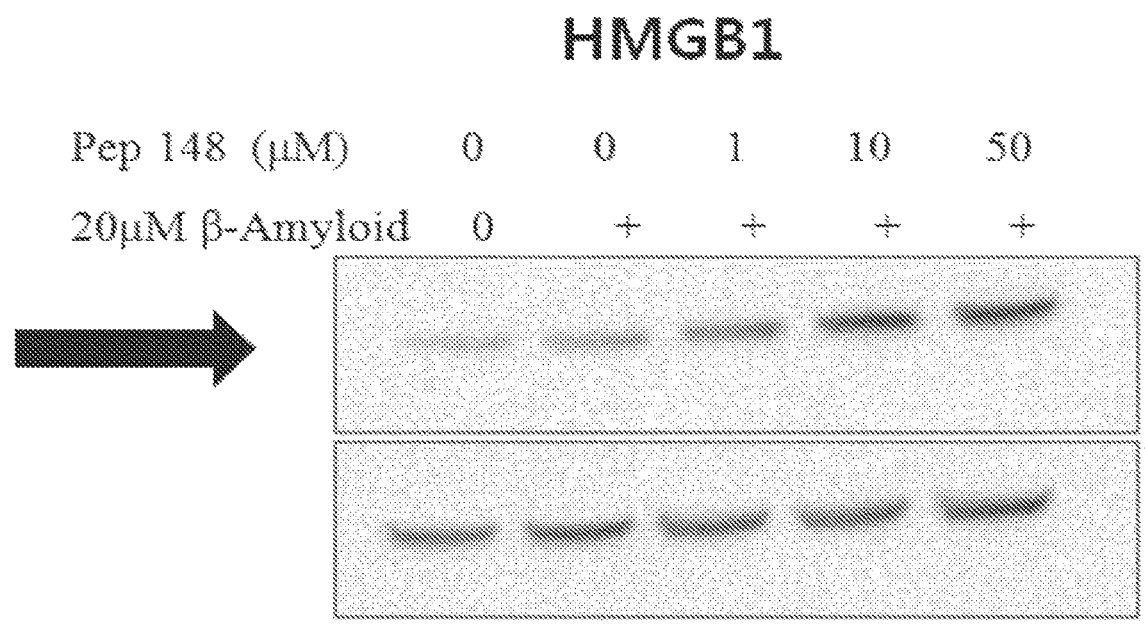
Figure 106:
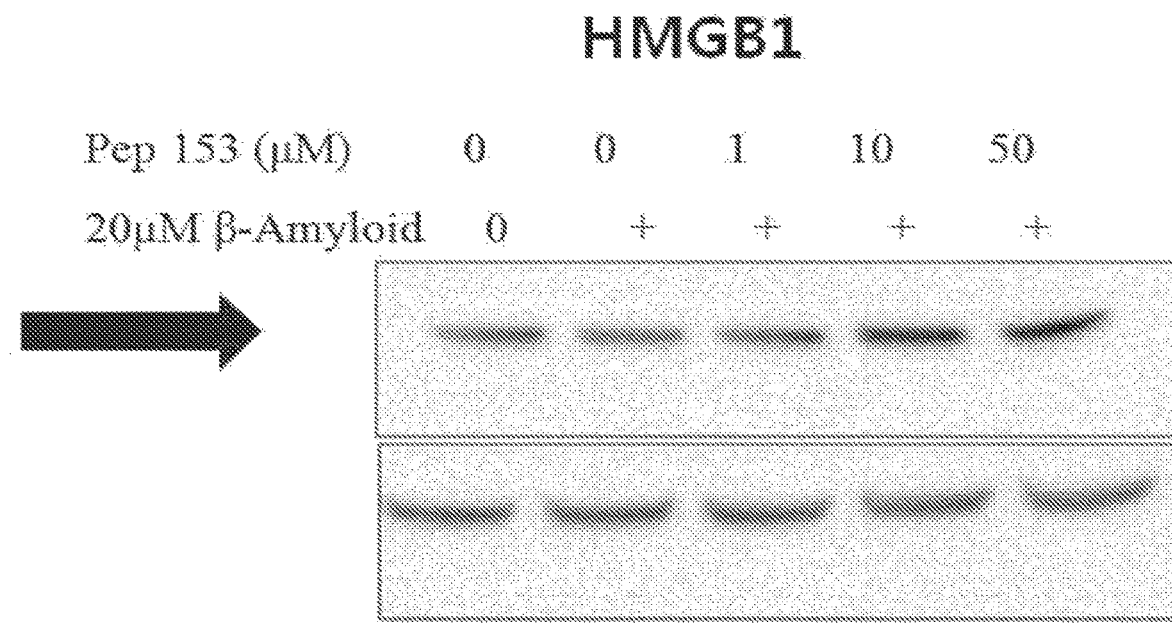
Figure 107:
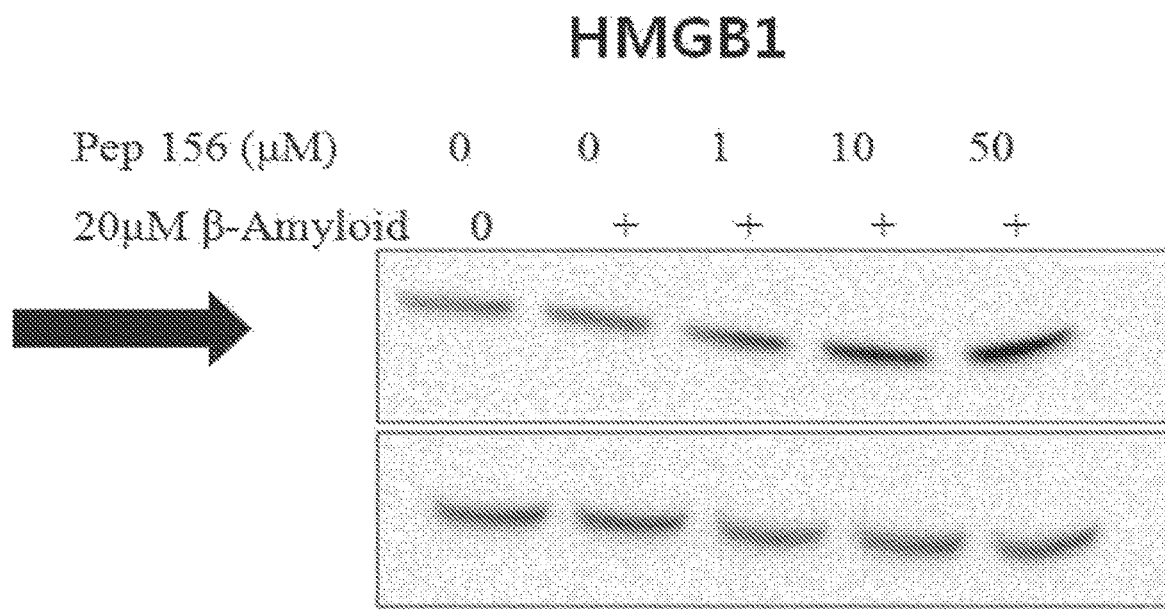
Figure 108:
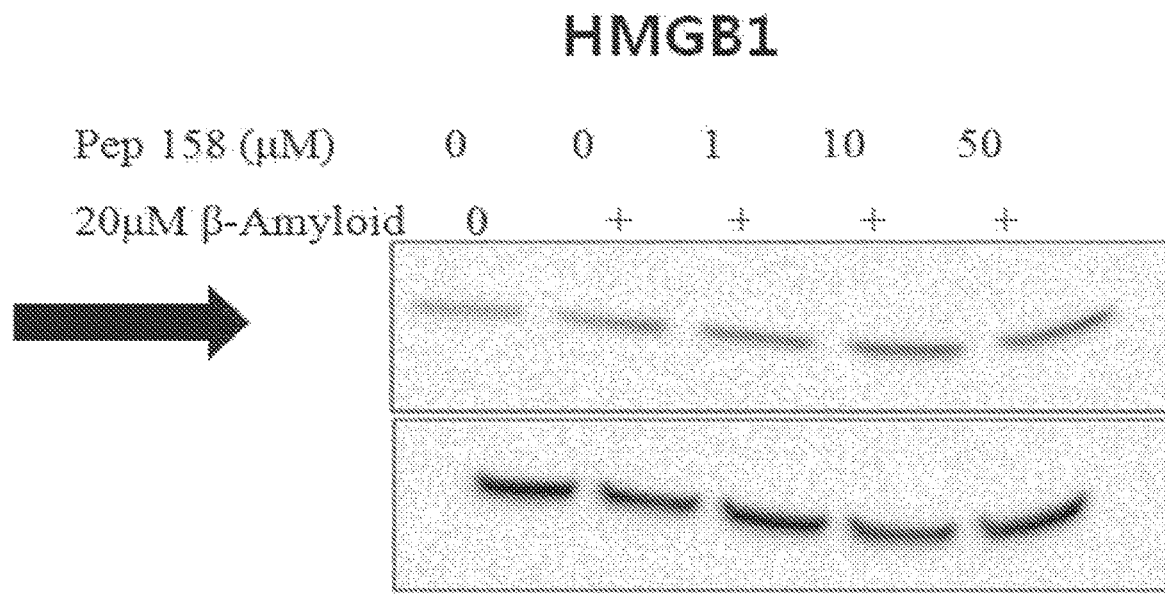

As a result of the western blot analysis, peptides showing accumulation of HMGB1 in the cell were selected. FIG. 36 to FIG. 108 are the western blot results of selected peptides. Tubulins in these figures are used for confirming protein expression. The sequences of the selected peptides are as follows:

SEQ ID NO: 1, SEQ ID NO: 2, SEQ ID NO: 4, SEQ ID NO: 6, SEQ ID NO: 7, SEQ ID NO: 8, SEQ ID NO: 9, SEQ ID NO: 10, SEQ ID NO: 12, SEQ ID NO: 14, SEQ ID NO: 15, SEQ ID NO: 17, SEQ ID NO: 18, SEQ ID NO: 20, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 44, SEQ ID NO: 45, SEQ ID NO: 52, SEQ ID NO: 57, SEQ ID NO: 60, SEQ ID NO: 61, SEQ ID NO: 62, SEQ ID NO: 64, SEQ ID NO: 65, SEQ ID NO: 67, SEQ ID NO: 68, SEQ ID NO: 69, SEQ ID NO: 91, SEQ ID NO: 99, SEQ ID NO: 100, SEQ ID NO: 104, SEQ ID NO: 106, SEQ ID NO: 107, SEQ ID NO: 108, SEQ ID NO: 109, SEQ ID NO: 111, SEQ ID NO: 112, SEQ ID NO: 115, SEQ ID NO: 117, SEQ ID NO: 118, SEQ ID NO: 119, SEQ ID NO: 120, SEQ ID NO: 122, SEQ ID NO: 124, SEQ ID NO: 125, SEQ ID NO: 126, SEQ ID NO: 129, SEQ ID NO: 130, SEQ ID NO: 131, SEQ ID NO: 132, SEQ ID NO: 135, SEQ ID NO: 146, SEQ ID NO: 151, SEQ ID NO: 154, and SEQ ID NO: 156.

The invention claimed is:

1. A method of treating or preventing inflammatory disease in a patient, comprising administering to the patient an isolated peptide having anti-inflammatory activity, wherein the peptide consists of the amino acid sequence of SEQ ID NO: 73 or SEQ ID NO: 130.

2. The method according to claim 1, wherein the inflammatory disease is general or localized inflammatory disease; gastro-intestinal related diseases; dermal related diseases; vascular related disease; respiratory diseases; bone, joint, muscle, and connective tissue related diseases; urogenital disorders; central or peripheral nervous system related diseases; virus; or autoimmune diseases.

3. The method according to claim 1, wherein the daily dose of the peptide is 0.1 µg/kg/day to 1 g/kg/day.

4. A method of treating or preventing skin inflammation comprising administering an isolated peptide having anti-inflammatory activity, wherein the peptide consists of the amino acid sequence of SEQ ID NO: 73 or SEQ ID NO: 130.

5. The method according to claim 4, wherein the daily dose of the peptide is 0.1 µg/kg/day to 1 g/kg/day.

6. The method according to claim 2, wherein the central or peripheral nervous system related disease is Alzheimer's disease; meningitis; encephalitis; multiple sclerosis; cerebral infarction; cerebral embolism; Guillain-Barre syndrome; neuritis; neuralgia; spinal cord injury; paralysis; or uveitis.

* * * * *